(12) United States Patent
Hubschwerlen et al.

(10) Patent No.: US 7,888,359 B2
(45) Date of Patent: Feb. 15, 2011

(54) CYCLOHEXYL OR PIPERIDINYL CARBOXAMIDE ANTIBIOTIC DERIVATIVES

(75) Inventors: Christian Hubschwerlen, Durmenach (FR); Rueedi Georg, Allschwil (CH); Jean-Philippe Surivet, Kembs (FR); Cornelia Zumbrunn Acklin, Basel (CH)

(73) Assignee: Actelion Pharmaceutical Ltd., Allschwil (CH)

( * ) Notice: Subject to any disclaimer, the term of this patent is extended or adjusted under 35 U.S.C. 154(b) by 199 days.

(21) Appl. No.: 12/294,163

(22) PCT Filed: Mar. 22, 2007

(86) PCT No.: PCT/IB2007/051002
§ 371 (c)(1),
(2), (4) Date: Sep. 23, 2008

(87) PCT Pub. No.: WO2007/107965
PCT Pub. Date: Sep. 27, 2007

(65) Prior Publication Data
US 2009/0105232 A1    Apr. 23, 2009

(30) Foreign Application Priority Data
Mar. 23, 2006   (WO) ............... PCT/IB2006/050901

(51) Int. Cl.
| | |
|---|---|
| A01N 43/58 | (2006.01) |
| A01N 43/60 | (2006.01) |
| A01N 43/42 | (2006.01) |
| A01N 43/54 | (2006.01) |
| A01N 43/90 | (2006.01) |
| A61K 31/50 | (2006.01) |
| A61K 31/495 | (2006.01) |
| A61K 31/517 | (2006.01) |
| A61K 31/519 | (2006.01) |
| A61K 31/44 | (2006.01) |
| A61K 31/47 | (2006.01) |
| C07D 239/70 | (2006.01) |
| C07D 475/00 | (2006.01) |
| C07D 471/00 | (2006.01) |
| C07D 487/00 | (2006.01) |
| C07D 491/00 | (2006.01) |
| C07D 495/00 | (2006.01) |
| C07D 497/00 | (2006.01) |
| C07D 241/36 | (2006.01) |

(52) U.S. Cl. ............ 514/249; 514/258.1; 514/262.1; 514/266.1; 514/306; 514/311; 544/253; 544/257; 544/350; 544/353

(58) Field of Classification Search ............ 514/249, 514/258.1, 262.1, 266.1, 306, 311; 544/253, 544/257, 350, 353
See application file for complete search history.

(56) References Cited

U.S. PATENT DOCUMENTS
6,376,514 B1    4/2002  Degenhardt et al.

FOREIGN PATENT DOCUMENTS
| | | |
|---|---|---|
| WO | WO 02/24684 A | 3/2002 |
| WO | WO 2004/058144 A | 7/2004 |
| WO | WO 2006/046552 | 5/2006 |

OTHER PUBLICATIONS

Patani et. al., Chemical Reviews, 1996, American Chemical Society, vol. 96, No. 8, pp. 3147-3176.*
International Search Report (Form PCT/ISA/210) in PCT/IB2007/051002.
Written Opinion of the International Searching Authority (Form PCT/ISA/237) in PCT/IB2007/051002.
Gould, "Salt Selection for Basic Drugs", International Journal of Pharmaceutics (1986), vol. 33, pp. 201-217.
Palucki, "Synthesis of Oxygen Heterocycles via a Palladium-Catalyzed C-O Bond Forming Reaction", Journal of American Chemical Society (1996), vol. 118, 10333.
Klapars, "A General and Efficient Copper Catalyst for the Amidation of Aryl Halides", Journal of American Chemical Society (2002), vol. 124, 7421.

(Continued)

Primary Examiner—Sreeni Padmanabhan
Assistant Examiner—Sarah Pihonak
(74) Attorney, Agent, or Firm—Hunton & Williams LLP

(57) ABSTRACT

The invention relates to antibiotic cyclohexyl or piperidinyl carboximide derivatives of formula (I)

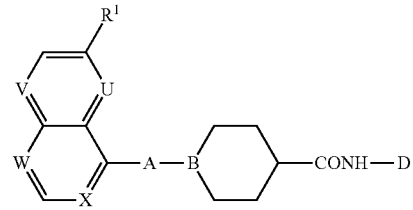

wherein
R$^1$ represents hydrogen, halogen, (C$_1$-C$_4$)alkyl, (C$_1$-C$_4$) alkoxy, cyano or COOR$^2$, R$^2$ being (C$_1$-C$_4$)alkyl;
one or two of U, V, W and X represent(s) N and the remaining represent each CH, or, in the case of X, may also represent CR$^X$, R$^X$ being a halogen atom;
either B represents N and A represents CH$_2$CH$_2$ or CH(OR$^3$)CH$_2$, or B represents CH or C(OR$^4$) and A represents OCH$_2$, CH$_2$CH(OR$^5$), CH(OR$^6$)CH$_2$, CH(OR$^7$)CH(OR$^8$), CH=CH or CH$_2$CH$_2$;
each of R$^3$, R$^4$, R$^5$, R$^6$, R$^7$, and R$^8$ represents independently hydrogen, SO$_3$H, PO$_3$H$_2$, CH$_2$OPO$_3$H$_2$ or COR$^9$, R$^9$ being either CH$_2$CH$_2$COOH or such that R$^9$—COOH is naturally occurring amino acid or dimethylaminoglycine;
and to salts of such compounds of formula (I).

11 Claims, No Drawings

OTHER PUBLICATIONS

Adams, "Synthesis of Antimalarials—VI. Synthesis of Certain 1,5- and 1,8-Naphthyridine Derivatives", Journal of American Chemical Society (1946), vol. 68, 1317.

Williamson, "Heterocyclic Compounds—Six Membered Heterocycles Containing Two Hetero Atoms and their Benzo Derivatives" (1957), 6, 324.

Abe, et al., "A Novel Class of Orally Active Non-Peptide Bradykinin Bz Receptor Antagonists. 3. Discovering Bioisosteres of the Imidazo[1,2-alpyridine Moiety", Journal of Medicinal Chem. (1998), 41, 4062.

Ritter, "Synthetic Transformations of Vinyl and Aryl Triflates", Synthesis (Jan. 1993), pp. 735-762.

Radinov, "Synthesis of 4-Amino3-pyridinyl and 4-Amino-5-pyrimidinyl Aryl Ketones and Related Compounds via an ovtho-Lithiation Reaction" Synthesis (Nov. 1986), 886.

Bowden, Jones, et al, "Researches on Acetylenic Compounds. Pad I. The Prepamtion of Acety lenic Eetones by Oxidation of Acetylenic Carbinols and Glycols", Journal of Chem. Soc. (1946), pp. 39-45.

Ho, et al., "Resolution of (f)-2-Tetradecyloxiranecarboxylic Acid. Absolute Configuration and Chiral Synthesis of the Hypoglycemic R Enantiomer and Biological Activity of Enantiomers", Journal of Med. Chem. (1987), 30, 1094.

Reedich et al, Benzobicyclo[3.1.O]hexene Derivatives from Benzosemibullvalene. COP- and CO-Bridged Naphthalenes, Journal of Org. Chem., (1985), 50, 3535-3541.

Benz, in Comprehensive Organic Synthesis, B.M. Trost, I. Fleming, Eds; Pergamon Press: New York (1991), vol. 6, pp. 381-417.

Mancuso, et al., "Activated Dimethyl Sulfoxide: Useful Reagents for Synthesis", Synthesis (1981), pp. 165-185.

Dess, et al., "A Useful 12-I-5 Triacetoxyperiodinane (the Dess-Martin Periodinane) for the Selective Oxidation of Primary or Secondary Alcohols and a Variety of Related 12-1-5 Species" Journal of American Chemical Society. (1991), 113, pp. 7277-7287.

Ohira, "Methanolysis Of Dimethyl (1-Dia20-2-Oxopropyl) Phosqhonate: Generation Of Dimethyl (Diazomethyl)Phospnonate and Reaction With Carbonyl Compounds", Synthetic Communication, (1989), 19, pp. 561-564.

Hodgson, et al., Extended Scope of Dirhodium(II)-Catalysed Enantioselective Intramolecular 1,3-Dipolar Cycloadditions of Carbonyl Ylides with Alkene and Alkyne Dipolarophiles Synlett (Dec. 2002), pp. 59-62.

Muller, et al., "An Improved One-pot Procedure for the Synthesis of Alkynes from Aldehydes" Synlett (Jun. 1996), 521-522.

Sonogashira, "Cross-Coupling Reactions to SP-Carbon Atoms" Diedrich, F., Stang, P.J., Eds; Wiley VCH: New York (1998), pp. 203-229.

Siegel, et al., Heterogeneous Catalytic Hydrogenation of C=C and C=C, University of Arkansas, Fayetteville, AR, Pergamon Press: New York (1991), vol. 8, p. 417-488.

Blakemore, The Modified Julia Olefination: Alkene Synthesis Via Thecondensation of Metallated Heteroarylalkylsulfones With Carbonyl Compounds Department of Chemistry, University of Leeds, Leeds, West Yorkshire, UK LS29JT, Journal of American Chemical Society Perkin Trans. 1(2002), 2563-2585.

Kolb, et al., Catalytic Asymmetric Dihydroxylation, Chemical Reviews, (Jul. 1994), 94, 2483-2547.

Bal, et al.. "Oxidation of α, β-Unsaturated Aldehydes", Tetrahedron (Feb. 1981), vol. 37, 2091-2096.

Wittig, et al., "Methylenecyclohexane", Organic Syntheses, Coll. (1973), vol. 40, 5, 751.

Smith, et al.,"Comprehensive Organic Synthesis", B.M. Trost, I. Fleming, Editors; Pergamon Press: New York (1991), vol. 8, p. 703-731.

Pelter, et al., Comprehensive Organic Synthesis, B.M. Trost, I. Fleming, Eds; Pergamon Press: New York (1991), vol. 7, p. 593-611.

Cryle, et al., "Cyclopropyl Containing Fatty Acids as Mechanistic Probes for Cytochromes P450", Org. Chem. (Feb. 2005), 70, 2455-2469.

Table 11. Reaction of 2,2-Dimethyl-1,3-dioxolanwe ith Formaldehyde in the Presence of UV Light α, Journal of Org. Chem.(1988), 53, 2861-2863.

Noyori, "Asymmetric Transfer Hydrogenation Catalyzed by Chiral Ruthenium Complexes", Accounts of Chemical Research (1997), 30, 97-102.

Ueda, "Phosphonooxymethyl Prodrugs of the Broad Spectrum Antifungal Azole, Ravuconazole: Synthesis and Biological Properties" Bioorganic & Medicinal Chemistry Letters (2003), 13, 3669-3672.

Ando, "1,5-Lactamized Sialyl Acceptors for Various Disialoside Syntheses: Novel Method for the Synthesis of Glycan Portions of Hp-s6 and HLG-2 Gangliosides" Angewandte Chemie Int. Ed. (2005), 44, 6759-6763.

Suggs, et al. "Facile Synthesis of 8-Substituted Quinolines", Journal of Org. Chem. (1980), 45, 1514-1515.

Miyaura, et al., "The Palladium-Cataly Zed Cross-Coupling Reaction of Phenylboronic Acid With Haloarenes in the Presence of Bases", Synth. Commun. (1981), 11, 513.

Cha, "Acyclic Stereocontrol Induced by Allylic Alkoxy Groups. Synthetic Applications of Stereoselective Dihydroxylation in Natural Product Synthesis", Chem. Rev. (1995), 95, 1761-1795.

Weissman, et al., "Ligand-Free Palladium-Catalyzed Cyanation of Aryl Halides", Journal of Org. Chem. (2005), 70, 1508-1510.

Kolb, et al. "A Simplified Procedure for the Stereospecific Transformation of 1,2-Diols into Epoxides", Tetrahedron (1992), 48, 10515-10530.

Rieger, et al., "Design, Synthesis, and Evaluation of Novel A2a Adenosine Receptor Agonists", Journal of Med. Chem. (2001), 44, 531-539.

Trost, et al., "Chemoselective Oxidation of Sulfides to Sulfones with Potassium Hydrogen Persulfate", Tetrahedron Letters (1981), vol. 22, pp. 1287-1290.

Schultz, "New Catalysts for the Oxidation of Sulfides to Sulfones with Hydrogen Peroxide", Journal of Org. Chem. (1963), vol. 28, 1140-1142.

Kazuta, et al. Cyclopropane-Based Conformational Restriction of Histamine (1S,2S)-2-(2-Aminoethyl)-1-(1H-imidazol-4-yl) cyclopropane,aHighlySelective Agonist for the Histamine H3 Receptor, Having a cis-Cyclopropane Structure, Journal of Med. Chem. vol. 46, (2003) pp. 1980-1988.

Takai, et al. "Simple and Selective Method for RCHO—(E)-RCH=CHX Conversion by Means of a CHX3-CrCI2 System", Journal of American Chem Soc., pp. 7408-7410, (1986).

Marconi, et al., Nanostructuredrutheniumonc Al2O3 Catalysts for the Efficient Hydrogenation of Aromatic Compounds, Journal of Organometallic Chemistry, 689 (2004) pp. 639-646.

Wikler, et al., "Methods for Dilution Antimicrobial Susceptibility Tests for Bacteria That Grow Aerobically" Approved Standard—Seventh Edition, Clinical and Laboratory Standards Institute, vol. 26, No. 2, (2006).

* cited by examiner

CYCLOHEXYL OR PIPERIDINYL CARBOXAMIDE ANTIBIOTIC DERIVATIVES

CROSS-REFERENCE TO RELATED APPLICATIONS

This application is a national stage of PCT/IB2007/051002, filed on Mar. 22, 2007, which in turn claims priority to PCT/IB2006/050901, filed on Mar. 23, 2006, both of which applications are hereby incorporated by reference in their entirety.

BACKGROUND OF THE INVENTION

The present invention concerns novel antibiotics, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

BRIEF SUMMARY OF THE INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactam and quinolone antibiotics and now even to vancomycin;
- *S. pneumoniae* is becoming resistant to penicillin and quinolone antibiotics and even to new macrolides;
- Enteroccocci are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Further new emerging organisms like *Acinetobacter* spp., which have been selected during therapy with the currently used antibiotics, are becoming a real problem in hospital settings.

In addition, microorganisms that are causing persistent infections are increasingly being recognized as causative agents or cofactors of severe chronic diseases like peptic ulcers or heart diseases.

It has now been found that certain cyclohexyl or piperidinyl carboxamide derivatives are potent antimicrobial agents that are notably effective against a variety of multi-drug resistant bacteria. Thus, the present invention relates to the compounds of formula I

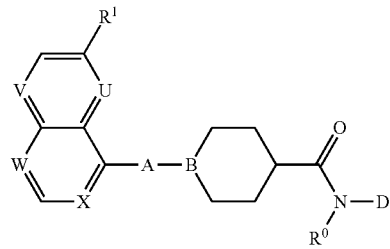

wherein
$R^0$ represents hydrogen or methyl;
$R^1$ represents hydrogen, halogen, $(C_1\text{-}C_4)$alkyl, $(C_1\text{-}C_4)$alkoxy, cyano or $COOR^2$, $R^2$ being $(C_1\text{-}C_4)$alkyl;
one or two of U, V, W and X represent(s) N and the remaining represent each CH, or, in the case of X, may also represent $CR^x$, $R^x$ being a halogen atom (and preferably a fluorine atom);
either B represents N and A represents $CH_2CH_2$ or $CH(OR^3)CH_2$, or B represents CH or $C(OR^4)$ and A represents $OCH_2$, $CH_2CH(OR^5)$, $CH(OR^6)CH_2$, $CH(OR^7)CH(OR^8)$, $CH\text{=}CH$ or $CH_2CH_2$;
each of $R^3$, $R^4$, $R^5$, $R^6$, $R^7$ and $R^8$ represents independently hydrogen, $SO_3H$, $PO_3H_2$, $CH_2OPO_3H_2$ or $COR^9$, $R^9$ being either $CH_2CH_2COOH$ or such that $R^9$—COOH is a naturally occurring amino acid or dimethylaminoglycine;
D represents styryl, heteroarylvinyl, binuclear heteroaryl or a phenyl group which is substituted once or twice in the meta and/or para position(s) by substituents each independently selected from the group consisting of halogen, alkyl of one to three carbon atoms, alkoxy of one to three carbon atoms, trifluoromethyl and trifluoromethoxy (and preferably each independently selected from the group consisting of halogen and alkyl of one to three carbon atoms);
and to salts of compounds of formula I.

DETAILED DESCRIPTION OF THE INVENTION

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group, containing from one to ten, preferably one to six, and in particular one to four carbon atoms. Representative examples of alkoxy groups include, but are not limited to, methyl, ethyl, propyl, iso-propyl, n-butyl, iso-butyl, sec-butyl, tert-butyl or n-hexyl. The term "$(C_1\text{-}C_x)$alkyl" refers to a straight or branched chain alkyl group containing 1 to x carbon atoms.

The term "alkoxy", used alone or in combination, refers to a saturated straight or branched chain alkoxy group, containing from one to ten, preferably one to six, and in particular one to four carbon atoms. Representative examples of alkoxy groups include, but are not limited to, methoxy, ethoxy, propoxy, iso-propoxy, n-butoxy, iso-butoxy, sec-butoxy, tert-butoxy or n-hexyloxy. The term "$(C_1\text{-}C_x)$alkoxy" refers to a straight or branched chain alkoxy group containing 1 to x carbon atoms.

The term "halogen" refers to fluorine, chlorine, bromine or iodine, preferably to fluorine or chlorine.

The term "styryl" refers to a vinyl group, which is substituted on the terminal carbon atom by a phenyl ring. The phenyl ring of a styryl group may be unsubstituted or substituted one to three times (and notably one to two times) by atoms selected from halogen atoms.

The term "heteroarylvinyl" refers to a vinyl group wherein the terminal hydrogen atom has been replaced by a heteroaryl group. The term "heteroaryl" means a 5- or 6-membered aromatic heterocyclic ring containing 1 to 3 heteroatoms each selected independently from O, N and S. A heteroaryl ring may be substituted once or twice (preferably once) by groups selected independently from halogen atoms. Representative examples of heteroaryl include, but are not limited to, pyridyl, imidazolyl, pyrazolyl, pyrrolyl, oxazolyl, isoxazolyl, thienyl, thiazolyl, isothiazolyl, 1,2,3-triazolyl, 1,2,4-triazolyl, oxadiazolyl, thiadiazolyl, tetrazolyl, pyrazinyl, pyrimidinyl and pyridazinyl groups.

The term "binuclear heteroaryl" refers to an aromatic bicyclic group, having nine or ten ring-atoms wherein one to three of these ring atoms are heteroatoms each selected independently from O, N and S and the others are all carbon atoms. The term "binuclear heteroaryl" also covers bicyclic structures selected from the group consisting of benzo[1,3]dioxol-5-yl, 2,3-dihydro-benzo[1,4]dioxin-6-yl, 2,3-dihydro-benzo[1,4]dithiin-6-yl, 2,3-dihydro-[1,4]dioxino[2,3-b]pyridin-6-yl, 2,3-dihydro-[1,4]dioxino[2,3-c]pyridin-7-yl, 3-oxo-3,4-dihydro-2H-benzo[1,4]thiazin-6-yl, 3-oxo-3,4-dihydro-2H-benzo[1,4]oxazin-6-yl, 3-oxo-3,4-dihydro-2H-pyrido[3,2-b][1,4]thiazin-6-yl, 3-oxo-3,4-dihydro-2H-pyrido[3,2-b][1,4]oxazin-6-yl, 2-oxo-3,4-dihydro-1H-quinolin-7-yl, and chroman-7-yl. Any binuclear heteroaryl group as defined herein may be substituted with one or two substituents on its aromatic ring(s), said substituents being each selected independently from the group consisting of halogen atoms. Hence, examples of binuclear heteroaryl groups include, but are not limited to, benzo[1,3]dioxol-5-yl, 2,3-dihydro-benzo[1,4]dioxin-6-yl, 2,3-dihydro-benzo[1,4]dithiin-6-yl, 2,3-dihydro-[1,4]dioxino[2,3-b]pyridin-6-yl, 2,3-dihydro-[1,4]dioxino[2,3-c]pyridin-7-yl, 3-oxo-3,4-dihydro-2H-benzo[1,4]thiazin-6-yl, 7-fluoro-3-oxo-3,4-dihydro-2H-benzo[1,4]thiazin-6-yl, 3-oxo-3,4-dihydro-2H-benzo[1,4]oxazin-6-yl, 3-oxo-3,4-dihydro-2H-pyrido[3,2-b][1,4]thiazin-6-yl, 3-oxo-3,4-dihydro-2H-pyrido[3,2-b][1,4]oxazin-6-yl, 2-oxo-3,4-dihydro-1H-quinolin-7-yl, benzo[1,2,5]thiadiazol-5-yl, 2,2-dimethyl-chroman-7-yl, benzofuran-3-yl, benzothiazol-6-yl and benzooxazol-6-yl (and in particular benzo[1,3]dioxol-5-yl, 2,3-dihydro-benzo[1,4]dioxin-6-yl, 2,3-dihydro-benzo[1,4]dithiin-6-yl, 2,3-dihydro-[1,4]dioxino[2,3-b]pyridin-6-yl, 2,3-dihydro-[1,4]dioxino[2,3-c]pyridin-7-yl, 3-oxo-3,4-dihydro-2H-benzo[1,4]thiazin-6-yl, 7-fluoro-3-oxo-3,4-dihydro-2H-benzo[1,4]thiazin-6-yl, 3-oxo-3,4-dihydro-2H-benzo[1,4]oxazin-6-yl, 3-oxo-3,4-dihydro-2H-pyrido[3,2-b][1,4]thiazin-6-yl, 3-oxo-3,4-dihydro-2H-pyrido[3,2-b][1,4]oxazin-6-yl, 2-oxo-3,4-dihydro-1H-quinolin-7-yl, benzo[1,2,5]thiadiazol-5-yl, 2,2-dimethyl-chroman-7-yl and benzofuran-3-yl).

In this patent application, a bond interrupted by a wavy line shows the point of attachment of the radical drawn. For example, the radical drawn below

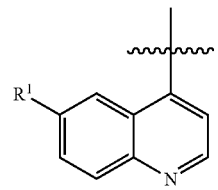

wherein $R^1$ represents methoxy is the 6-methoxy-quinolin-4-yl group.

When in the formula

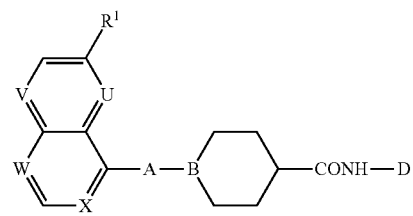

A represents the radical $CH(OR^3)CH_2$, this means specifically that the $CH(OR^3)$ part of the $CH(OR^3)CH_2$ radical is attached to the bicyclic heteroaromatic group and that the $CH_2$ part of the $CH(OR^3)CH_2$ radical is attached to B. This is applicable mutatis mutandis to all radicals that make the A radical and also to the formula

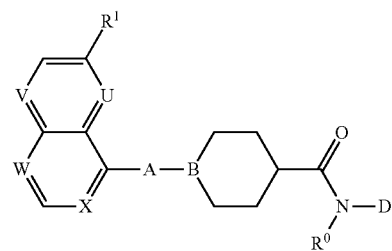

In other words, in the radicals of the formulae of this patent application, the left part of a radical is always attached to the right part of the radical that is next to the left.

Besides, the term "room temperature" as used herein refers to a temperature of 20° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

A particular embodiment of this invention relates to compounds of formula $I_P$

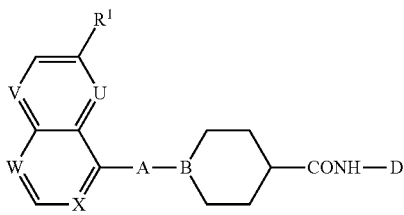

wherein
$R^1$ represents hydrogen, halogen, $(C_1-C_4)$alkyl, $(C_1-C_4)$ alkoxy, cyano or $COOR^2$, $R^2$ being $(C_1-C_4)$alkyl;
one or two of U, V, W and X represent(s) N and the remaining represent each CH, or, in the case of X, may also represent $CR^x$, $R^x$ being a halogen atom (and preferably a fluorine atom);
either B represents N and A represents $CH_2CH_2$ or $CH(OR^3)CH_2$, or B represents CH or $C(OR^4)$ and A represents $OCH_2$, $CH_2CH(OR^5)$, $CH(OR^6)CH_2$, $CH(OR^7)CH(OR^8)$, $CH=CH$ or $CH_2CH_2$;
each of $R^3$, $R^4$, $R^5$, $R^6$, $R^7$ and $R^8$ represents independently hydrogen, $SO_3H$, $PO_3H_2$, $CH_2OPO_3H_2$ or $COR^9$, $R^9$ being either $CH_2CH_2COOH$ or such that $R^9$—COOH is a naturally occurring amino acid or dimethylaminoglycine;
D represents styryl, heteroarylvinyl or binuclear heteroaryl;
and to salts of compounds of formula $I_P$.

In particular, the invention relates to compounds of formula I that are also compounds of formula $I_{CE}$ $I_{CE}$ wherein
$R^0$ represents hydrogen or methyl;
$R^1$ represents hydrogen, $(C_1-C_4)$alkoxy, cyano or $COOR^2$, $R^2$ being $(C_1-C_4)$alkyl ($R^1$ representing preferably methoxy, cyano or $COOCH_3$);
one or two of U, V, W and X represent(s) N and the remaining represent each CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$ or $CH_2CH_2$;
D represents 2,3-dihydro-benzo[1,4]dioxin-6-yl, 3-oxo-3,4-dihydro-2H-benzo[1,4]thiazin-6-yl, 3-oxo-3,4-dihydro-2H-benzo[1,4]oxazin-6-yl, benzothiazol-6-yl, a styryl group substituted one or two times by halogen atoms on the aromatic ring or a phenyl group substituted once or twice in the meta and/or para position(s) by substituents each independently selected from the group consisting of halogen and alkyl of one to three carbon atoms;
and to salts of compounds of formula $I_{CE}$.

More particularly, the invention relates to compounds of formula I that are also compounds of formula $I_{CEP}$

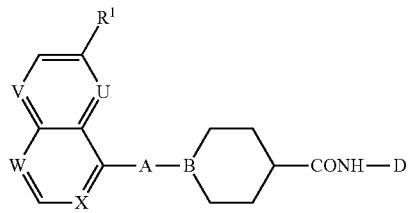

wherein
$R^1$ represents hydrogen, $(C_1-C_4)$alkoxy, cyano or $COOR^2$, $R^2$ being $(C_1-C_4)$alkyl ($R^1$ representing preferably methoxy, cyano or $COOCH_3$);
one or two of U, V, W and X represent(s) N and the remaining represent each CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$ or $CH_2CH_2$;
D represents 2,3-dihydro-benzo[1,4]dioxin-6-yl, 3-oxo-3,4-dihydro-2H-benzo[1,4]thiazin-6-yl, 3-oxo-3,4-dihydro-2H-benzo[1,4]oxazin-6-yl or a styryl group substituted one or two times by halogen atoms on the aromatic ring;
and to salts of compounds of formula $I_{CE}$.

A particular embodiment of this invention relates to compounds of formula I that are such that they also correspond to formula $I_D$ $I_D$ wherein
$R^0$ represents hydrogen or methyl;
$R^1$ represents hydrogen, halogen, $(C_1-C_4)$alkyl, $(C_1-C_4)$ alkoxy, cyano or $COOR^2$, $R^2$ being $(C_1-C_4)$alkyl;
one or two of U, V, W and X represent(s) N and the remaining represent each CH, or, in the case of X, may also represent $CR^x$, $R^x$ being a halogen atom (and preferably a fluorine atom);
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
D represents styryl, heteroarylvinyl, binuclear heteroaryl or a phenyl group which is substituted once or twice in the meta and/or para position(s) by substituents each independently selected from the group consisting of halogen, alkyl of one to three carbon atoms, alkoxy of one to three carbon atoms, trifluoromethyl and trifluoromethoxy;
and to salts of compounds of formula $I_D$.

A further particular embodiment of this invention relates to compounds of formula $I_P$ that are such that they also correspond to formula $I_{DP}$ $$\text{[structure } I_{DP}\text{]}$$

wherein
- $R^1$ represents hydrogen, halogen, $(C_1\text{-}C_4)$alkyl, $(C_1\text{-}C_4)$alkoxy, cyano or $COOR^2$, $R^2$ being $(C_1\text{-}C_4)$alkyl;
- one or two of U, V, W and X represent(s) N and the remaining represent each CH, or, in the case of X, may also represent $CR^x$, $R^x$ being a halogen atom (and preferably a fluorine atom);
- either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
- D represents styryl, heteroarylvinyl or binuclear heteroaryl;

and to salts of compounds of formula $I_D$.

Preferred compounds of formula I are those wherein at least one of the following characteristics is present:
- $R^1$ represents hydrogen, fluorine, $(C_1\text{-}C_3)$alkoxy, cyano or $COOR^2$, $R^2$ being methyl or ethyl;
- W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
- either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
- D represents a styryl group wherein the phenyl group is substituted one or two times by fluorine atoms, or
- D represents a binuclear heteroaryl group of formula $$\text{[structure with P]}$$

wherein P is a ring selected from the following $$\text{[six ring structures]}$$

wherein
- Q is O or S,
- Q' is O or S, and
- Q" is O or S, or also
- D represents a phenyl group which is substituted once or twice in the meta and/or para position(s) by substituents each independently selected from the group consisting of halogen, alkyl of one to three carbon atoms, alkoxy of one to three carbon atoms, trifluoromethyl and trifluoromethoxy.

More preferred compounds of formula I are those wherein at least one of the following further characteristics is present:
- $R^1$ represents hydrogen, $(C_1\text{-}C_3)$alkoxy, cyano or $COOR^2$, $R^2$ being methyl or ethyl;
- D represents a styryl group wherein the phenyl group is substituted by two fluorine atoms, or
- D represents a binuclear heteroaryl group of formula $$\text{[structure with P]}$$

wherein P is a ring selected from $$\text{[three ring structures]}$$

wherein
- Q is O; and
- Q' is O or S. or
- D represents a phenyl group which is substituted once or twice in the meta and/or para position(s) by substituents each independently selected from the group consisting of halogen and alkyl of one to three carbon atoms.

Particularly preferred compounds of formula I are those wherein at least one of the following further characteristics is present:

$R^1$ represents ($C_1$-$C_2$)alkoxy (in particular methoxy);

either B represents N and A represents $CH_2CH_2$ or CH(OH)$CH_2$, or B represents CH or C(OH) and A represents $OCH_2$, $CH_2$CH(OH), CH(OH)$CH_2$, CH(OH)CH(OH), CH=CH or $CH_2CH_2$;

D represents 2-(2,5-difluoro-phenyl)-vinyl, 2,3-dihydrobenzo[1,4]dioxin-6-yl, 3-oxo-3,4-dihydro-2H-benzo[1,4]thiazin-6-yl, 3-oxo-3,4-dihydro-2H-benzo[1,4]oxazin-6-yl, 4-ethyl-phenyl or 3-fluoro-4-methyl-phenyl (and notably 2-(2,5-difluoro-phenyl)-vinyl, 3,4-dihydro-2H-benzo[1,4]thiazin-6-yl or 3-oxo-3,4-dihydro-2H-benzo[1,4]oxazin-6-yl).

Preferred compounds of formula $I_P$ are those wherein at least one of the following characteristics is present:

$R^1$ represents hydrogen, fluorine, ($C_1$-$C_3$)alkoxy, cyano or $COOR^2$, $R^2$ being methyl or ethyl;

W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;

either B represents N and A represents $CH_2CH_2$ or CH(OH)$CH_2$, or B represents CH or C(OH) and A represents $OCH_2$, $CH_2$CH(OH), CH(OH)$CH_2$, CH(OH)CH(OH), CH=CH or $CH_2CH_2$;

D represents a styryl group wherein the phenyl group is substituted one or two times by fluorine atoms, or D represents a binuclear heteroaryl group of formula

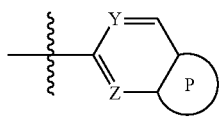

wherein
Y and Z are each independently N or $CR^{10}$;
$R^{10}$ is hydrogen or halogen (in particular hydrogen or fluorine and notably hydrogen); and
P is a ring selected from the following

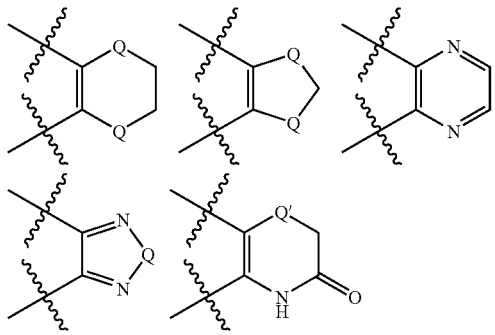

wherein
Q is O or S; and
Q' is O or S.

More preferred compounds of formula $I_P$ are those wherein at least one of the following further characteristics is present:

$R^1$ represents hydrogen, ($C_1$-$C_3$)alkoxy, cyano or $COOR^2$, $R^2$ being methyl or ethyl;

D represents a styryl group wherein the phenyl group is substituted by two fluorine atoms, or D represents a binuclear heteroaryl group of formula

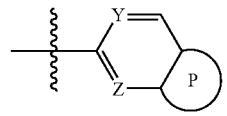

wherein
Y and Z are each independently N or $CR^{10}$;
$R^{10}$ is hydrogen or halogen (in particular hydrogen or fluorine and notably hydrogen); and
P is a ring selected from

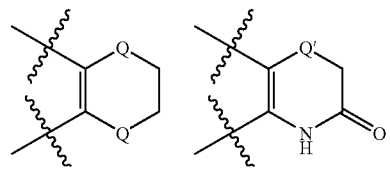

wherein
Q is O; and
Q' is O or S.

Particularly preferred compounds of formula $I_P$ are those wherein at least one of the following further characteristics is present:

$R^1$ represents ($C_1$-$C_2$)alkoxy (in particular methoxy);

either B represents N and A represents $CH_2CH_2$ or CH(OH)$CH_2$, or B represents CH or C(OH) and A represents $OCH_2$, $CH_2$CH(OH), CH(OH)$CH_2$, CH(OH)CH(OH), CH=CH or $CH_2CH_2$;

D represents 2-(2,5-difluoro-phenyl)-vinyl, 2,3-dihydrobenzo[1,4]dioxin-6-yl, 3-oxo-3,4-dihydro-2H-benzo[1,4]thiazin-6-yl or 3-oxo-3,4-dihydro-2H-benzo[1,4]oxazin-6-yl (and notably 2-(2,5-difluoro-phenyl)-vinyl or 3,4-dihydro-2H-benzo[1,4]thiazin-6-yl).

Preferred combinations for the symbols U, V, W and X in the compounds of formula I, $I_P$, $I_{CE}$, $I_{CEP}$, $I_D$ or $I_{DP}$ are evident from the following particular structures:

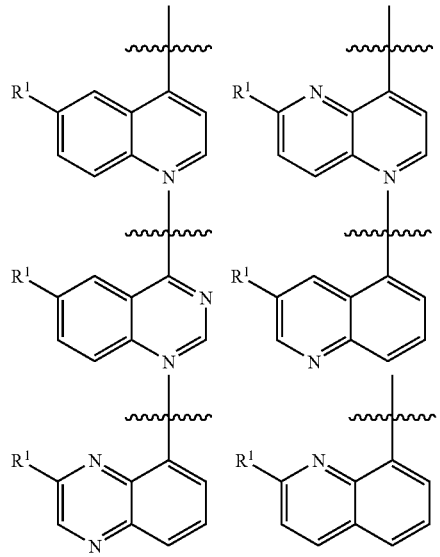

wherein $R^1$ is as defined in formula $I_P$, $I_{CE}$, $I_{CEP}$, $I_D$ or $I_{DP}$ respectively, and preferably ($C_1$-$C_3$)alkoxy (in particular ($C_1$-$C_2$)alkoxy and notably methoxy).

Particularly preferred meanings for D in the compounds of formula I are 2-(2,5-difluoro-phenyl)-vinyl, 2,3-dihydro-benzo[1,4]dioxin-6-yl, 3-oxo-3,4-dihydro-2H-benzo[1,4]thiazin-6-yl, 3-oxo-3,4-dihydro-2H-benzo[1,4]oxazin-6-yl, 4-ethyl-phenyl and 3-fluoro-4-methyl-phenyl.

Particularly preferred meanings for D in the compounds of formula $I_P$ are 2-(2,5-difluoro-phenyl)-vinyl, 2,3-dihydro-benzo[1,4]dioxin-6-yl, 3-oxo-3,4-dihydro-2H-benzo[1,4]thiazin-6-yl and 3-oxo-3,4-dihydro-2H-benzo[1,4]oxazin-6-yl.

According to a first variant of this invention, the compounds of formula I will be such that D is a styryl group optionally substituted one or two times by halogen atoms. The compounds according to this variant will be referred to hereafter as "compounds of formula $I_{ST}$". In addition, compounds of formula $I_P$ wherein D is a styryl group, a particular case of said first variant, will be referred to hereafter as "compounds of formula $I_{STP}$"

Preferred compounds of formula $I_{ST}$ are those wherein at least one of the following characteristics is present:

$R^0$ represents hydrogen;
$R^1$ represents ($C_1$-$C_3$)alkoxy (and notably methoxy);
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
D represents a styryl group wherein the phenyl group is substituted one or two times by fluorine atoms (and preferably the 2-(2,5-difluoro-phenyl)-vinyl group).

Preferred compounds of formula $I_{STP}$ are those wherein at least one of the following characteristics is present:

$R^1$ represents ($C_1$-$C_3$)alkoxy (and notably methoxy);
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
D represents a styryl group wherein the phenyl group is substituted one or two times by fluorine atoms (and preferably the 2-(2,5-difluoro-phenyl)-vinyl group).

According to a second variant of this invention, the compounds of formula I will be such that D is a heteroarylvinyl group. The compounds according to this variant will be referred to hereafter as "compounds of formula $I_{HET}$". In addition, compounds of formula $I_P$ wherein D is a heteroarylvinyl group, a particular case of said second variant, will be referred to hereafter as "compounds of formula $I_{HETP}$".

Preferred compounds of formula $I_{HET}$ are those wherein at least one of the following characteristics is present:

$R^0$ represents hydrogen;
$R^1$ represents ($C_1$-$C_3$)alkoxy (and notably methoxy);
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
D is 2-thiazolyl or 2-thienyl.

Preferred compounds of formula $I_{HETP}$ are those wherein at least one of the following characteristics is present:

$R^1$ represents ($C_1$-$C_3$)alkoxy (and notably methoxy);
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
D is 2-thiazolyl or 2-thienyl.

According to a third variant of this invention, the compounds of formula I will be such that D is a binuclear heteroaryl group. The compounds according to this variant will be referred to hereafter as "compounds of formula $I_{BH}$". In addition, compounds of formula $I_P$ wherein D is a binuclear heteroaryl group, a particular case of said third variant, will be referred to hereafter as "compounds of formula $I_{BHP}$".

Preferred compounds of formula $I_{BH}$ are those wherein at least one of the following characteristics is present:

$R^0$ represents hydrogen;
$R^1$ represents hydrogen, ($C_1$-$C_3$)alkoxy, cyano or $COOR^2$, $R^2$ being ($C_1$-$C_4$)alkyl;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
D represents a binuclear heteroaryl group of formula

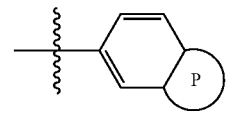

wherein
P is a ring selected from the following

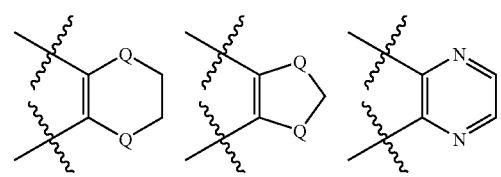

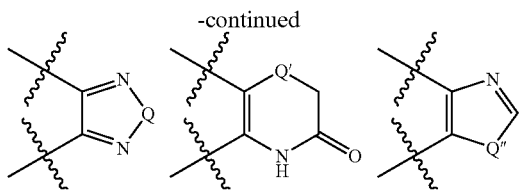

wherein
Q is O or S,
Q' is O or S, and
Q" is O or S.

Preferred compounds of formula $I_{BHP}$ are those wherein at least one of the following characteristics is present:

$R^1$ represents hydrogen, $(C_1-C_3)$alkoxy, cyano or $COOR^2$, $R^2$ being $(C_1-C_4)$alkyl;

W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;

either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;

D represents a binuclear heteroaryl group of formula

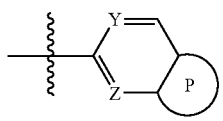

wherein
Y and Z are each independently N or $CR^{10}$;
$R^{10}$ is hydrogen or halogen (in particular hydrogen or fluorine and notably hydrogen); and
P is a ring selected from the following

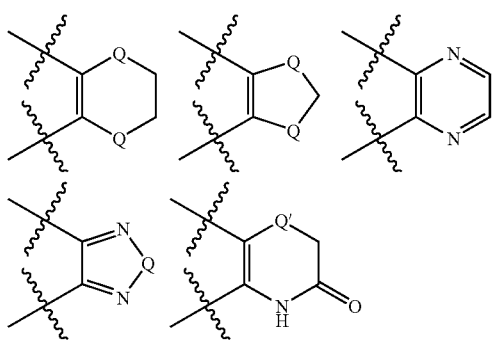

wherein
Q is O or S; and
Q' is O or S.

More preferred compounds of formula $I_{BH}$ are those wherein at least one of the following further characteristics is present:

$R^0$ represents hydrogen;
$R^1$ represents $(C_1-C_3)$alkoxy (and preferably methoxy);
D represents a binuclear heteroaryl group of formula

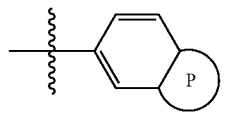

wherein
P is a ring selected from the following

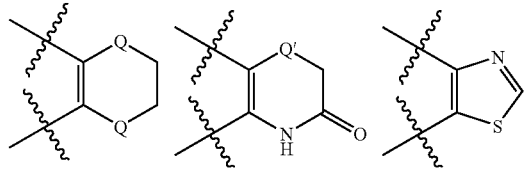

wherein
Q is O; and
Q' is O or S.

More preferred compounds of formula $I_{BHP}$ are those wherein at least one of the following further characteristics is present:

$R^1$ represents $(C_1-C_3)$alkoxy (and preferably methoxy);
D represents a binuclear heteroaryl group of formula

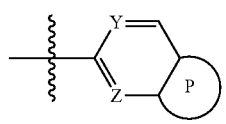

wherein
Y and Z are each independently N or CH; and
P is a ring selected from the following

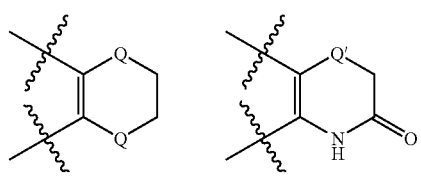

wherein
Q is O; and
Q' is O or S.

Particularly preferred compounds of formula $I_{BH}$ are those wherein $R^0$ represents hydrogen and D is 2,3-dihydro-benzo[1,4]dioxin-6-yl, 3-oxo-3,4-dihydro-2H-benzo[1,4]thiazin-6-yl, 3-oxo-3,4-dihydro-2H-benzo[1,4]oxazin-6-yl, benzoxazol-6-yl or benzothiazol-6-yl (and notably 3-oxo-3,4-dihydro-2H-benzo[1,4]thiazin-6-yl).

Particularly preferred compounds of formula $I_{BHP}$ are those wherein D is 2,3-dihydro-benzo[1,4]dioxin-6-yl, 3-oxo-3,4-dihydro-2H-benzo[1,4]thiazin-6-yl or 3-oxo-3,4-dihydro-2H-benzo[1,4]oxazin-6-yl (and notably 3-oxo-3,4-dihydro-2H-benzo[1,4]thiazin-6-yl).

According to a fourth variant of this invention, the compounds of formula I will be such that B represents N. The compounds according to this variant will be referred to hereafter as "compounds of formula $I_N$". In addition, compounds of formula $I_P$ wherein B represents N, a particular case of said fourth variant, will be referred to hereafter as "compounds of formula $I_{NP}$".

Preferred compounds of formula $I_N$ are those wherein at least one of the following characteristics is present:

$R^0$ represents hydrogen;
$R^1$ represents $(C_1-C_3)$alkoxy;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
A represents $CH_2CH_2$ or $CH(OH)CH_2$;
D represents a styryl group wherein the phenyl group is substituted one or two times by fluorine atoms, or
D represents a binuclear heteroaryl group of formula

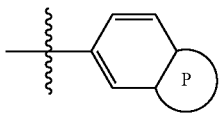

wherein P is a ring selected from the following

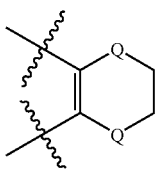 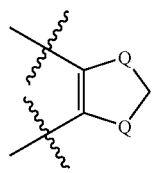

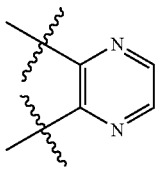 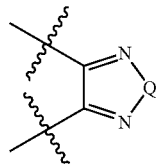

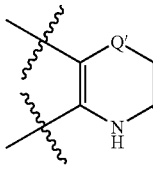 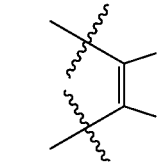

wherein
Q is O or S,
Q' is O or S,
Q" is O or S, or also
D represents a phenyl group which is substituted once or twice in the meta and/or para position(s) by substituents each independently selected from the group consisting of halogen and alkyl of one to three carbon atoms.

Preferred compounds of formula $I_{NP}$ are those wherein at least one of the following characteristics is present:

$R^1$ represents $(C_1-C_3)$alkoxy;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
A represents $CH_2CH_2$ or $CH(OH)CH_2$;

D represents a styryl group wherein the phenyl group is substituted one or two times by fluorine atoms, or D represents a binuclear heteroaryl group of formula

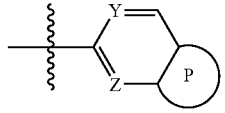

wherein
Y and Z are each independently N or $CR^{10}$;
$R^{10}$ is hydrogen or halogen (in particular hydrogen or fluorine and notably hydrogen); and
P is a ring selected from the following

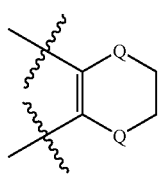 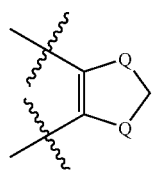

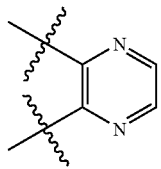 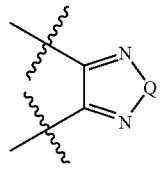

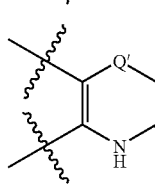

wherein
Q is O or S; and
Q' is O or S.

More preferred compounds of formula $I_N$ are those wherein at least one of the following further characteristics is present:

$R^0$ represents hydrogen;
$R^1$ represents methoxy;
U represents CH or N, V represents CH, W represents N and X represents CH;
D represents a styryl group wherein the phenyl group is substituted one or two times by fluorine atoms, or D represents a binuclear heteroaryl group of formula

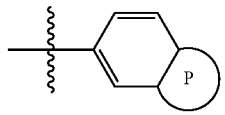

wherein P is a ring selected from the following

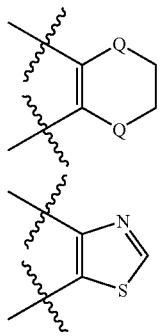
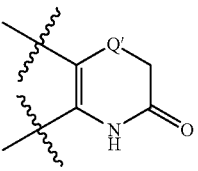

wherein
Q is O; and
Q' is O or S.

More preferred compounds of formula $I_{NP}$ are those wherein at least one of the following further characteristics is present:

$R^1$ represents methoxy;
U represents CH or N, V represents CH, W represents N and X represents CH;
D represents a styryl group wherein the phenyl group is substituted one or two times by fluorine atoms, or D represents a binuclear heteroaryl group of formula

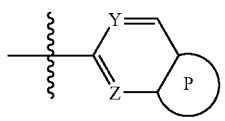

wherein
Y and Z are each independently N or CH; and
P is a ring selected from the following

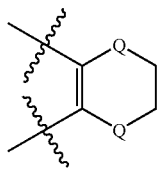

wherein
Q is O; and
Q' is O or S.

According to a fifth variant of this invention, the compounds of formula I will be such that B represents CH. The compounds according to this variant will be referred to hereafter as "compounds of formula $I_C$". In addition, compounds of formula $I_P$ wherein B represents CH, a particular case of said fifth variant, will be referred to hereafter as "compounds of formula $I_{CP}$".

Preferred compounds of formula $I_C$ are those wherein at least one of the following characteristics is present:

$R^0$ represents hydrogen;
$R^1$ represents $(C_1-C_3)$alkoxy, cyano or $COOR^2$, $R^2$ being methyl or ethyl;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
A represents $OCH_2$, $CH_2CH(OH)$, $CH(OH)CH_2$, $CH(OH)CH(OH)$ or $CH_2CH_2$;
D represents a styryl group wherein the phenyl group is substituted one or two times by fluorine atoms, or
D represents a binuclear heteroaryl group of formula

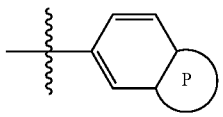

wherein
Y and Z are each independently N or $CR^{10}$;
$R^{10}$ is hydrogen or halogen (in particular hydrogen or fluorine and notably hydrogen); and
P is a ring selected from the following

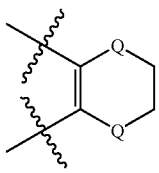 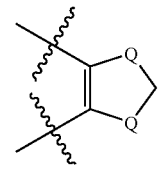
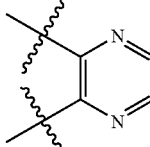 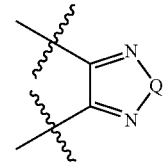
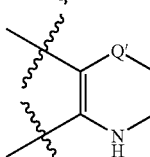 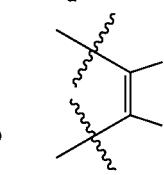

wherein
Q is O or S;
Q' is O or S, and
Q" is O or S, or also
D represents a phenyl group which is substituted once or twice in the meta and/or para position(s) by substituents each independently selected from the group consisting of halogen and alkyl of one to three carbon atoms.

Preferred compounds of formula $I_{CP}$ are those wherein at least one of the following characteristics is present:

$R^1$ represents $(C_1-C_3)$alkoxy, cyano or $COOR^2$, $R^2$ being methyl or ethyl;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
A represents $OCH_2$, $CH_2CH(OH)$, $CH(OH)CH_2$, $CH(OH)CH(OH)$ or $CH_2CH_2$;
D represents a styryl group wherein the phenyl group is substituted one or two times by fluorine atoms, or D represents a binuclear heteroaryl group of formula wherein
Y and Z are each independently N or CR$^{10}$;
R$^{10}$ is hydrogen or halogen (in particular hydrogen or fluorine and notably hydrogen); and
P is a ring selected from the following wherein
Q is O or S, and
Q' is O or S.

More preferred compounds of formula I$_C$ are those wherein at least one of the following characteristics is present:
R$^0$ represents hydrogen;
R$^1$ represents methoxy;
A represents OCH$_2$, CH$_2$CH(OH), CH(OH)CH$_2$, CH(OH)CH(OH) or CH$_2$CH$_2$;
D represents a styryl group wherein the phenyl group is substituted one or two times by fluorine atoms, or
D represents a binuclear heteroaryl group of formula wherein
P is a ring selected from the following wherein
Q is O, and
Q' is O or S.

More preferred compounds of formula I$_{CP}$ are those wherein at least one of the following characteristics is present:
R$^1$ represents methoxy;
A represents OCH$_2$, CH$_2$CH(OH), CH(OH)CH$_2$, CH(OH)CH(OH) or CH$_2$CH$_2$;
D represents a styryl group wherein the phenyl group is substituted one or two times by fluorine atoms, or D represents a binuclear heteroaryl group of formula wherein
Y and Z are each independently N or CH; and
P is a ring selected from the following wherein
Q is O; and
Q' is O or S.

According to a sixth variant of this invention, the compounds of formula I will be such that B represents C(OH). The compounds according to this variant will be referred to hereafter as "compounds of formula I$_{OH}$". In addition, compounds of formula I$_P$ wherein B represents C(OH), a particular case of said sixth variant, will be referred to hereafter as "compounds of formula I$_{OHP}$".

Preferred compounds of formula I$_{OH}$ are those wherein at least one of the following characteristics is present:
R$^0$ represents hydrogen;
R$^1$ represents (C$_1$-C$_3$)alkoxy;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are each CH;
A represents CH$_2$CH$_2$;
D represents a styryl group wherein the phenyl group is substituted one or two times by fluorine atoms, or D represents a binuclear heteroaryl group of formula

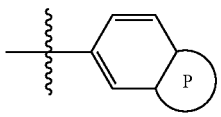

wherein P is a ring selected from the following

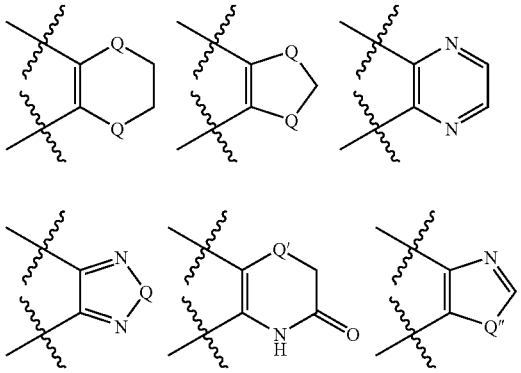

wherein
Q is O or S,
Q' is O or S, and
Q" is O or S, or also
D represents a phenyl group which is substituted once or twice in the meta and/or para position(s) by substituents each independently selected from the group consisting of halogen, alkyl of one to three carbon atoms, alkoxy of one to three carbon atoms, trifluoromethyl and trifluoromethoxy.

Preferred compounds of formula $I_{OHP}$ are those wherein at least one of the following characteristics is present:

$R^1$ represents $(C_1-C_3)$alkoxy;

W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;

A represents $CH_2CH_2$;

D represents a styryl group wherein the phenyl group is substituted one or two times by fluorine atoms, or D represents a binuclear heteroaryl group of formula

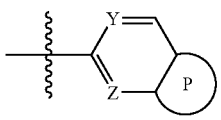

wherein
Y and Z are each independently N or $CR^{10}$;
$R^{10}$ is hydrogen or halogen (in particular hydrogen or fluorine and notably hydrogen); and P is a ring selected from the following

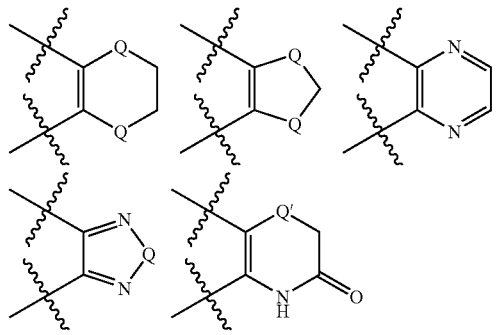

wherein
Q is O or S; and
Q' is O or S.

More preferred compounds of formula $I_{OH}$ are those wherein at least one of the following further characteristics is present:

$R^0$ represents hydrogen;
$R^1$ represents methoxy;
W is N and U, V and X are each CH, or U and W are each N and V and X are each CH, or also V is N and U, W and X are each CH;
D represents a styryl group wherein the phenyl group is substituted one or two times by fluorine atoms, or
D represents a binuclear heteroaryl group of formula

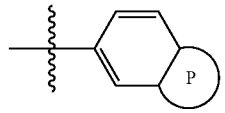

wherein
P is a ring selected from the following

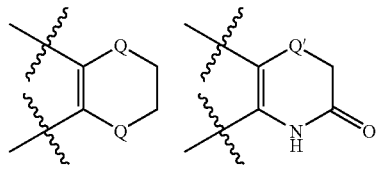

wherein
Q is O; and
Q' is O or S,
D represents a phenyl group which is substituted once or twice in the meta and/or para position(s) by substituents each independently selected from the group consisting of halogen and alkyl of one to three carbon atoms.

More preferred compounds of formula $I_{OHP}$ are those wherein at least one of the following further characteristics is present:

$R^1$ represents methoxy;
W is N and U, V and X are each CH, or U and W are each N and V and X are each CH, or also V is N and U, W and X are each CH;
D represents a styryl group wherein the phenyl group is substituted one or two times by fluorine atoms, or D represents a binuclear heteroaryl group of formula

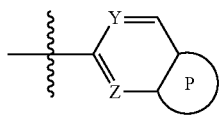

wherein
Y and Z are each independently N or CH, and
P is a ring selected from the following

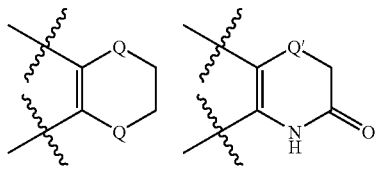

wherein
Q is O; and
Q' is O or S.

According to a seventh variant of this invention, the compounds of formula I will be such that D is a phenyl group which may be substituted once or twice by substituents each independently selected from the group consisting of halogen and alkyl of one to four carbon atoms. The compounds according to this variant will be referred to hereafter as "compounds of formula $I_{Ph}$".

Preferred compounds of formula $I_{Ph}$ are those wherein at least one of the following characteristics is present:

$R^1$ represents $(C_1-C_3)$alkoxy;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are each CH;
A represents $CH_2CH_2$;
D represents a phenyl group wherein the phenyl group is substituted in para position by an alkyl group and optionally in meta position by a further alkyl or a halogen (and notably 4-ethyl-phenyl or 3-fluoro-4-methyl-phenyl).

More preferred compounds of formula $I_{Ph}$ are those wherein at least one of the following further characteristics is present:

$R^0$ represents hydrogen;
$R^1$ represents methoxy;
W is N and U, V and X are each CH, or U and W are each N and V and X are each CH, or also V is N and U, W and X are each CH;
A represents $CH_2CH_2$;
D represents a phenyl group wherein the phenyl group is substituted in para position by an alkyl group or by halogen and in meta position by a further alkyl group or halogen, and in particular a phenyl group wherein the phenyl group is substituted in para position by an alkyl group and in meta position by a further alkyl or a halogen (and in particular 3-fluoro-4-methyl-phenyl).

According to an eighth variant of this invention, the compounds of formula I will be such that $R^0$ is hydrogen. The compounds according to this variant will be referred to hereafter as "compounds of formula $I_{HA}$".

Preferred compounds of formula $I_{HA}$ are those wherein at least one of the following characteristics is present:

$R^1$ represents hydrogen, fluorine, $(C_1-C_3)$alkoxy, cyano or $COOR^2$, $R^2$ being methyl or ethyl;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)$ $CH(OH)$, $CH=CH$ or $CH_2CH_2$;
D represents a styryl group wherein the phenyl group is substituted one or two times by fluorine atoms, or
D represents a binuclear heteroaryl group of formula

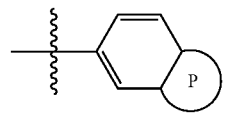

wherein P is a ring selected from the following

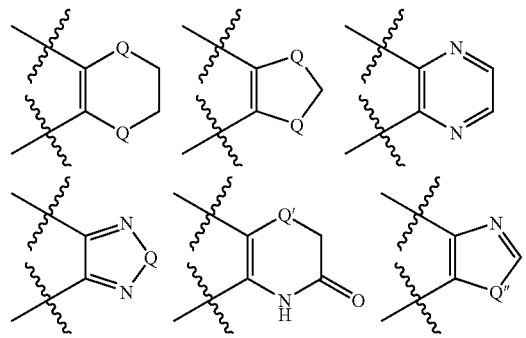

wherein
Q is O or S,
Q' is O or S, and
Q" is O or S, or also
D represents a phenyl group which is substituted once or twice in the meta and/or para position(s) by substituents each independently selected from the group consisting of halogen, alkyl of one to three carbon atoms, alkoxy of one to three carbon atoms, trifluoromethyl and trifluoromethoxy.

More preferred compounds of formula $I_{HA}$ are those wherein at least one of the following further characteristics is present:

$R^1$ represents hydrogen, $(C_1-C_3)$alkoxy, cyano or $COOR^2$, $R^2$ being methyl or ethyl (and notably $R^1$ representing $(C_1-C_3)$alkoxy, in particular methoxy);
D represents a styryl group wherein the phenyl group is substituted by two fluorine atoms, or
D represents a binuclear heteroaryl group of formula

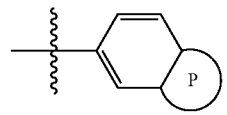

wherein P is a ring selected from

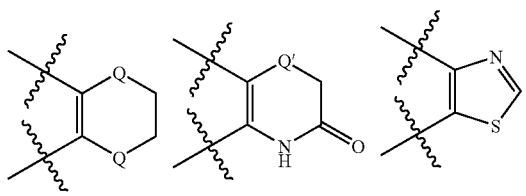

wherein
Q is O; and
Q' is O or S. or
D represents a phenyl group which is substituted once or twice in the meta and/or para position(s) by substituents each independently selected from the group consisting of halogen and alkyl of one to three carbon atoms.

According to a ninth variant of this invention, the compounds of formula I will be such that $R^0$ is methyl. The compounds according to this variant will be referred to hereafter as "compounds of formula $I_{MA}$".

Preferred compounds of formula $I_{MA}$ are those wherein at least one of the following characteristics is present:
$R^1$ represents hydrogen, fluorine, $(C_1-C_3)$alkoxy, cyano or $COOR^2$, $R^2$ being methyl or ethyl;
W is N and U, V and X are each CH, or U and W are each N and V and X are each CH, or W and X are each N and U and V are each CH, or V is N and U, W and X are each CH, or U and V are each N and W and X are each CH, or also U is N and V, W and X are CH;
either B represents N and A represents $CH_2CH_2$ or $CH(OH)CH_2$, or B represents CH or C(OH) and A represents $OCH_2$, $CH_2CH(OH)$, $CH(OH)CH_2$, $CH(OH)CH(OH)$, $CH=CH$ or $CH_2CH_2$;
D represents a styryl group wherein the phenyl group is substituted one or two times by fluorine atoms, or
D represents a binuclear heteroaryl group of formula

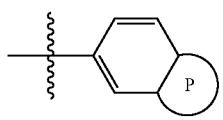

wherein P is a ring selected from the following

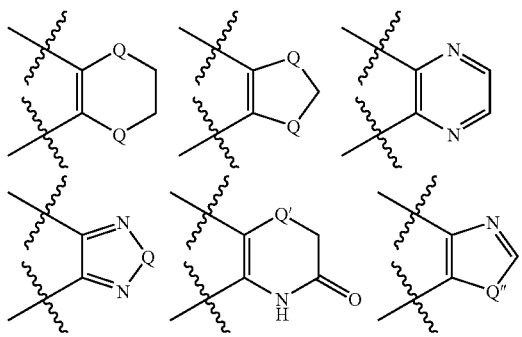

wherein
Q is O or S,
Q' is O or S, and
Q'' is O or S, or also

D represents a phenyl group which is substituted once or twice in the meta and/or para position(s) by substituents each independently selected from the group consisting of halogen, alkyl of one to three carbon atoms, alkoxy of one to three carbon atoms, trifluoromethyl and trifluoromethoxy.

More preferred compounds of formula $I_{MA}$ are those wherein at least one of the following further characteristics is present:
$R^1$ represents hydrogen, $(C_1-C_3)$alkoxy, cyano or $COOR^2$, $R^2$ being methyl or ethyl (and notably $R^1$ representing $(C_1-C_3)$alkoxy, in particular methoxy);
D represents a styryl group wherein the phenyl group is substituted by two fluorine atoms, or
D represents a binuclear heteroaryl group of formula

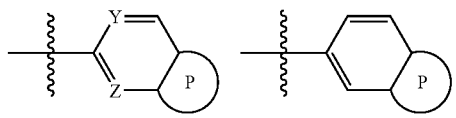

wherein P is a ring selected from

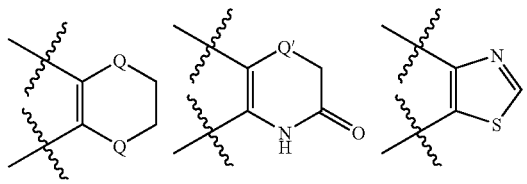

wherein
Q is O; and
Q' is O or S. or
D represents a phenyl group which is substituted once or twice in the meta and/or para position(s) by substituents each independently selected from the group consisting of halogen and alkyl of one to three carbon atoms.

Especially preferred are compounds of formula I or $I_P$ wherein the two substituents in positions 1 and 4 on the cyclohexyl ring are trans configured.

Besides, in compounds of formula I wherein B represents CH or C($OR^4$) and A represents $CH_2CH(OR^5)$ or $CH(OR^7)CH(OR^8)$, the stereochemistries will preferably be as depicted in structure Ia Ia

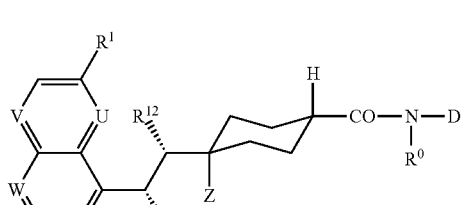

wherein Z represents hydrogen or $OR^4$;
$R^{11}$ represents H and $R^{12}$ represents $OR^5$ or $R^{11}$ represents $OR^7$ and $R^{12}$ represents $OR^8$; and
$R^0$, $R^1$, U, V, W, X, $R^4$, $R^5$, $R^7$, $R^8$ and D have the same meaning as in formula I.

Similarly, in compounds of formula I$_P$ wherein B represents CH or C(OR$^4$) and A represents CH$_2$CH(OR$^5$) or CH(OR$^7$)CH(OR$^8$), the stereochemistries will preferably be as depicted in structure Ia$_P$

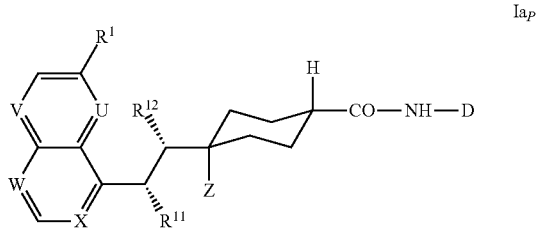

Ia$_P$ wherein Z represents hydrogen or OR$^4$;
R$^{11}$ represents H and R$^{12}$ represents OR$^5$ or R$^{11}$ represents OR$^7$ and R$^{12}$ represents OR$^8$; and
R$^1$, U, V, W, X, R$^4$, R$^5$, R$^7$, R$^8$ and D have the same meaning as in formula I$_P$.

Compounds of formula Ia as defined above and their salts (particularly their pharmaceutically acceptable salts), as well as compounds of formula Ia$_P$ as defined above and their salts (particularly their pharmaceutically acceptable salts), constitute further preferred embodiments of this invention.

Particularly preferred compounds of formula I are the following:

trans-4-(6-methoxy-quinolin-4-yloxymethyl)-cyclohexanecarboxylic acid (2,3-dihydro-benzo[1,4]dioxin-6-yl)-amide;
trans-4-(6-methoxy-quinazolin-4-yloxymethyl)-cyclohexanecarboxylic acid (2,3-dihydro-benzo[1,4]dioxin-6-yl)-amide;
trans-4-(6-methoxy-quinolin-4-yloxymethyl)-cyclohexanecarboxylic acid (3-oxo-3,4-dihydro-2H-benzo[1,4]thiazin-6-yl)-amide;
trans-4-(6-methoxy-quinazolin-4-yloxymethyl)-cyclohexanecarboxylic acid (3-oxo-3,4-dihydro-2H-benzo[1,4]thiazin-6-yl)-amide;
trans-4-[2-(6-methoxy-[1,5]naphthyridin-4-yl)-ethyl]-cyclohexanecarboxylic acid (2,3-dihydro-benzo[1,4]dioxin-6-yl)-amide;
trans-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
cis-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;
cis-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
trans-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;
trans-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
(2R)-1-[2-hydroxy-2-(6-methoxy-quinolin-4-yl)-ethyl]-piperidine-4-carboxylic acid (2,3-dihydro-benzo[1,4]dioxin-6-yl)-amide;
(2S)-1-[2-hydroxy-2-(6-methoxy-quinolin-4-yl)-ethyl]-piperidine-4-carboxylic acid (2,3-dihydro-benzo[1,4]dioxin-6-yl)-amide;
(2R)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;
(2S)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;
1-[2-(6-methoxy-quinolin-4-yl)-ethyl]-piperidine-4-carboxylic acid [2-(2,5-difluoro-phenyl)-vinyl]-amide;
trans-4-[(1R,2R)-1,2-dihydroxy-2-(3-methoxy-quinoxalin-5-yl)-ethyl]-cyclohexanecarboxylic acid (3-oxo-3,4-dihydro-2H-benzo[1,4]thiazin-6-yl)-amide;
trans-4-[(1R,2R)-1,2-dihydroxy-2-(6-methoxy-[1,5]naphthyridin-4-yl)-ethyl]-cyclohexanecarboxylic acid (2,3-dihydro-benzo[1,4]dioxin-6-yl)-amide;
trans-4-[(1R,2R)-1,2-dihydroxy-2-(3-methoxy-quinoxalin-5-yl)-ethyl]-cyclohexanecarboxylic acid (2,3-dihydro-benzo[1,4]dioxin-6-yl)-amide;
trans-4-[(1R,2R)-1,2-dihydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
trans-4-[(1S)-1-hydroxy-2-(6-methoxy-[1,5]naphthyridin-4-yl)-ethyl]-cyclohexanecarboxylic acid (2,3-dihydro-benzo[1,4]dioxin-6-yl)-amide;
trans-4-hydroxy-4-[2-(6-methoxy-quinolin-4-yl)-ethyl]-cyclohexanecarboxylic acid (2,3-dihydro-benzo[1,4]dioxin-6-yl)-amide;
trans-4-hydroxy-4-[2-(6-methoxy-quinolin-4-yl)-ethyl]-cyclohexanecarboxylic acid (3-oxo-3,4-dihydro-2H-benzo[1,4]thiazin-6-yl)-amide;
trans-4-hydroxy-4-[2-(6-methoxy-quinolin-4-yl)-ethyl]-cyclohexanecarboxylic acid (3-oxo-3,4-dihydro-2H-benzo[1,4]oxazin-6-yl)-amide;
trans-4-hydroxy-4-[2-(3-methoxy-quinolin-5-yl)-ethyl]-cyclohexanecarboxylic acid (2,3-dihydro-benzo[1,4]dioxin-6-yl)-amide;
trans-4-hydroxy-4-[2-(3-methoxy-quinolin-5-yl)-ethyl]-cyclohexanecarboxylic acid (3-oxo-3,4-dihydro-2H-benzo[1,4]thiazin-6-yl)-amide;
trans-4-hydroxy-4-[2-(3-methoxy-quinolin-5-yl)-ethyl]-cyclohexanecarboxylic acid (3-oxo-3,4-dihydro-2H-benzo[1,4]oxazin-6-yl)-amide;
trans-4-hydroxy-4-[2-(6-methoxy-quinolin-4-yl)-ethyl]-cyclohexanecarboxylic acid [2-(2,5-difluoro-phenyl)-vinyl]-amide;
trans-4-hydroxy-4-[2-(3-methoxy-quinolin-5-yl)-ethyl]-cyclohexanecarboxylic acid [2-(2,5-difluoro-phenyl)-vinyl]-amide;
1-[2-(6-methoxy-[1,5]naphthyridin-4-yl)-ethyl]-piperidine-4-carboxylic acid [2-(2,5-difluoro-phenyl)-vinyl]-amide;
trans-4-[4-(2,3-dihydro-benzo[1,4]dioxin-6-ylcarbamoyl)-cyclohexylmethoxy]-quinoline-6-carboxylic acid methyl ester;
trans-4-(6-cyano-quinolin-4-yloxymethyl)-cyclohexanecarboxylic acid (2,3-dihydro-benzo[1,4]dioxin-6-yl)-amide;
trans-4-(2-cyano-quinolin-8-yloxymethyl)-cyclohexanecarboxylic acid (2,3-dihydro-benzo[1,4]dioxin-6-yl)-amide;
trans-4-(quinolin-4-yloxymethyl)-cyclohexanecarboxylic acid (2,3-dihydro-benzo[1,4]dioxin-6-yl)-amide;
trans-4-[(E)-2-(6-methoxy-[1,5]naphthyridin-4-yl)-vinyl]-cyclohexanecarboxylic acid (2,3-dihydro-benzo[1,4]dioxin-6-yl)-amide;
trans-4-[(E)-2-(6-methoxy-[1,5]naphthyridin-4-yl)-vinyl]-cyclohexanecarboxylic acid (3-oxo-3,4-dihydro-2H-benzo[1,4]thiazin-6-yl)-amide;

trans-4-[2-hydroxy-2-(6-methoxy-[1,5]naphthyridin-4-yl)-ethyl]-cyclohexanecarboxylic acid (2,3-dihydro-benzo[1,4]dioxin-6-yl)-amide;

trans-4-[2-hydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

1-[2-hydroxy-2-(6-methoxy-quinolin-4-yl)-ethyl]-piperidine-4-carboxylic acid benzothiazol-6-ylamide;

4-hydroxy-4-[2-(6-methoxy-[1,5]naphthyridin-4-yl)-ethyl]-cyclohexanecarboxylic acid (3-fluoro-4-methyl-phenyl)-amide;

4-hydroxy-4-[2-(6-methoxy-[1,5]naphthyridin-4-yl)-ethyl]-cyclohexanecarboxylic acid (4-ethyl-phenyl)-amide;

4-hydroxy-4-[2-(6-methoxy-[1,5]naphthyridin-4-yl)-ethyl]-cyclohexanecarboxylic acid (2,3-dihydro-benzo[1,4]dioxin-6-yl)-methyl-amide;

and salts (in particular pharmaceutically acceptable salts) thereof.

Particularly preferred compounds of formula $I_P$ are the following:

trans-4-(6-methoxy-quinolin-4-yloxymethyl)-cyclohexanecarboxylic acid (2,3-dihydro-benzo[1,4]dioxin-6-yl)-amide;

trans-4-(6-methoxy-quinazolin-4-yloxymethyl)-cyclohexanecarboxylic acid (2,3-dihydro-benzo[1,4]dioxin-6-yl)-amide;

trans-4-(6-methoxy-quinolin-4-yloxymethyl)-cyclohexanecarboxylic acid (3-oxo-3,4-dihydro-2H-benzo[1,4]thiazin-6-yl)-amide;

trans-4-(6-methoxy-quinazolin-4-yloxymethyl)-cyclohexanecarboxylic acid (3-oxo-3,4-dihydro-2H-benzo[1,4]thiazin-6-yl)-amide;

trans-4-[2-(6-methoxy-[1,5]naphthyridin-4-yl)-ethyl]-cyclohexanecarboxylic acid (2,3-dihydro-benzo[1,4]dioxin-6-yl)-amide;

trans-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

cis-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;

cis-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

trans-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;

trans-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

(2R)-1-[2-hydroxy-2-(6-methoxy-quinolin-4-yl)-ethyl]-piperidine-4-carboxylic acid (2,3-dihydro-benzo[1,4]dioxin-6-yl)-amide;

(2S)-1-[2-hydroxy-2-(6-methoxy-quinolin-4-yl)-ethyl]-piperidine-4-carboxylic acid (2,3-dihydro-benzo[1,4]dioxin-6-yl)-amide;

(2R)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;

(2S)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;

1-[2-(6-methoxy-quinolin-4-yl)-ethyl]-piperidine-4-carboxylic acid [2-(2,5-difluoro-phenyl)-vinyl]-amide;

trans-4-[(1R,2R)-1,2-dihydroxy-2-(3-methoxy-quinoxalin-5-yl)-ethyl]-cyclohexanecarboxylic acid (3-oxo-3,4-dihydro-2H-benzo[1,4]thiazin-6-yl)-amide;

trans-4-[(1R,2R)-1,2-dihydroxy-2-(6-methoxy-[1,5]naphthyridin-4-yl)-ethyl]-cyclohexanecarboxylic acid (2,3-dihydro-benzo[1,4]dioxin-6-yl)-amide;

trans-4-[(1R,2R)-1,2-dihydroxy-2-(3-methoxy-quinoxalin-5-yl)-ethyl]-cyclohexanecarboxylic acid (2,3-dihydro-benzo[1,4]dioxin-6-yl)-amide;

trans-4-[(1R,2R)-1,2-dihydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

trans-4-[(1S)-1-hydroxy-2-(6-methoxy-[1,5]naphthyridin-4-yl)-ethyl]-cyclohexanecarboxylic acid (2,3-dihydro-benzo[1,4]dioxin-6-yl)-amide;

trans-4-hydroxy-4-[2-(6-methoxy-quinolin-4-yl)-ethyl]-cyclohexanecarboxylic acid (2,3-dihydro-benzo[1,4]dioxin-6-yl)-amide;

trans-4-hydroxy-4-[2-(6-methoxy-quinolin-4-yl)-ethyl]-cyclohexanecarboxylic acid (3-oxo-3,4-dihydro-2H-benzo[1,4]thiazin-6-yl)-amide;

trans-4-hydroxy-4-[2-(6-methoxy-quinolin-4-yl)-ethyl]-cyclohexanecarboxylic acid (3-oxo-3,4-dihydro-2H-benzo[1,4]oxazin-6-yl)-amide;

trans-4-hydroxy-4-[2-(3-methoxy-quinolin-5-yl)-ethyl]-cyclohexanecarboxylic acid (2,3-dihydro-benzo[1,4]dioxin-6-yl)-amide;

trans-4-hydroxy-4-[2-(3-methoxy-quinolin-5-yl)-ethyl]-cyclohexanecarboxylic acid (3-oxo-3,4-dihydro-2H-benzo[1,4]thiazin-6-yl)-amide;

trans-4-hydroxy-4-[2-(3-methoxy-quinolin-5-yl)-ethyl]-cyclohexanecarboxylic acid (3-oxo-3,4-dihydro-2H-benzo[1,4]oxazin-6-yl)-amide;

trans-4-hydroxy-4-[2-(6-methoxy-quinolin-4-yl)-ethyl]-cyclohexanecarboxylic acid [2-(2,5-difluoro-phenyl)-vinyl]-amide;

trans-4-hydroxy-4-[2-(3-methoxy-quinolin-5-yl)-ethyl]-cyclohexanecarboxylic acid [2-(2,5-difluoro-phenyl)-vinyl]-amide;

1-[2-(6-methoxy-[1,5]naphthyridin-4-yl)-ethyl]-piperidine-4-carboxylic acid [2-(2,5-difluoro-phenyl)-vinyl]-amide;

trans-4-[4-(2,3-dihydro-benzo[1,4]dioxin-6-ylcarbamoyl)-cyclohexylmethoxy]-quinoline-6-carboxylic acid methyl ester;

trans-4-(6-cyano-quinolin-4-yloxymethyl)-cyclohexanecarboxylic acid (2,3-dihydro-benzo[1,4]dioxin-6-yl)-amide;

trans-4-(2-cyano-quinolin-8-yloxymethyl)-cyclohexanecarboxylic acid (2,3-dihydro-benzo[1,4]dioxin-6-yl)-amide;

trans-4-(quinolin-4-yloxymethyl)-cyclohexanecarboxylic acid (2,3-dihydro-benzo[1,4]dioxin-6-yl)-amide;

and salts (in particular pharmaceutically acceptable salts) thereof.

Compounds of formula I are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes,* Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus,* coagulase-negative staphylococci (i.e., *S. epidermidis, S. haemolyticus,* etc.), *Streptococcus pyogenes, Streptococcus agalactiae,* Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus,* coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neisseria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae.*

Compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp., *Stenotrophomonas maltophilia, Neisseria meningitidis, Bacillus cereus, Bacillus anthracis, Corynebacterium* spp., *Propionibacterium acnes* and bacteroide spp.

Compounds of formula I according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula I according to this invention, or of a pharmaceutically acceptable salt thereof, for the manufacture of a medicament for the prevention or treatment of a bacterial infection.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

Examples of pharmacologically acceptable salts of sufficiently basic compounds of formula I are selected from the group consisting of salts of physiologically acceptable mineral acids like hydrochloric, hydrobromic, hydroiodic, sulfuric, sulfamic, nitric and phosphoric acid; or salts of organic acids like methanesulfonic, ethanedisulfonic, p-toluenesulfonic, lactic, acetic, trifluoroacetic, oxalic, benzoic, citric, succinic, fumaric, maleic, mandelic, cinnamic, pamoic, stearic, glutamic, aspartic and salicylic acid. Further, a sufficiently acidic compound of formula I may form alkali or earth alkaline metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts. For other examples of pharmaceutically acceptable salts, reference can be made notably to "Salt selection for basic drugs", *Int. J. Pharm.* (1986), 33, 201-217.

Compounds of general formula I containing at least one $R^3$, $R^4$, $R^5$, $R^6$, $R^7$ or $R^8$ group that is different from hydrogen will be referred to as "prodrugs" in this application. Such prodrugs and pharmaceutically acceptable salts thereof are also within the scope of this invention.

A pharmaceutical composition according to the present invention contains at least one compound of formula I (or a pharmaceutically acceptable salt thereof) as the active agent and optionally carriers and/or diluents and/or adjuvants, and may also contain additional known antibiotics. In particular, a pharmaceutical composition according to this invention will contain, as active principle, at least one compound of formula I (notably a compound of formula $I_{CE}$, $I_D$, $I_{ST}$, $I_{HET}$, $I_{BH}$, $I_N$, $I_C$, $I_{OH}$ or Ia), or a pharmaceutically acceptable salt of such a compound, and at least one pharmaceutically acceptable excipient.

As mentioned above, therapeutically useful agents that contain compounds of formula I, their salts and formulations thereof are also comprised in the scope of the present invention. In general, compounds of formula I will be administered by using the known and acceptable modes known in the art, either alone or in combination with any other therapeutic agent. Such therapeutically useful agents can be administered by one of the following routes: oral, e.g. as tablets, dragee, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystal or as a spray (e.g. liquid aerosol), transdermal, for example via an transdermal delivery system (TDS) such as a plaster containing the active ingredient, topical or intranasal. The substance of the present invention can also be used to impregnate or coated devices that are foreseen for implantation like catheters or artificial joints. The pharmaceutically useful agents may also contain additives for conservation, stabilisation, e.g. UV stabilizers, emulsifiers, sweetener, aromatisers, salts to change the osmotic pressure, buffers, coating additives and antioxidants.

Another aspect of the invention concerns a method for the prevention or the treatment of a bacterial infection in a patient comprising the administration to said patient of a pharmaceutically active amount of a compound of formula I (notably a compound of formula $I_{CE}$, $I_D$, $I_{ST}$, $I_{HET}$, $I_{BH}$, $I_N$, $I_C$, $I_{OH}$ or Ia) or of a pharmaceutically acceptable salt thereof.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_{CE}$, compounds of formula $I_D$, compounds of formula $I_{ST}$, compounds of formula $I_{HET}$, compounds of formula $I_{BH}$, compounds of formula $I_N$, compounds of formula $I_C$, compounds of formula $I_{OH}$ and compounds of formula Ia as well as to the salts thereof (notably the pharmaceutically acceptable salts thereof).

Moreover, the compounds of formula I which are not pro-drugs (i.e. those wherein $R^3$, $R^4$, $R^5$, $R^6$, $R^7$ and $R^8$, if occurring, represent each hydrogen), or the salts of such compounds, may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

Preparation of Compounds of Formula I

Abbreviations:

The following abbreviations are used throughout the specification and the examples:

| | |
|---|---|
| AcOH | acetic acid |
| AD-mix α | 1,4-bis(dihydroquinine)phthalazine, $K_3Fe(CN)_6$, $K_2CO_3$ and $K_2OsO_4 \cdot 2H_2O$ |
| AD-mix β | 1,4-bis(dihydroquinidine)phthalazine, $K_3Fe(CN)_6$, $K_2CO_3$ and $K_2OsO_4 \cdot 2H_2O$ |
| AIBN | 2,2'-azabisisobutyronitrile |
| aq. | aqueous |
| 9-BBN | 9-borabicyclo[3.3.1]nonane |
| $Boc_2O$ | di-tert-butyl dicarbonate |
| CSA | camphorsulfonic acid |
| DBU | 1,8-diazabicyclo[5.4.0]undec-7-ene |
| DBN | 1,5-diazabicyclo[4.3.0]non-5-ene |
| DCC | dicyclohexyl carbodiimide |
| 1,2-DCE | 1,2-dichloroethane |
| DCM | dichloromethane |
| DEAD | diethyl azo dicarboxylate |
| DIAD | diisopropyl azo dicarboxylate |
| DIBAH | diisobutylaluminium hydride |
| DIPEA | N,N-diisopropylethylamine |
| 1,2-DME | 1,2-dimethoxyethane |
| DMF | N,N-dimethylformamide |
| DMPU | 1,3-dimethyl-3,4,5,6-tetrahydro-2(1H)-pyrimidone |
| DMSO | dimethylsulfoxide |
| EA | ethyl acetate |
| EDC | 1-(3-dimethylaminopropyl)-3-ethylcarbodiimide hydrochloride |

-continued

| | |
|---|---|
| ESI | Electron Spray Ionisation |
| ether or $Et_2O$ | diethyl ether |
| EtOH | ethanol |
| h | hour(s) |
| HATU | O-(7-azabenzotriazol-1-yl)-N,N,N',N'-tetramethyluronium hexafluorophosphate |
| Hept | heptane |
| Hex | hexane |
| HOBT | 1-hydroxybenzotriazole hydrate |
| HPLC | high performance liquid chromatography |
| HV | high vacuum conditions |
| KHMDS | potassium hexamethyldisilazane |
| LiHMDS | lithium hexamethyldisilazane |
| MCPBA | meta-chloroperbenzoic acid |
| MeCN | acetonitrile |
| MeOH | methanol |
| min | minute(s) |
| MS | mass spectroscopy |
| MsCl | methanesulfonyl chloride |
| NBS | N-bromosuccinimide |
| n-BuLi | n-butyl lithium |
| NHS | N-hydroxysuccinimide |
| NMO | 4-methylmorpholine-N-oxide |
| org. | organic |
| OTf | triflate |
| Pd/C | palladium on charcoal |
| $Pd(dppf)Cl_2$ | 1,1'-bis(diphenylphosphino)ferrocene-palladium (II) dichloride |
| $PPh_3$ | triphenylphosphine |
| PTSA | para-toluenesulfonic acid |
| rt | room temperature |
| sat. | saturated |
| $SiO_2$ | silica gel |
| TBAF | tetrabutylammonium fluoride |
| TBDMSCl | tert-butyl-dimethyl-chlorosilane |
| TEA | triethylamine |
| TEMPO | 2,2,6,6-tetramethyl-1-piperidinyloxy |
| TFA | trifluoroacetic acid |
| THF | tetrahydrofuran |
| tlc | thin layer chromatography |
| TMS | trimethylsilyl |
| TPPA | tripropylphosphonic anhydride |
| TsCl | para-toluenesulfonyl chloride |

General Preparation Methods:

The compounds of formula I can be manufactured in accordance with the present invention by a) reacting a compound of the formula II

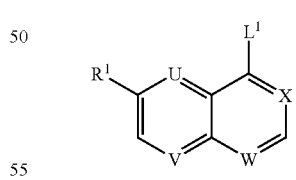

with a compound of the formula III

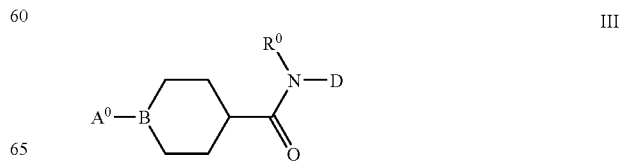

wherein $R^0$, $R^1$, U, V, W, X, B and D are as in formula I, $L^1$ is a reactive group, and $A^o$ is A that has been functionally modified to allow connection of the two moieties $L^1$ and $A^o$ of the compounds of formulae II and III to form A;

or b) reacting a compound of the formula IV

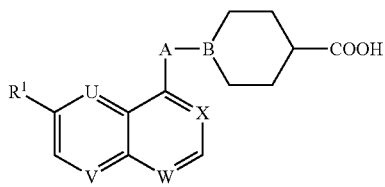

IV with a compound of the formula V $R^0$HN-D        V wherein A, B, $R^0$, $R^1$, U, V, W, X, D are as before, and where required, transforming groups A into other such groups;

or c) reacting a compound of the formula VI

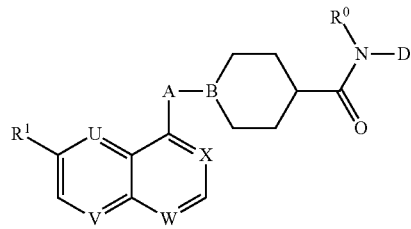

VI with a compound of the formula VII

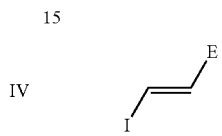

VII wherein E represents optionally substituted phenyl or heteroaryl and $R^0$, $R^1$, U, V, W, X, A, B and D are as before.

The compounds or formula I thus obtained may, if desired, be converted into their salts, and notably into their pharmaceutically acceptable salts.

Besides, whenever the compounds of formula I are obtained in the form of mixtures of enantiomers, the enantiomers can be separated using methods known to one skilled in the art (e.g. by formation and separation of diastereomeric salts or by chromatography over a chiral stationary phase). Whenever the compounds of formula I are obtained in the form of mixtures of diasteromers they may be separated by an appropriate combination of silica gel chromatography, HPLC and crystallization techniques.

In process alternative a) preferred reactive groups $L^1$ and $A^o$-B and resulting connections A-B, as the case may be, are evident from the following Table 1.

TABLE 1

| $L^1$ | $A^o$—B | A—B | Subsequent transformations |
|---|---|---|---|
| OH or halogen | HOCH$_2$—CH | OCH$_2$—CH | |
| Li or MgBr | HC(O)CH$_2$—CH | CH(OH)CH$_2$—CH | COCH$_2$—CH |
| Li or MgBr | CH$_3$N(OCH$_3$)COCH$_2$—CH | COCH$_2$—CH | CH(OH)CH$_2$—CH |
| Li or MgBr | CF$_3$SO$_2$O—CH$_2$CH$_2$—CH | CH$_2$CH$_2$—CH | |
| Li or MgBr | Hal-CH$_2$CH$_2$—CH (Hal = halogen) | CH$_2$CH$_2$—CH | |
| OSO$_2$CF$_3$ | HC≡C—CR$^m$ (R$^m$=H, OH) | C≡C—CR$^m$ | CH=CH—CR$^m$, CH$_2$CH$_2$—CR$^m$, CH(OH)CH(OH)—CR$^m$ CH(OH)CH$_2$—CR$^m$, CH$_2$CH(OH)—CR$^m$ |
| OSO$_2$CF$_3$ | (HO)$_2$B—CH$_2$CH$_2$—CH | CH$_2$CH$_2$—CH | |
| OSO$_2$CF$_3$ | H$_2$C=CH—CH | CH=CH—CH | CH$_2$CH$_2$—CH CH(OH)CH(OH)—CH CH(OH)CH$_2$—CH, CH$_2$CH(OH)—CH |
| CHO | Ph$_3$P=CH—CH | CH=CH—CH | CH$_2$CH$_2$—CH CH(OH)CH(OH)—CH CH(OH)CH$_2$—CH, CH$_2$CH(OH)—CH |

TABLE 1-continued

| L¹ | A°—B | A—B | Subsequent transformations |
|---|---|---|---|
| CHO | $(OR'')_2(O)PCH_2$—CH ($R''$ = alkyl) | CH=CH—CH | $CH_2CH_2$—CH<br>CH(OH)CH(OH)—CH<br>$CH(OH)CH_2$—CH,<br>$CH_2CH(OH)$—CH |
| CHO | $R^pSO_2CH_2$—CH<br>$R^p$ = aryl, heteroaryl | CH=CH—CH | $CH_2CH_2$—CH<br>CH(OH)CH(OH)—CH<br>$CH(OH)CH_2$—CH,<br>$CH_2CH(OH)$—CH |
| oxirane | NH | $CH(OH)CH_2$—N | |
| C≡CH | O=C | C≡C—C(OH) | CH=CH—C(OH)<br>$CH_2CH_2$—C(OH)<br>CH(OH)CH(OH)C(OH)<br>$CH_2CH(OH)C(OH)$ |
| $COCH_3$ | O=C | $C(=O)CH_2C(OH)$ | $CH(OH)CH_2C(OH)$ |

In process alternative c) the reaction is performed under palladium-catalyzed Buchwald-Hartwig conditions (*J. Am. Chem. Soc.* (1996), 118, 10333) or copper-catalyzed conditions (*J. Am. Chem. Soc.* (2002), 124, 7421). Various palladium sources and ligands may be used, as well as a variety of solvents, including for example dioxane and toluene.

The required quinoline, [1,5]-naphthyridine, quinazoline and quinoxaline derivatives of formula II are prepared following literature procedures. For example, 4-hydroxy-[1,5]-naphthyridines ($L^1$=OH; U=W=N; and V=X=CH) and 4-hydroxy quinolines ($L^1$=OH; W=N; and U=V=X=CH) can be prepared from the corresponding aminopyridines or anilines by reaction with diethyl ethoxymethylene malonate to produce the 4-hydroxycarboxylic acid ester derivative with subsequent hydrolysis to acid, followed by thermal decomposition in inert solvents (J. T. Adams, *J. Am. Chem. Soc.* (1946), 68, 1317). Others routes to such derivatives use the condensation of substituted aminopyridines or anilines with 2,2-dimethyl-[1,3]dioxane-dione and triethylorthoformate followed by heating of the resulting 2,2-dimethyl-5-[(arylamino)methylidene]-1,3-dioxane-4,6-dione intermediate in refluxing diphenyl ether. Quinazolines ($L^1$=OH, Cl, $NH_2$; W=X=N; and U=V=CH) may be prepared by standard routes as described by T. A. Williamson in *Heterocyclic Compounds* (1957), 6, 324. 3-substituted quinoxalin-5-ol ($L^1$=OH, U=V=N and X=W=CH) can be prepared as described by Y. Abe et al. in *J. Med. Chem.* (1998), 41, 4062.

The compounds of formula I can be prepared by different routes as illustrated in Schemes 1-10 below (reference is made to Table 1 above):

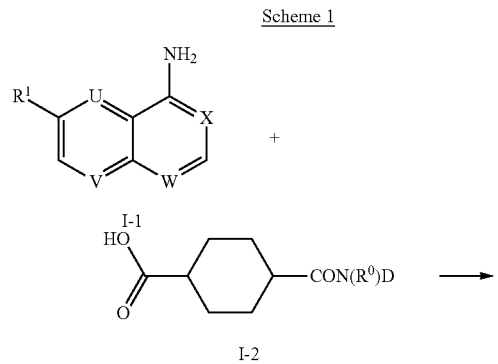

Scheme 1

In Scheme 1, $R^0$, $R^1$, U, V, W, X and D have the same meanings as in formula I.

Compounds of formula I can for example be obtained from the compound I-1 and the carboxylic acid I-2.

To prepare the compound I-1, a 4-hydroxy-[1,5]-naphthyridine, a 4-hydroxyquinazoline, a 5-hydroxyquinoxaline or a 4-hydroxyquinoline derivative can be converted into the corresponding chloro derivative by heating in phosphorous oxychloride between 40° C. and 100° C. neat or in an inert solvent like 1,2-DCE, or to the corresponding trifluoromethanesulphonyloxy derivative by reaction with trifluoromethanesulphonic anhydride, in the presence of an organic base between −40° C. and 80° C. in an aprotic solvent like DCM or THF (K. Ritter, *Synthesis* (1993), 735). The corresponding 4-amino-[1,5]-naphthyridine, 4-aminoquinazoline, 5-aminoquinoxaline or 4-aminoquinoline derivatives can then be obtained by reaction of the corresponding trifluoromethanesulphonyloxy derivatives with ammonia in a solvent like DCM or THF, or with n-propylamine hydrochloride in pyridine between −20° C. and 100° C. (R. Radinov, *Synthesis* (1986), 886). The corresponding 4-aminoquinazoline can also be obtained from its 4-chloro analogue by reaction with ammonia under the same conditions.

Carboxylic acids I-2 may be prepared by Jones' oxidation of the corresponding alcohols using chromium acid and sulphuric acid in water/MeOH between 40° C. and 110° C. (E. R. H. Jones et al, *J. Chem. Soc.* (1946), 39). Other oxidising agents may be used for this transformation such as $NaIO_4$ catalysed by ruthenium trichloride (G. F. Tutwiler et al, *J. Med. Chem.* (1987), 30, 1094), or $KMnO_4$ (D. E. Reedich et al, *J. Org. Chem.* (1985), 50, 3535.

Derivatives I-3 can be obtained by reacting the 4-amino derivative I-1 with a carboxylic acid derivative I-2, in the presence of an activating agent such as DCC or EDC (both with or without HOBT), TPPA or HATU (G. Benz in *Com-* prehensive Organic Synthesis, B. M. Trost, I. Fleming, Eds; Pergamon Press: New York (1991), vol. 6, p. 381) between −20° C. and 60° C. in an dry aprotic solvent like DCM, MeCN or DMF. Alternatively, the carboxylic acid can be activated by conversion into its corresponding acid chloride after reaction with oxalyl chloride or thionyl chloride neat or in a solvent like DCM between −20° and 60° C.

ligands may be used, as well as a variety of solvents, including for example dioxane and toluene. Alternatively, halogenated derivatives of formula II-1 ($L^1$=I, Br or Cl) may be used in the metal-catalysed coupling reaction. In a subsequent step, the protecting group G is removed, if required, and the resulting carboxylic acid can be coupled with a compound of formula V using the reaction conditions already mentioned to yield compound I-4. Alternatively, the carboxylic acid derivative may be transformed into the corresponding amide by, for example, activating the carboxylic acid with isobutylchloroformate in presence of TEA in an inert solvent such as THF or DCM and quenching the intermediate with the amine $R^0NH_2$. The resulting amide is reacted with a compound of formula VII to give compound I-4 wherein D represents styryl or heteroarylvinyl using methods already described.

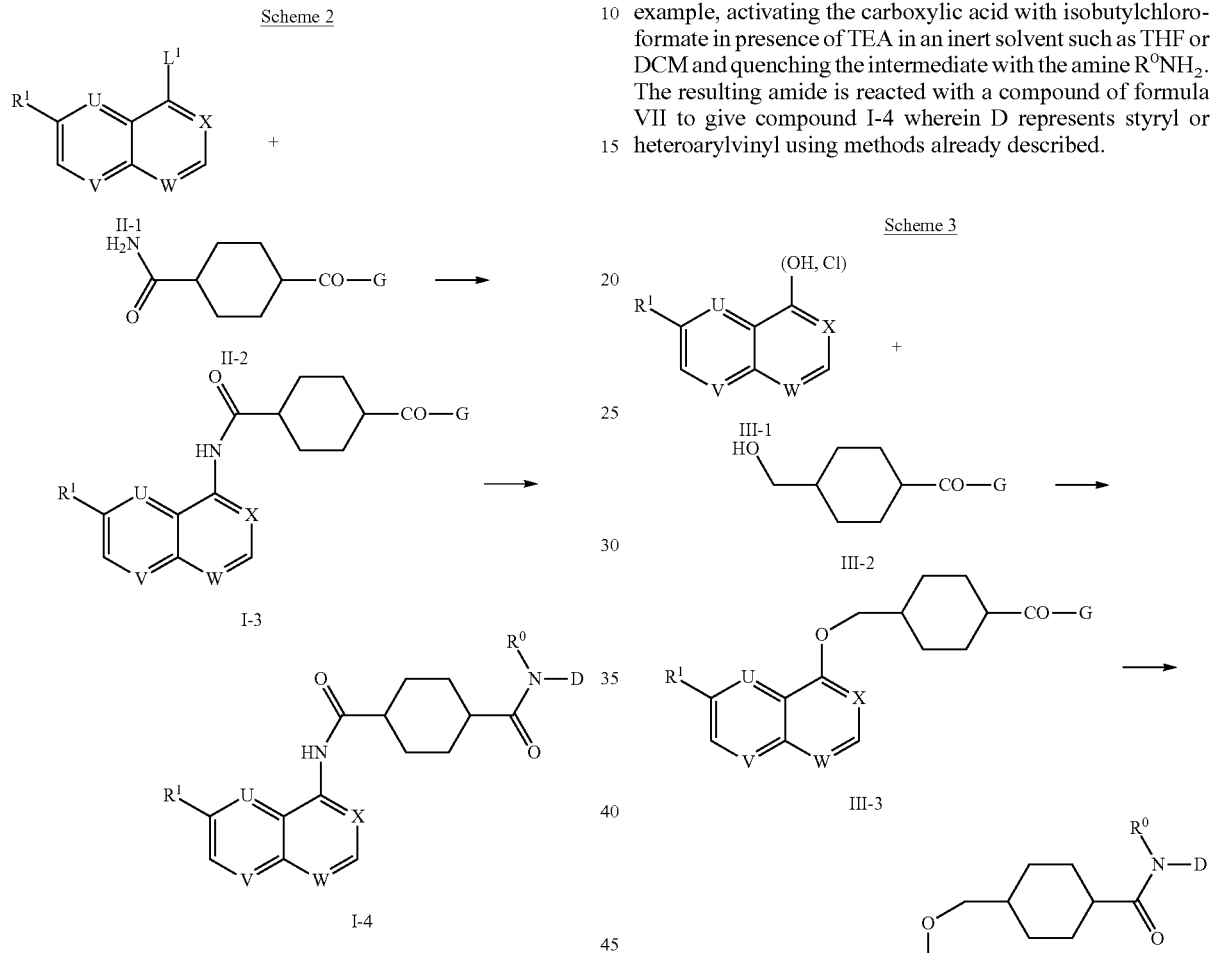

In Scheme 2, $L^1$ is halogen or OTf, G is a protecting group such as allyloxy, benzyloxy, ethyloxy or tert-butoxy, and the other symbols have the same meanings as in formula I. According to the nature of D, compounds of formula II-2 wherein G represents $N(R^0)$-D can be used in the first reaction.

As illustrated in Scheme 2, the intermediate I-3 can also be obtained from a 4-trifluoromethanesulfonate derivative II-1 and an amide derivative II-2. These amide derivatives are obtained from a suitable carboxylic acid I-2, which is converted into an activated form using, for example, TPPA, EDC, HOBT, $SOCl_2$, NHS or DCC between −20° C. and 60° C. in a dry aprotic solvent like DCM, EA or THF, and the activated acid is subsequently reacted with aq. $NH_4OH$ or gaseous ammonia to afford amide of formula II-2 in an appropriate solvent such as THF or DCM between −20° C. and 60° C. The amide II-2 and the 4-trifluoromethanesulphonate II-1 are coupled under palladium-catalyzed Buchwald-Hartwig conditions (J. Am. Chem. Soc. (1996), 118, 10333) or copper-catalyzed conditions (J. Am. Chem. Soc. (2002), 124, 7421) to afford the derivative I-3. Various palladium sources and In Scheme 3, G is a protecting group such as allyloxy, benzyloxy, ethyloxy or tert-butoxy, and $R^0$, $R^1$, U, V, W, X and D have the same meanings as in formula I. According to the nature of D, compounds III-2 wherein G represents $N(R^0)$-D can be used in the first reaction.

As shown in Scheme 3, the compounds of formula I can also be obtained by coupling, for example, a substituted 4-hydroxyquinoline, 8-hydroxyquinoline, 4-hydroxy-[1,5]-naphthyridine, 4-hydroxy-[1,3]-quinazoline or 5-hydroxyquinoxaline III-1 and an alcohol derivative III-2. The coupling reaction between the compounds III-1 and III-2 can be achieved under Mitsunobu conditions (as reviewed in O. Mitsunobu, Synthesis 1981, 1). For example, an alcohol III-2 and a 4-hydroxy derivative III-1 are reacted to form the ether III-3 in the presence of DEAD or DIAD and $PPh_3$. The reaction can be performed in a wide range of solvents such as DMF, THF, DCM and at a wide range of temperatures (between −78° C. and 50° C.). An alternate route to the compound III-3 requires the activation of the alcohol III-2 as for example a tosylate, a triflate or a mesylate by treatment with TsCl, trifluoromethanesulphonic anhydride or MsCl respectively in the presence of an organic base such as TEA between −40° C. and 60° C. in a dry aprotic solvent like DCM, MeCN or THF. Once activated, the alcohol III-2 reacts at a temperature between −20° C. and 60° C. with the anion of the 4-hydroxy derivative, generated with a mineral base such as NaH or $K_2CO_3$ or an organic base such as LiHMDS, to yield the compound III-3. Alternatively, the compound III-3 can be obtained by reaction of a 4-halogenoquinazoline derivative with an alcohol derivative III-2, in presence of a strong base like an alkali alkoxide (e.g. sodium or potassium methylate), a metal hydride (e.g. NaH), DBU or DBN, at a temperature between −20° C. and 60° C. and in a dry aprotic solvent like DMF, MeCN or THF. In a subsequent step, compound III-3 is transformed into compound III-4 using the same protocol as for the conversion of compound I-3 into compound I-4.

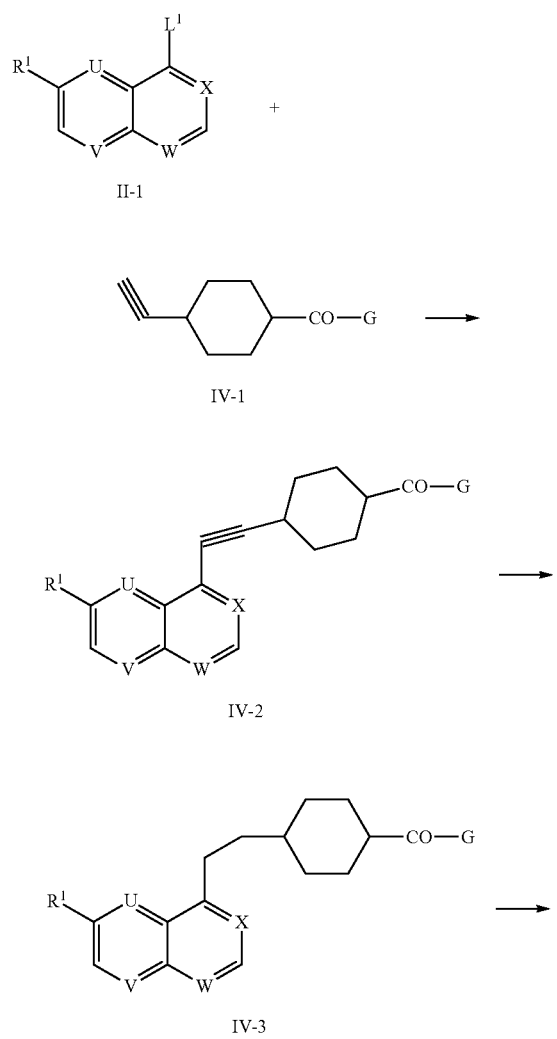

Scheme 4

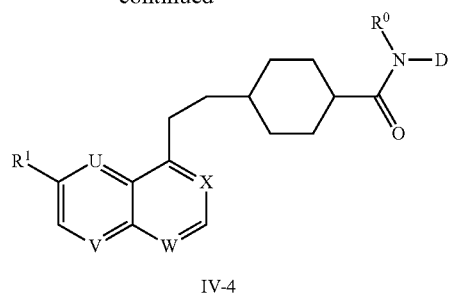

IV-4

In Scheme 4, $L^1$ is $OSO_2CF_3$ or a halogen atom, G is a protecting group such as ethyloxy or tert-butoxy, and $R^0$, $R^1$, U, V, W, X and D have the same meanings as in formula I. According to the nature of D, compounds IV-1 wherein G represents $N(R^0)$-D can be used in the first reaction.

Compounds of formula I can also be obtained from compounds II-1 (Scheme 4) The intermediate IV-2 may be obtained from the derivative II-1 and a terminal alkyne derivative IV-1. These alkyne derivatives IV-1 are generally obtained from suitable alcohols III-2 (see Scheme 3) which are converted first into aldehydes using for example the Moffat-Swern (see *Synthesis* (1981), 165), or the Dess-Martin periodinane (see *J. Am. Chem. Soc.* (1991), 113, 7277) oxidation protocols. The aldehyde is converted into the corresponding alkyne using dimethyl-1-diazo-2-oxopropylphosphonate (so called Ohira's reagent, *Synth. Com.* (1989), 19, 561) or dimethyldiazomethylphosphonate as described in *Synlett* (2003), 59 and *Synlett* (1996), 521. The alkyne IV-1 and the 4-trifluoromethanesulfonate II-1 are coupled under Sonogashira conditions using a catalytic amount of a palladium salt, an organic base such as TEA and a catalytic amount of a copper derivative (usually copper iodide) in a solvent such as DMF between 20° C. to 100° C. (see Sonogashira, K. in *Metal-Catalyzed Reactions*, Diedrich, F., Stang, P. J., Eds; Wiley-VCH: New York 1998). Alternatively, for example when U=V=CH and W=X=N, the 4-trifluoromethanesulfonate II-1 can be replaced by a halogeno (e.g. chloro) derivative II-1. The resulting alkyne IV-2 is hydrogenated to yield the compound IV-3 using catalytic system such as palladium on charcoal or platinum oxide in a solvent like EtOH or EA in presence of hydrogen. Other methods may also be suitable as reviewed by Siegel, S. et al. in *Comprehensive Organic Synthesis*, B. M. Trost, I. Fleming, Eds; Pergamon Press: New York (1991), vol. 8, p. 417-488. The compound IV-3 is further transformed into the compound IV-4 using procedures previously described.

Scheme 5

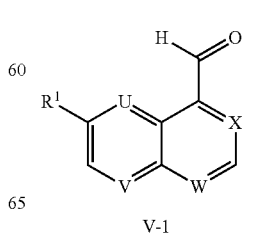

V-1

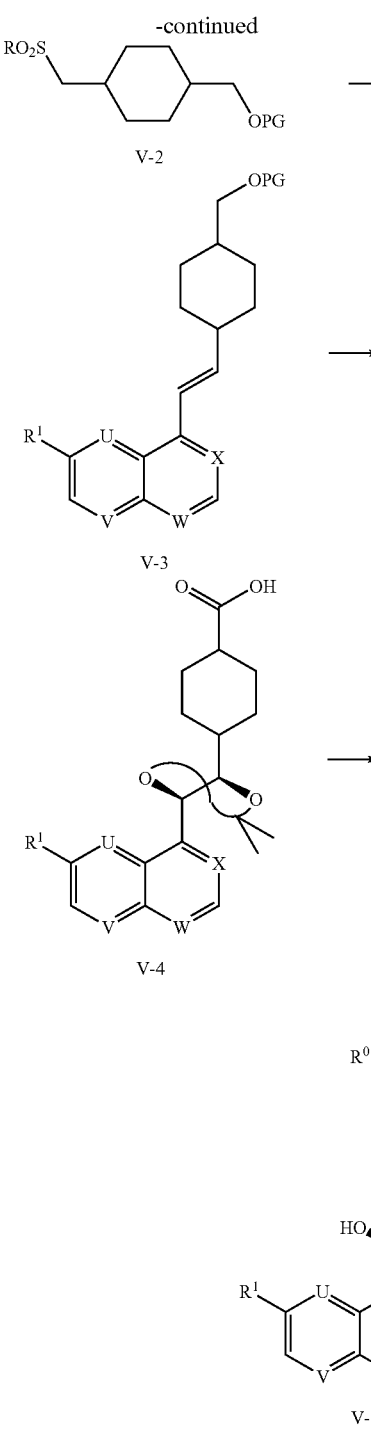

Blakemore, P. R in *J. Chem. Soc., Perkin Trans.* 1 (2002), 2563-2585. The (E)-alkene V-3 is transformed into the corresponding chiral cis-diol derivative by treatment with AD mixtures in presence of methanesulfonamide in a water/2-methyl-2-propanol mixture as described in *Chem. Rev.* (1994), 94, 2483. The sense of induction relies on the chiral ligand contained in the mixture, either a dihydroquinine-based ligand in AD-mix α or a dihydroquinidine-based ligand in AD-mix β. The chiral diol is then protected in the form of an isopropylidene acetal (acetonide) using either acetone, 2,2-dimethoxypropane or 2-methoxypropene in presence of a catalytic amount of PTSA or CSA. Depending on the nature of the protecting group PG, various strategies can be used to selectively remove it.

For example, in the case of a silyl ether, the use of TBAF in THF efficiently leads to the corresponding primary alcohol. The alcohol is further oxidized to the acid V-4 via the corresponding aldehyde using one of the aforementioned methods. The acid is then obtained under oxidizing conditions using either $KMnO_4$ in aq. acetone or sodium chlorite in aq. 2-methyl-2-propanol (see *Tetrahedron* (1981), 37, 2091-2096). The acid is transformed into the corresponding amide using methods previously described. The acetonide may then be removed using a variety of aq. acids, such as aq. TFA, AcOH, HCl or an acidic resin such as Dowex $H^+$ in MeOH, thus affording the amide V-5.

Scheme 6

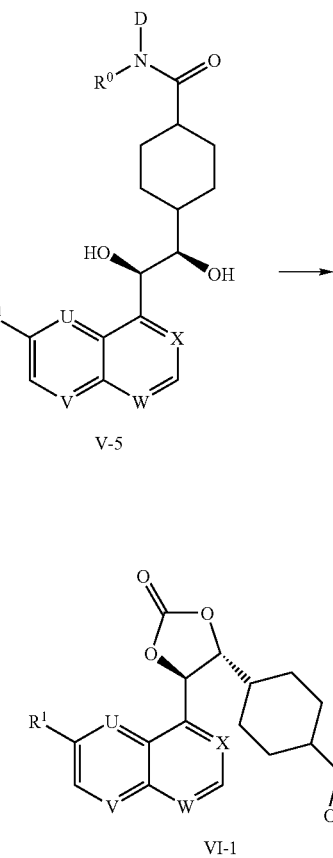

In Scheme 5, PG is a protecting group such as tert-butyldimethylsilyl, tert-butyldiphenylsilyl, para-methoxybenzyl, tetrahydropyrannyl, R may be 1-phenyl-1H-tetrazol-5-yl or benzothiazol-2-yl and $R^0$, $R^1$, U, V, W, X and D have the same meanings as in formula I.

Compounds of formula I can also be obtained from compounds V-1 (Scheme 5). Intermediate V-3 can be obtained as an (E)-isomer from an aldehyde derivative V-1 and a sulfone V-2. The sulfone V-2 and the aldehyde V-1 are coupled in presence of a base such as KHMDS or LiHMDS in a solvent such as 1,2-DME, DMF or toluene as reviewed by

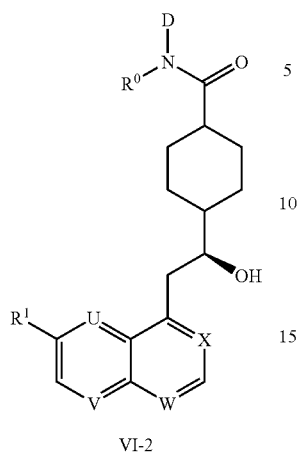

VI-2

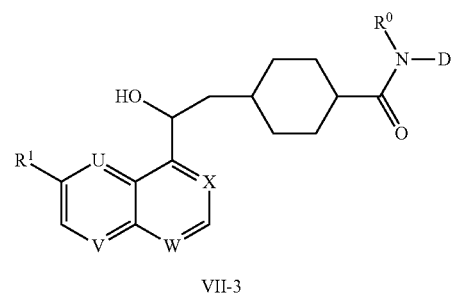

VII-3

In Scheme 6, R⁰, R¹, U, V, W, X and D have the same meanings as in formula I.

As illustrated in Scheme 6, the previously mentioned chiral cis-diol V-5 may be transformed into the corresponding cyclic carbonate VI-1, by treatment with either phosgene, diphosgene or triphosgene in presence of an organic base such as TEA or pyridine or carbonyldiimidazole in an inert solvent such as DCM or THF at a temperature ranging between −78° C. and 50° C., more conveniently at a temperature ranging between 0° C. and 20° C. The cyclic carbonate VI-1 is subsequently converted into the homobenzylic alcohol VI-2 by hydrogenolysis using catalytic system such as Pd/C in presence of hydrogen in a solvent such as EA.

In Scheme 7, L¹ is a halogen atom, G is a protecting group such as allyloxy, benzyloxy, ethyloxy or tert-butoxy, and R⁰, R¹, U, V, W, X and D have the same meanings as in formula I. According to the nature of D, compounds VII-1 wherein G represents N(R⁰)-D can be used in the first reaction.

As illustrated in Scheme 7, the benzylic alcohol VII-2 may be obtained by addition of an aromatic organometallic derivative II-1 onto an aldehyde VII-1. The aldehyde VII-1 is obtained from a suitable alcohol III-2 by a homologation reaction. Oxidation of the alcohol III-2 into its corresponding aldehyde may be performed using one of the aforementioned oxidation methods. The resulting aldehyde is further converted to the corresponding alkene using the phosphorane generated from methyltriphenylphosphonium bromide and a base like n-BuLi or potassium tert-butoxide in a solvent such as THF at a temperature between −80° C. and 0° C. (see *Org. Synth. Coll.* (1973), 5, 751). The terminal alkene is subsequently transformed into the primary alcohol via an hydroboration reaction using either BH₃-dimethylsulfide complex, or 9-BBN (for a review see Smith, K.; Pelter, A. G. *Comprehensive Organic Synthesis*, B. M. Trost, I. Fleming, Eds; Pergamon Press: New York (1991), vol. 8, p. 703-731) followed by oxidative workup with aq. NaOH and 30% H₂O₂ (see also Pelter, A.; Smith, K. G. *Comprehensive Organic Synthesis*, B. M. Trost, I. Fleming, Eds; Pergamon Press: New York (1991), vol. 7, p. 593-611). The alcohol is finally oxidized to the aldehyde VII-1 as already described. Derivatives II-1 (L¹=Br) are treated with an alkyllithium such as n-BuLi at a temperature ranging between −80° C. and −30° C. to generate a lithio species that undergoes nucleophilic addition on to the aldehyde VII-1 to yield the benzylic alcohol VII-2. The intermediate VII-2 is further transformed into the compound VII-3 using procedures previously described.

Scheme 7

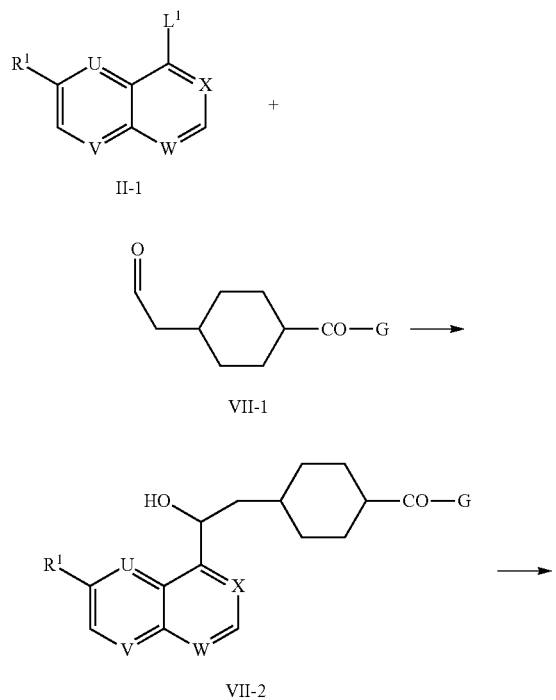

Scheme 8

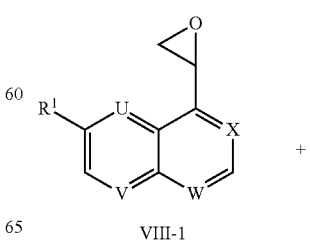

VIII-1

+

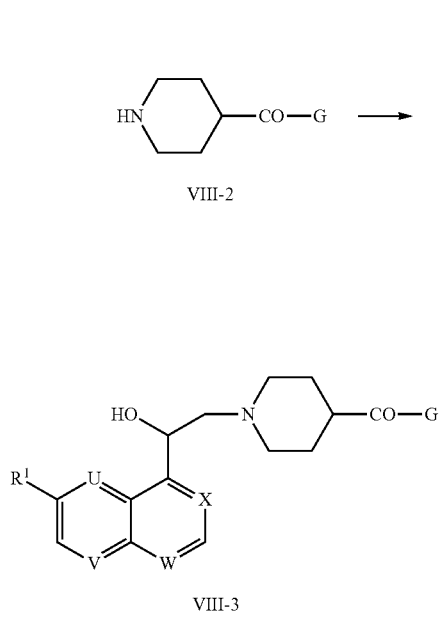

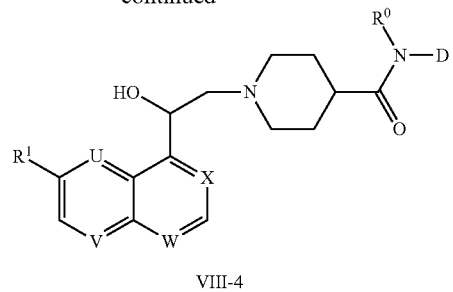

In Scheme 8, G is a protecting group such as allyloxy, benzyloxy, ethyloxy or tert-butoxy, and $R^0$, $R^1$, U, V, W, X and D have the same meanings as in formula I. According to the nature of D, compounds VIII-2 wherein G represents $N(R^0)$-D can be used in the first reaction.

As shown in Scheme 8, the compounds of formula I can also be obtained by reacting a compound of formula VIII-1 with a piperidine derivative VIII-2. The reaction is promoted by a Lewis acid such as $LiClO_4$ in the presence of an alkali metal carbonate, such as $K_2CO_3$ and in a solvent such as DMF at a temperature ranging between 20° C. and 100° C., more preferably at a temperature in the vicinity of 80° C. The intermediate VIII-3 is further transformed into the compound VIII-4 using procedures previously described.

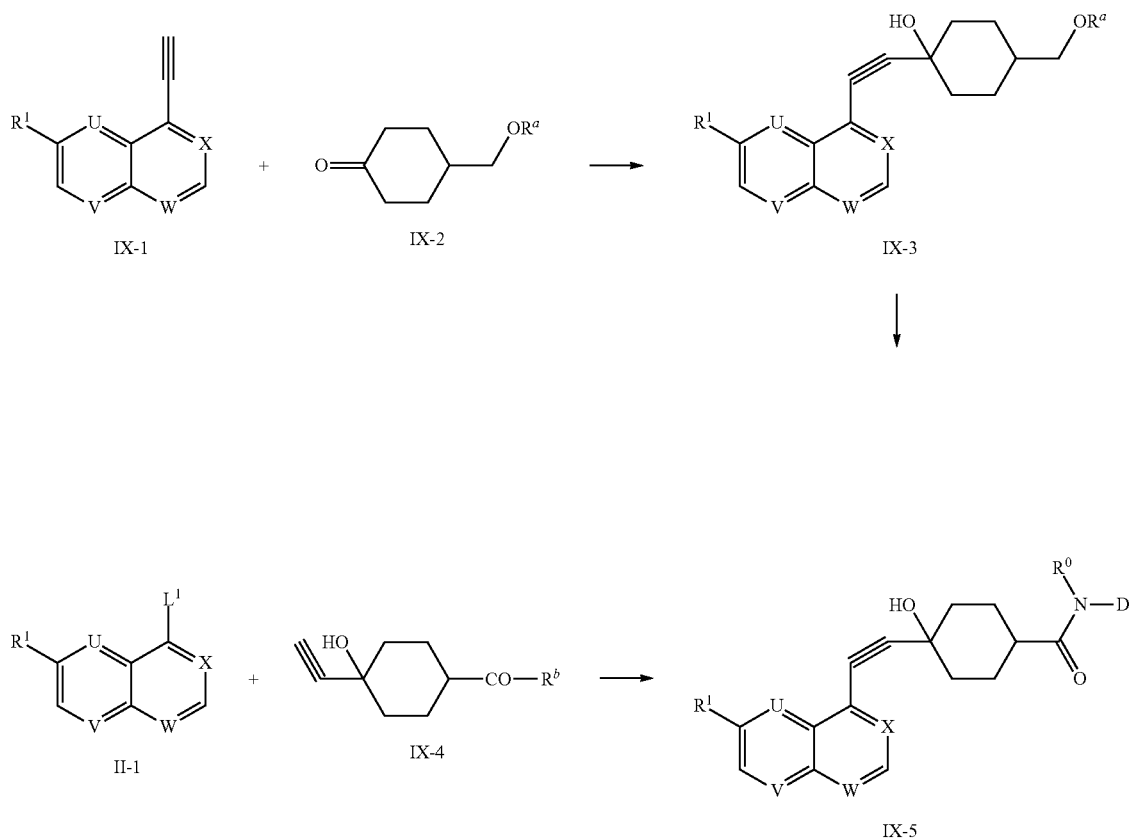

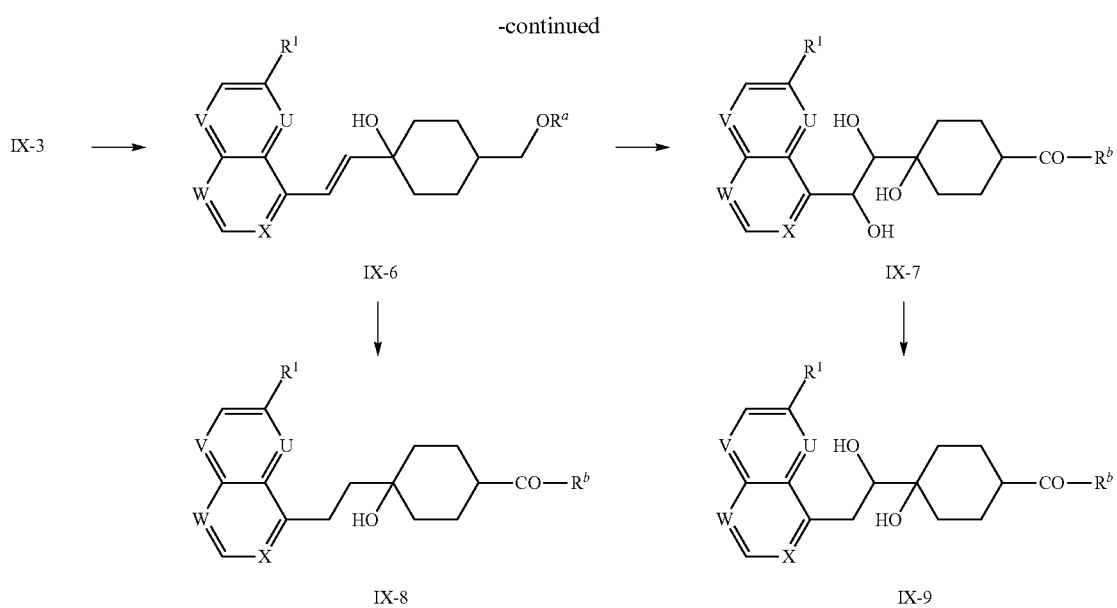

IX-6          IX-7

IX-8          IX-9

In Scheme 9, $R^a$ is tert-butyldimethylsilyl, tert-butyldiphenylsilyl, para-methoxybenzyl or tetrahydropyrannyl, $R^b$ is ethyloxy, benzyloxy or tert-butoxy, $L^1$ is $OSO_2CF_3$ or a halogen atom, and $R^0$, $R^1$, U, V, W, X and D have the same meanings as in formula I.

As shown in Scheme 9, the compounds of formula I can also be obtained by reacting the anion of a compound IX-1 with a cyclohexanone derivative IX-2 in presence of cerium trichloride. The anion of the terminal alkyne IX-1 may be obtained by treatment with a strong base such as n-BuLi or ethyl magnesium bromide in THF at a temperature ranging between −78° C. and −30° C. The ether IX-3 is deprotected and transformed into the corresponding amide derivative IX-5 using methods already reported for the conversion of intermediate V-3 into the amide derivative V-5.

Alternatively, compound IX-5 can be obtained by reacting a compound II-1 ($L^1$=OTf) with an acetylenic compound IX-4 under Sonogashira conditions, i.e. using catalytic amount of a palladium salt, an organic base such as TEA and a catalytic amount of a copper derivative (usually copper iodide) in a solvent such a DMF between 20° C. to 100° C. (see Sonogashira, K. in *Metal-Catalyzed Reactions*, Diedrich, F., Stang, P. J., Eds; Wiley-VCH: New York 1998). When, for example U=V=CH and W=X=N, the 4-trifluoromethanesulfonate II-1 can be replaced by a halogeno derivative II-1 (e.g. one wherein $L^1$=Cl).

Intermediate IX-3 can be selectively reduced into the corresponding trans-olefin derivative IX-6 using $LiAlH_4$ in THF or lithium in liquid ammonia as described in *J. Org. Chem.* (2005), 70, 2455. The alcohol IX-6 can be transformed into the corresponding triol IX-7. Thus, the ether is deprotected and transformed into the corresponding carboxylic derivative using methods already reported for the conversion of intermediates V-3 into the carboxylic acid derivatives V-4. The acid is converted into the corresponding esters using standard methodologies. The cis-diol functionality is introduced using the same reaction conditions as those described for the preparation of compounds V-5, affording compounds IX-7. Alternatively, the compound IX-6 can be hydrogenated into the corresponding alkane derivative IX-8 using a noble catalyst as described for the preparation of compounds IV-3. The triol IX-7 can be transformed into the diol IX-9 following the protocols described for the preparation of compounds VI-2.

The intemediates IX-7, IX-8 and IX-9 can be further transformed into the corresponding final compounds wherein $R^b$ is replaced by $N(R^0)$-D using any of the procedures previously described for such transformation.

Scheme 10

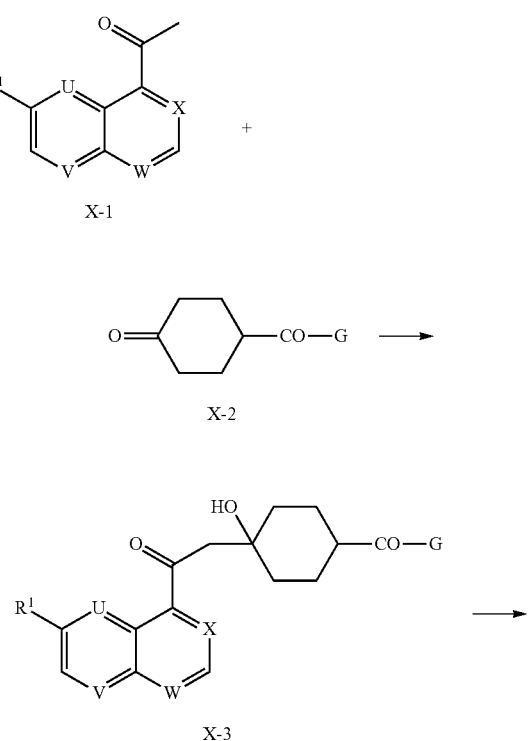

X-1

X-2

X-3

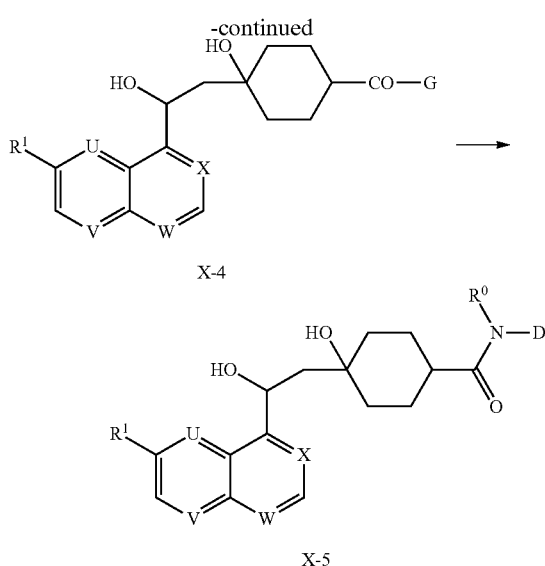

In Scheme 10, G is a protecting group such as allyloxy, benzyloxy, ethyloxy or tert-butoxy, and $R^0$, $R^1$, U, V, W, X and D have the same meanings as in formula I. According to the nature of D, compounds X-2 wherein G represents $N(R^0)$-D can be used in the first reaction.

As shown in Scheme 10, the compounds of formula I can also be obtained by reacting compound X-1 with a cyclohexanone derivative X-2 after deprotonation of the methyl ketone with a strong base such as lithium diisopropylamide in a solvent like THF between −100° C. and 0° C., preferably between −78° C. and −30° C. The resulting keto-alcohol derivative X-3 can be reduced with an alkali borohydride such as $LiBH_4$ or $NaBH_4$ into the corresponding diol X-4. The reduction can also be performed using chiral reducing agents as described in *J. Org. Chem.* (1988), 53, 2861 or by asymmetric hydrogenation as described in *Acc. Chem Res.* (1997), 30, 97-102. Finally compounds of formula X-4 are transformed into the corresponding compounds of formula X-5 using procedures previously described.

Compounds of formula I containing at least a free hydroxyl group (e.g. compounds V-5, VI-2, VII-3, VIII-4 and IX-5, and compounds IX-7, IX-8, IX-9 wherein $R^b$=NH-D) can be converted into their corresponding prodrugs. Thus, for example, compound VI-2 can be reacted with a phosphoramidite reagent (e.g. dibenzyl N,N-diisopropylphosphoramidite) in presence of tetrazole or 4,5-dicyanoimidazole in a solvent such as DCM at temperatures ranging between 0° C. and 40° C. The intermediate can then be further oxidized with $H_2O_2$ in a solvent such as DCM at temperature ranging between 0° C. and 40° C. The resulting phosphate ester is deprotected, e.g. by hydrogenolysis or treatment with hydrobromic acid in the case of dibenzyl phosphate esters, affording the phosphate prodrug ($R^5$=$PO_3H$). Alternatively, compound VI-2 can be reacted with dibenzyl or di tert-butyl phosphite and chloroiodomethane in presence of an organic base as described in *Bioorg. & Med. Chem. Lett.* (2003), 13, 3669. The phosphate ester can then be deprotected either under acidic conditions or after hydrogenolysis, affording the oxymethylene phosphate prodrug ($R^5$=$CH_2OPO_3H$). Compound VI-2 can also be reacted with pyridine-$SO_3$ or $Me_3N$—$SO_3$ complex in pyridine between 0° C. and 60° C. affording the corresponding sulphate prodrug ($R^5$=$SO_3H$) as described for example in *Angew. Chem., Internat. Ed.* (2005), 44, 6759. Compound VI-2 can also be reacted with an activated form of a succinate, of an amino acid or of dimethylglycine to give the corresponding esters ($R^5$=$COR^9$). Typical activation methods have been reported in the present document (see e.g. preparation of compounds I-3).

Starting Materials:

Aldehydes V-1 are prepared following literature procedures or from the corresponding derivatives II-1 ($L^1$=Br) are after treatment with an alkyllithium such as n-BuLi in a solvent like THF at a temperature ranging between −80° C. and −30° C. and subsequent quenching of the lithio species with DMF as described in *J. Org. Chem.* (1980), 45, 1514.

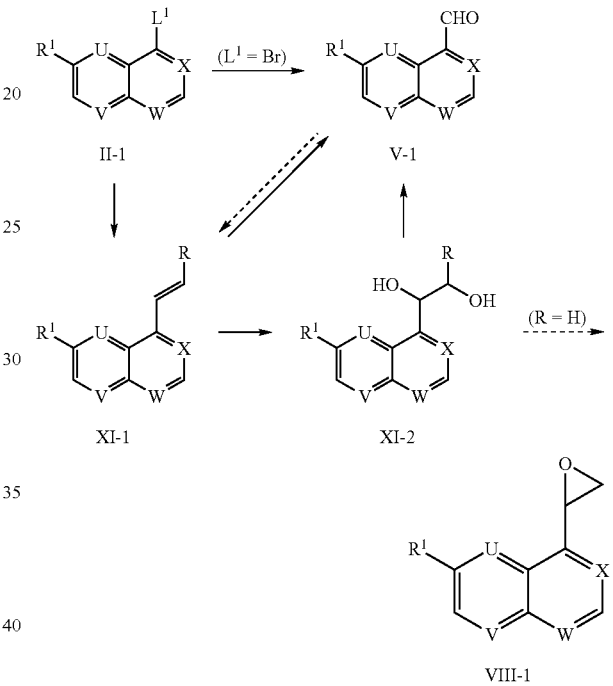

In Scheme 11, $L^1$ represents OTf, Br or Cl, R is hydrogen, alkyl or aryl, and $R^1$, U, V, W and X have the same meanings as in formula I.

An alternate route to generate aldehydes V-1 consists in reacting derivative II-1 ($L^1$=OTf, Br or Cl) with trans-phenylvinyl boronic acid under typical Miyaura-Suzuki coupling conditions (see *Synth. Commun.* (1981), 11, 513) employing a palladium salt, an inorganic base such as $K_2CO_3$ or $Na_2CO_3$, in an aq. solvent such as a dioxane-water mixture and at a temperature ranging between 20° and 100° C. The corresponding alkenes may be directly transformed into the aldehydes V-1 by ozonolysis ($O_3$ stream then quenching with either dimethylsulfide or $PPh_3$) or via a periodic cleavage of the intermediate diols using $NaIO_4$ in aq. acetone. The diols are obtained using a catalytic amount of $OsO_4$ in the presence of a co-oxidant such as NMO in an aq. solvent such as acetone-water or DCM-water (see Cha, J. K. *Chem. Rev.* (1995), 95, 1761-1795).

Alternatively, the aldehydes V-1 may be obtained by reaction of the bromide with carbon monoxide under pressure in presence of a palladium catalyst. The bromide may also be transformed to the aromatic nitrile using conditions reported in *J. Org. Chem.* (2005), 70, 1508-1510 and subsequent controlled reduction of the nitrile using DIBAH in a solvent such as THF or DCM at a temperature ranging between −80° C. and 20° C., most preferably at a temperature in the vicinity of 0° C.

The aldehydes V-1 can be transformed into the corresponding alkenes XI-1 (R=H) by treatment with the phosphorous ylide generated by deprotonation of methyltriphenylphosphonium bromide using a base such as n-BuLi in THF at a temperature ranging between −78° C. and 10° C. (dotted arrow; Scheme 11). The alkenes XI-1 are transformed into the corresponding chiral diols XI-2 using the Sharpless asymmetric dihydroxylation protocol as described in *Chem. Rev.* (1994), 94, 2483. Both enantiomers of the diols XI-2 are accessible, using either a chiral ligand based on dihydroquinine (contained in the commercially available AD-mix α) or based on dihydroquinidine (contained in the commercially available AD-mix β). Several strategies are possible to transform the chiral diols XI-2 into the corresponding epoxides VIII-1 without loss of enantiomeric purity. The primary alcohol is selectively transformed into a leaving group, such as methanesulfonyloxy or para-toluenesulfonyloxy, by treatment with MsCl or TsCl in the presence of an organic base such as TEA or pyridine at a temperature ranging between −78° C. and 0° C., more preferably at a temperature ranging between −30° C. and −10° C. The resulting methane- or toluene-sulfonyloxy derivatives are transformed into the desired epoxides VIII-1 by treatment with an inorganic base such as $K_2CO_3$ in a solvent such as MeOH or EtOH. Alternatively, the diols XI-2 are transformed into the corresponding epoxides VIII-1 using the methodology developed by Sharpless and reported in *Tetrahedron* (1992), 48, 10515.

The methyl ketone derivatives X-1 can be obtained from compounds II-1 ($L^1$=Br). The corresponding anions generated following the protocol described for the synthesis of compounds V-1 are reacted with acetaldehyde. The resulting alcohol is oxidized into the corresponding ketone using a variety of standard methods such as oxidation by $MnO_2$ or Swern oxidation. The methyl ketone X-1 can also be obtained from derivative II-1 ($L^1$=$OSO_2CF_3$ or Br) and tributyl (1-ethoxyethenyl) stannane via a Stille reaction followed by acidic hydrolysis as described in *Tetrahedron* (2001), 57, 2507.

The cyclohexane derivatives I-2 and III-2 are commercially available. Compounds II-2 can be obtained from the carboxylic acid I-1 and ammonia after prior activation of the carboxylic acid using an activating agent such as EDC, HOBT or HATU (G. Benz in *Comprehensive Organic Synthesis*, B. M. Trost, I. Fleming, Eds; Pergamon Press: New York 1991, vol 6, p. 381) between −20° C. and 60° C. in an dry aprotic solvent like DCM, MeCN or DMF, or from the corresponding alkyl ester after reaction with ammonia.

The acetylenic derivatives IV-1 can be obtained in a two step procedure starting from the cyclohexanone-4-carboxylic ester or respectively cyclohexanone-4-carboxamide derivatives after reaction with trimethylsilylacetylene in a solvent such as THF between −40 and −100° C., preferably between −78 and −50° C. The intermediate silane derivatives are hydrolysed in a protic solvent such as MeOH or EtOH in presence of an alkali carbonate such as $K_2CO_3$.

The sulfone V-2 is generated from the known [4-(tert-butyl-dimethyl-silanyloxymethyl)-cyclohexyl]-methanol (see *J. Med. Chem.* (2001), 44, 531). The corresponding sulphide is obtained from this alcohol using a Mitsunobu coupling (as reviewed in O. Mitsunobu *Synthesis* (1981), 1) with 1-phenyl-1H-tetrazole-5-thiol in the presence of DEAD or DIAD and $PPh_3$. The reaction may be performed in a wide range of solvents such as DMF, THF or DCM and within a wide range of temperatures (between −78° C. and 50° C.). An alternate route to form the intermediate sulphide requires the activation of the alcohol as for example a tosylate, a triflate or a mesylate by treatment with TsCl, trifluoromethanesulphonic anhydride or MsCl respectively in the presence of an organic base such as TEA between −40° C. and 60° C. in a dry aprotic solvent like DCM, MeCN or THF. Once activated, the reaction with NaI or KI in acetone at a temperature ranging between 0° C. and 65° C., forms the corresponding iodide. The latter serves as an alkylating agent of the 1-phenyl-1H-tetrazole-5-thiol. The alkylation reaction is performed in presence of an inorganic base such as KOH or NaOH in a solvent such as EtOH at a temperature ranging between −20° C. and 70° C. The sulfone V-2 is transformed to the corresponding sulphide via an oxidation reaction. A wide range of oxidizing agent may be used, such as MCPBA in a solvent such as DCM or oxone in a solvent such as aq. MeOH (see *Tetrahedron Letters* (1981), 22, 1287), or aq. hydrogen peroxide in presence of ammonium heptamolybdate tetrahydrate in EtOH (see *J. Org. Chem.* (1963), 28, 1140).

The aldehyde derivatives VII-1 were obtained from the corresponding alcohol derivatives III-2 after oxidation into the corresponding aldehydes using for example a Swern protocol. Subsequent Wittig reaction with methoxymethylene triphenylphosphorane followed by acidic hydrolysis with aqueous trichloroacetic acid or HCl as described by Kazuta et al. in *J. Med. Chem.* (2003), 46, 1980-88, led to the aldehyde derivatives VII-1.

Particular embodiments of the invention are described in the following Examples, which serve to illustrate the invention in more detail without limiting its scope in any way.

EXAMPLES

All temperatures are stated in ° C. All analytical and preparative HPLC investigations on non-chiral phases are performed using RP-C18 based columns. Analytical HPLC investigations are performed on two different instruments with cycle-times of ~2.5 min and ~3.5 min respectively.

Preparation A:
3-methoxy-quinoxaline-5-carbaldehyde

A.i. 2-cyano-N-(2-methyl-6-nitro-phenyl)-acetamide:

To a solution of 2-methyl-6-nitroaniline (25 g, 164.3 mmol) in benzene (200 mL) were added cyanoacetic acid (14.5 g, 170.46 mmol) and $PCl_5$ (35 g, 168 mmol). The reaction mixture was heated at 60° C. for 7 h. After cooling to rt, the reaction mixture was filtered and the solid was washed with benzene and water. The solid was dried under reduced pressure to afford the title acetamide (24 g, 109 mmol) as a yellow solid.

$^1$H NMR (DMSO d6) δ: 10.2 (s, 1H); 7.78 (d, J=8.3 Hz, 1H); 7.65 (d, J=8.3 Hz, 1H); 7.43 (t, J=8.3 Hz, 1H); 3.95 (s, 2H); 2.30 (s, 3H).

A.ii. 3-hydroxy-5-methyl-1-oxy-quinoxaline-2-carbonitrile:

To a solution mixture of intermediate A.i (24 g, 109.5 mmol) in 1M aq. NaOH (100 mL) was added pyridine (100 mL). The reaction mixture was stirred at rt for 4 h. The pH was adjusted to 6 by addition of 1M aq. HCl. The solid was filtered off and washed with water. The solid was triturated with EtOH. After drying under HV, the title nitrile (17.7 g, 87.9 mmol) was obtained as a yellow solid.

MS (ESI, m/z): 202.1 [M+H]$^+$.

A.iii. 8-methyl-quinoxalin-2-ol:

To a solution of intermediate A.ii (17.7 g, 87.9 mmol) in water (300 mL) and EtOH (24 mL) was added sodium dithionite (35.4 g, 203.9 mmol). The reaction mixture was heated at 60° C. for 1 h. The reaction mixture was filtered till warm, and the pH of the filtrate was adjusted to 2 by adding 1M aq. HCl. The pH of the solution was subsequently made basic by adding solid NaOH (10 g). EA (150 mL) was added. The aq. layer was extracted twice more with EA (2×150 mL). The combined organic extracts were dried over $Na_2SO_4$, filtered and concentrated to dryness. The residue was dried under HV to afford the title intermediate (11.1 g, 69 mmol) as a yellow solid.

$^1$H NMR (DMSO d6) δ: 11.75 (br s, 1H); 8.17 (s, 1H); 7.62 (d, J=8.4 Hz, 1H); 7.40 (d, J=8.4 Hz, 1H); 7.21 (t, J=8.4 Hz, 1H); 2.42 (s, 3H).

MS (ESI, m/z): 161.1 [M+H]$^+$.

A.iv. 2-chloro-8-methyl-quinoxaline:

A solution of intermediate A.iii (11.1 g, 69.5 mmol) in phosphorus oxychloride (80 mL) was heated at 110° C. during 2 h. After cooling to rt, the reaction mixture was poured onto ice (200 g). The aqueous layer was extracted with EA (2×200 mL). The combined extracts were washed with brine (100 mL), dried over $Na_2SO_4$, filtered and concentrated to dryness. The residue was chromatographed over silica gel (Hex-EA 1-1) to afford the title intermediate (12.5 g, 69.5 mmol) as a red solid.

$^1$H NMR (DMSO d6) δ: 8.99 (s, 1H); 7.97 (m, 1H); 7.80 (m, 2H); 2.68 (s, 3H).

MS (ESI, m/z): 179.2 [M+H]$^+$.

A.v. 2-methoxy-8-methyl-quinoxaline:

To a solution of intermediate A.iv (12.5 g, 69.5 mmol) in DMF (80 mL) was added sodium methoxide (9 g, 166 mmol). The reaction mixture was heated at 45° C. for 4 h. After cooling to rt, the reaction mixture was partitioned between water (10 mL) and EA (200 mL). The organic layer was washed once with water (100 mL), dried over $Na_2SO_4$, filtered and concentrated to dryness. The residue was chromatographed over silica gel (Hex-EA 1-4) to afford the title intermediate (10.2 g, 58.55 mmol) as a yellow solid.

$^1$H NMR (CDCl$_3$) δ: 8.48 (s, 1H); 7.88 (d, J=7.9 Hz, 1H); 7.55 (d, J=7.9 Hz, 1H); 7.47 (t, J=7.9 Hz, 1H); 4.12 (s, 3H); 2.69 (s, 3H).

MS (ESI, m/z): 175.4 [M+H]$^+$.

A.vi. 8-dibromomethyl-2-methoxy-quinoxaline:

To a solution of intermediate A.v (10.2 g) in CCl$_4$ (560 mL) were added AIBN (0.96 g) and NBS (25.9 g, 145.5 mmol). The reaction mixture was heated at 80° C. for 3 h. After cooling to rt, the reaction mixture was washed with water (200 mL) and the organic layer was dried over $Na_2SO_4$, filtered and concentrated in vacuo. The residue was triturated with MeOH to give, after drying under HV, the title dibromide (14.4 g, 43.3 mmol) as a slightly beige solid.

$^1$H NMR (DMSO d6) δ: 8.69 (s, 1H); 8.25 (dd, J=1.3, 7.5 Hz, 1H); 8.07 (dd, J=1.3, 8.3 Hz, 1H); 8.02 (s, 1H); 7.74 (dd, J=7.5, 8.3 Hz, 1H); 4.14 (s, 3H).

MS (ESI, m/z): 332.8 [M+H]$^+$.

A.vii. 3-methoxy-quinoxaline-5-carbaldehyde:

To a solution of intermediate A.vi (10.7 g, 32.2 mmol) in EtOH (330 mL) was added, at rt, a solution of silver nitrate (15 g) in water (70 mL). The reaction was stirred at rt for 1 h. The reaction mixture was diluted with MeCN (200 mL) and the solids were filtered off and the filtrate was concentrated in vacuo. The residue was filtered over a silica gel pad (eluent: EA) to afford the title aldehyde (6.2 g, 32.2 mmol) as a slightly yellow solid.

$^1$H NMR (DMSO d6) δ: 11.15 (s, 1H); 8.74 (s, 1H); 8.36 (dd, J=1.3, 8.1 Hz, 1H); 8.21 (dd, J=1.3, 7.9 Hz, 1H); 7.80 (dd, J=7.9, 8.1 Hz, 1H); 4.14 (s, 3H).

MS (ESI, m/z): 189.2 [M+H]$^+$.

Preparation B:
6-methoxy-[1,5]naphthyridine-4-carbaldehyde

B.i. 2-methoxy-8-styryl-[,5]naphthyridine:

Trifluoromethanesulfonic acid 6-methoxy-[1,5]naphthyridin-4-yl ester (1.5 g, 4.86 mmol), trans-phenylvinyl boronic acid (0.8 g, 5.35 mmol) and $K_2CO_3$ (0.9 g, 6.32 mmol) were introduced in a two-neck flask. The atmosphere was flushed with nitrogen. Dioxane (20 mL) and water (5 mL) were added. The mixture was stirred at rt for 5 min and (P(Ph)$_3$)$_4$Pd (0.28 g, 0.24 mmol) was added. The mixture was heated at reflux for 5 h. After cooling, the reaction mixture was diluted with EA (10 mL) and water (50 mL). The aq. layer was extracted with EA (2×100 mL). The combined org. extracts were concentrated to dryness. The residue was chromatographed over SiO$_2$ (Hex-EA 1-1) to afford the title alkene (1.26 g, 4.8 mmol) as an oil that crystallized on standing.

$^1$H NMR (DMSO d6) δ: 8.77 (d, J=4.7 Hz, 1H); 8.28 (d, J=9.0 Hz, 1H); 8.19 (d, J=16.7 Hz, 1H); 8.01 (d, J=4.7 Hz, 1H); 7.91 (d, J=16.7 Hz, 1H); 7.74 (m, 2H); 7.40-7.34 (m, 3H); 7.30 (d, J=9.0 Hz, 1H); 4.12 (s, 3H).

B.ii. 1-(6-methoxy-[1,5]naphthyridin-4-yl)-2-phenyl-ethane-1,2-diol:

To a mixture of intermediate B.i (1.26 g, 4.8 mmol) in 2-methyl-2-propanol (24 mL) and water (24 mL) were added methanesulfonamide (0.52 g) and AD-mix β® (7 g). The mixture was stirred at rt for 12 h. Sodium bisulfite (7.5 g) was added carefully and stirring was continued 20 min. The two layers were decanted and the aqueous layer was extracted with EA (2×100 mL). The combined organic layers were dried over $Na_2SO_4$, filtered and concentrated to dryness. The residue was triturated in Hex-EA (1-3, 30 mL) and the resulting solid was filtered off and dried in vacuo to afford the title diol (1.3 g) as a white solid.

MS (ESI, m/z): 297.1 [M+H$^+$].

B.iii. 6-methoxy-[1,5]naphthyridine-4-carbaldehyde:

To a solution of intermediate B.ii (1.3 g, 4.4 mmol) in acetone (15 mL) was added a solution of NaIO$_4$ (2.35 g, 10.96 mmol) in water (5 mL). The reaction mixture was stirred at rt for 30 min. The reaction mixture was diluted with THF (100 mL) and the solids were filtered off. The filtrate was concentrated to dryness and the residue was resuspended in water (100 mL), ether (10 mL) and Hex (100 mL). The slurry was stirred at rt for 15 min and filtered. The solids were washed with water and Hex. After drying, the title aldehyde (0.42 g) was recovered as a white solid.

$^1$H NMR (DMSO d6) δ: 11.25 (s, 1H); 9.02 (d, J=4.4 Hz, 1H); 8.42 (d, J=9.1 Hz, 1H); 7.92 (d, J=4.4 Hz, 1H); 7.40 (d, J=9.1 Hz, 1H); 4.11 (s, 3H).

Preparation C: 5-bromo-3-methoxyquinoline

C.i. 3,5-dibromoquinoline:

To concentrated $H_2SO_4$ (130 mL) was added dropwise at 0° C., over 80 min, 3-bromoquinoline (50 g) at a rate allowing the internal temperature to be maintained between 0° and 10° C. After the addition was complete, NBS (48 g) was added portionwise and the reaction mixture was stirred at rt overnight. The reaction mixture was poured onto ice (2 L) and the resulting solid was dissolved in DCM (600 mL). The aq. layer was further extracted with DCM (600 mL) and the combined extracts were washed with 1M NaOH (300 mL) and concentrated in vacuo. The residue was adsorbed on $SiO_2$ and the resulting dispersal was loaded on the top of a column and eluted with a DCM-Hex (1-1, 3 L), then DCM (3 L) and finally DCM-ether (1-1, 2 L). The title compound was recovered from the last fraction after evaporation to yield 40 g of a white solid.

$^1$H NMR ($CDCl_3$) δ: 8.94 (d, J=2.2 Hz, 1H); 8.73 (d, J=2.2 Hz, 1H); 8.08 (d, J=8.5 Hz, 1H); 7.88 (d, J=7.5 Hz, 1H); 7.62 (dd, J=7.5, 8.5 Hz, 1H).

C.ii. 5-bromo-3-methoxyquinoline:

To a mixture of sodium methoxide (14.5 g) in DMPU (350 mL) heated at 125° C., was added in one portion of intermediate C.i (34.5 g). The reaction was then heated at the same temperature for 1 h. The reaction mixture was then cooled to rt and poured onto ice (300 g). After the ice melt, the solid was filtered off and dried under vacuum. The filtrate was extracted with ether (4×150 mL). The combined extracts were washed with brine and dried over $Na_2SO_4$. After filtration, the solvent was evaporated and the residue purified over $SiO_2$ (Hex-EA 4-1) to afford a material that was pooled with the solid. The material was dissolved in DCM and dried over $Na_2SO_4$. After filtration and evaporation, the solid was further dried under HV to afford the title compound (24.5 g) as a beige solid.

$^1$H NMR ($CDCl_3$) δ: 8.68 (d, J=2.8 Hz, 1H); 8.03 (d, J=8.3 Hz, 1H); 7.80 (d, J=7.5 Hz, 1H); 7.72 (d, J=2.8 Hz, 1H); 7.42 (dd, J=7.5, 8.3 Hz, 1H); 4.02 (s, 3H).

MS (ESI, m/z): 239.7 [M+H$^+$].

Example 1 trans-4-(6-methoxy-quinolin-4-yloxymethyl)-cyclohexanecarboxylic acid (2,3-dihydro-benzo[1,4]dioxin-6-yl)-amide 1.i. trans-[4-(tert-butyl-dimethyl-silanyloxymethyl)-cyclohexyl]-methanol:

To a solution of trans-(4-hydroxymethyl-cyclohexyl)-methanol (50 g, 347 mmol) in DMF (700 mL) at rt was added sequentially imidazole (47.2 g, 693 mmol) and TBDMSCl (44.3 g, 294 mmol). The mixture was poured into water and the product extracted with ether. The combined organic extracts were dried over $MgSO_4$ and concentrated under reduced pressure. Chromatography over $SiO_2$ (Hex/EA 4:1, 2:1) gave the desired mono-protected compound as a colourless oil (40.1 g, 45% yield).

$^1$H NMR (DMSO d6) δ: 4.31 (t, J=5.4 Hz, 1H); 3.36 (d, J=6.1 Hz, 2H); 3.18 (t, J=5.7 Hz, 2H); 1.75-1.65 (m, 4H); 1.40-1.20 (m, 2H); 0.95-0.85 (m, 4H); 0.85 (s, 9H); 0.01 (s, 6H).

1.ii. trans-4-(tert-butyl-dimethyl-silanyloxymethyl)-cyclohexanecarboxylic acid:

A mixture of intermediate 1.i (14.1 g, 54.7 mmol), $RuCl_3.2H_2O$ (0.3 g, 0.025 eq.) and $NaIO_4$ (48 g, 4.1 eq.) in $CCl_4$ (100 mL), MeCN (100 mL) and water (150 mL) was vigorously stirred at rt for 2 h. DCM (300 mL) was added and the two phases separated. The aq. phase was once more extracted with DCM and the combined org. extracts were dried over $MgSO_4$ and concentrated. The residue was purified by chromatography over $SiO_2$ (Hex/EA 4:1, 2:1) to give 8.3 g (55.5% yield) of acid as a greyish solid.

$^1$H NMR (DMSO d6) δ: 11.96 (s, 1H); 3.38 (d, J=6.3 Hz, 2H); 2.49 (m, 1H); 1.88 (m, 2H); 1.72 (m, 2H); 1.4-1.2 (m, 4H); 1.0-0.8 (m, 4H); 0.84 (s, 9H); 0.02 (s, 6H).

MS (ESI, m/z): 271.0 [M−H$^-$].

1.iii. trans-4-(tert-butyl-dimethyl-silanyloxymethyl)-cyclohexanecarboxylic acid (2,3-dihydro-benzo[1,4]dioxin-6-yl)-amide:

A solution of TPPA (50% in EA, 2.16 mL) was added dropwise to a stirred solution of intermediate 1.ii (0.988 g, 3.62 mmol), 2,3-dihydro-benzo[1,4]dioxin-6-ylamine (0.555 g, 1 eq.) and DIPEA (1.89 mL, 3 eq.) in DCM (20 mL) at rt. The mixture was stirred at rt for 2 h, diluted with DCM (20 mL) and washed with 1M HCl (20 mL) and water (40 mL), dried over $MgSO_4$ and concentrated. Chromatography over $SiO_2$ (Hex/EA 2:1) gave the product (1.14 g, 77% yield) as a beige solid.

$^1$H NMR ($CDCl_3$) δ: 7.22 (d, J=2.4 Hz, 1H); 6.96 (br, s, 1H); 6.85 (dd, J=2.4, 8.7 Hz, 1H); 6.73 (d, J=8.7 Hz, 1H); 4.19 (s, 4H); 3.38 (d, J=6.3 Hz, 2H); 2.10 (m, 1H); 1.95 (m, 2H); 1.85 (m, 2H); 1.6-1.4 (m, 4H); 1.0-0.8 (m, 4H); 0.84 (s, 9H); 0.02 (s, 6H).

MS (ESI, m/z): 406.0 [M+H$^+$].

1.iv. trans-4-hydroxymethyl-cyclohexanecarboxylic acid (2,3-dihydro-benzo[1,4]dioxin-6-yl)-amide:

A solution of intermediate 1.iii (1.14 g, 2.81 mmol) in THF (20 mL) was treated with TBAF (1M solution in THF, 2.8 mL, 1 eq). The mixture was stirred at rt for 2 h, concentrated in vacuo and purified by chromatography over $SiO_2$ (Hex/EA 1:1, EA) to give the desired compound (0.73 g, 89% yield) as a yellowish solid.

$^1$H NMR (DMSO d6) δ: 9.63 (s, 1H); 7.22 (d, J=2.4 Hz, 1H); 7.00 (dd, J=2.4, 8.7 Hz, 1H); 6.78 (d, J=8.7 Hz, 1H); 4.41 (t, J=5.4 Hz, 1H); 4.23 (m, 4H); 3.26 (t, J=5.8 Hz, 2H); 2.2 (m, 1H); 1.9-1.8 (m, 4H); 1.6-1.4 (m, 2H); 1.1-0.95 (m, 2H).

MS (ESI, m/z): 292.2 [M+H$^+$].

1.v. trans-4-(6-methoxy-quinolin-4-yloxymethyl)-cyclohexanecarboxylic acid (2,3-dihydro-benzo[1,4]dioxin-6-yl)-amide:

DIAD (0.286 mL, 1.2 eq.) was added dropwise to a suspension of intermediate 1.iv (0.35 g, 1.2 mmol), 6-methoxy-quinolin-4-ol (0.3 g, 1 eq.) and $PPh_3$ (0.378 g, 1.2 eq.). The resulting brownish solution was stirred at rt for 3 h, concentrated in vacuo and purified by chromatography over $SiO_2$ (EA, EA/MeOH 9:1). The purest fractions were pooled, concentrated and crystallised from MeOH/ether to the title compound (0.22 g, 40% yield) as a beige solid.

$^1$H NMR (DMSO d6) δ: 9.68 (s, 1H); 8.57 (d, J=5.2 Hz, 1H); 7.87 (d, J=9.6 Hz, 1H); 7.5-7.4 (m, 2H); 7.25 (d, J=2.4 Hz, 1H); 7.00-6.95 (m, 2H); 6.77 (d, J=8.7 Hz, 1H); 4.20-(m, 4H); 4.10 (d, J=5.8 Hz, 2H); 3.90 (s, 3H); 2.30 (m, 1H); 2.1-1.9 (m, 4H); 1.6-1.4 (m, 2H); 1.3-1.1 (m, 2H).

MS (ESI, m/z): 448.7 [M+H$^+$].

Example 2 trans-4-(6-methoxy-quinazolin-4-yloxymethyl)-cyclohexanecarboxylic acid (2,3-dihydro-benzo[1,4]dioxin-6-yl)-amide To a solution of intermediate 1.iv (0.1 g, 0.34 mmol) and 4-chloro-6-methoxy-quinazoline (0.067 g, 1 eq.) in DMF (3 mL) was added a NaH dispersion (55% in mineral oil, 0.03 g, 2 eq.). The mixture was stirred at rt for 2 h and partitioned between water and EA. The org. phase was washed with water and brine, dried over MgSO$_4$ and concentrated. The product was crystallised from ether and was obtained as a colourless solid (0.094 g, 61% yield).

$^1$H NMR (DMSO d6) δ: 9.67 (s, 1H); 8.67 (s, 1H); 7.88 (d, J=9.1 Hz, 1H); 7.60 (dd, J=2.9, 9.1 Hz, 1H); 7.42 (d, J=2.9 Hz, 1H); 7.24 (d, J=2.4 Hz, 1H); 6.98 (dd, J=2.5, 8.8 Hz, 1H); 6.75 (d, J=8.7 Hz, 1H); 4.41 (d, J=5.8 Hz, 2H); 4.20 (m, 4H); 3.90 (s, 3H); 2.30 (m, 1H); 2.1-1.8 (m, 4H); 1.6-1.4 (m, 2H); 1.3-1.1 (m, 2H).

MS (ESI, m/z): 449.7 [M+H$^+$].

Example 3 trans-4-(6-methoxy-quinolin-4-yloxymethyl)-cyclohexanecarboxylic acid (3-oxo-3,4-dihydro-2H-benzo[1,4]thiazin-6-yl)-amide 3.i. 6-amino-4H-benzo[1,4]thiazin-3-one:

A NaH dispersion (55% in mineral oil, 2.81 g, 1 eq.) was added portionwise to a solution of methyl thioglycolate (5.3 g, 50 mmol) and 1-chloro-2,4-dinitro-benzene (10.1 g, 50 mmol) in DMF (100 mL) at 0° C. The mixture (dark red) was stirred at 0° C. for 1 h and at rt for 1 h, poured onto ice and extracted with ether (2×200 mL). The combined org. extracts were washed with water, filtered over a pad of SiO$_2$ and concentrated. The residue was suspended in ether and filtered again (8 g of intermediate). Iron powder (19.7 g, 353 mmol) was added portionwise to a solution of above intermediate in AcOH (100 mL) at 60° C. The mixture was stirred at this temperature for 1 h, cooled to rt and filtered over Celite. The filtercake was washed with AcOH and the filtrate concentrated under reduced pressure. The brown residue was partitioned between sat. aq. NaHCO$_3$ and EA. The combined org. extracts were washed with sat. aq. NaHCO$_3$, dried over MgSO$_4$ and concentrated. The residue was suspended in ether and filtered to give 4.25 g (46% yield) of title aniline as a beige solid.

$^1$H NMR (DMSO d6) δ: 10.27 (s, 1H); 6.90 (d, J=8 Hz, 1H); 6.25-6.15 (m, 2H); 5.20 (s, 2H); 3.11 (s, 2H).

3.ii. trans-4-(tert-butyl-dimethyl-silanyloxymethyl)-cyclohexanecarboxylic acid (3-oxo-3,4-dihydro-2H-benzo[1,4]thiazin-6-yl)-amide:

A solution of TPPA (50% in EA, 2.16 mL) was added dropwise to a stirred solution of intermediate 1.ii (0.988 g, 3.62 mmol), intermediate 3.i (0.654 g, 1 eq.) and DIPEA (1.89 mL, 3 eq.) in DCM (20 mL) at rt. The mixture was stirred at rt for 2 h, diluted with DCM (20 mL), washed with 1M HCl (20 mL) and water (40 mL), dried over MgSO$_4$ and concentrated. Chromatography over SiO$_2$ (Hex/EA 2:1) gave the product (1.43 g, 91% yield) as a beige solid.

$^1$H NMR (DMSO d6) δ: 9.84 (s, 1H); 7.37 (m, 1H); 7.15 (m, 2H); 3.35 (m, 4H); 2.20 (m, 1H); 1.95 (m, 2H); 1.85 (m, 2H); 1.6-1.4 (m, 4H); 1.0-0.8 (m, 4H); 0.84 (s, 9H); 0.02 (s, 6H).

MS (ESI, m/z): 434.9 [M+H$^+$].

3.iii. trans-4-hydroxymethyl-cyclohexanecarboxylic acid (3-oxo-3,4-dihydro-2H-benzo[1,4]thiazin-6-yl)-amide:

Starting from intermediate 3.ii (1.43 g, 3.3 mmol) and following the procedure of Example 1, step 1.iv the desired alcohol (0.3 g, 28% yield) was recovered as a beige solid after chromatography over SiO$_2$ (Hex/EA 1:1, EA).

$^1$H NMR (CDCl$_3$) δ: 7.22 (d, J=2.4 Hz, 1H); 6.96 (br, s, 1H); 6.85 (dd, J=2.4, 8.7 Hz, 1H); 6.73 (d, J=8.7 Hz, 1H); 4.19 (s, 4H); 3.38 (d, J=6.3 Hz, 2H); 2.10 (m, 1H); 1.95 (m, 2H); 1.85 (m, 2H); 1.6-1.4 (m, 4H); 1.0-0.8 (m, 4H); 0.84 (s, 9H); 0.02 (s, 6H).

MS (ESI, m/z): 406.0 [M+H$^+$].

3.iv. trans-4-(6-methoxy-quinolin-4-yloxymethyl)-cyclohexanecarboxylic acid (3-oxo-3,4-dihydro-2H-benzo[1,4]thiazin-6-yl)-amide:

Starting from intermediate 3.iii (0.2 g, 0.62 mmol) and 6-methoxy-quinolin-4-ol (0.11 g, 0.62 mmol) and following the procedure of Example 1, step 1.v, the title compound was isolated after chromatography over SiO$_2$ (DCM/MeOH 9:1 containing 1% NH$_4$OH) as a beige solid (0.11 g, 38% yield).

$^1$H NMR (DMSO d6) δ: 10.56 (s, 1H); 9.92 (s, 1H); 8.57 (d, J=5.2 Hz, 1H); 7.87 (d, J=9.6 Hz, 1H); 7.45-7.35 (m, 2H); 7.20-7.15 (m, 2H); 6.99 (d, J=5.3 Hz, 1H); 4.10 (d, J=5.3 Hz, 2H); 3.90 (s, 3H); 3.42 (s, 2H); 3.30 (s, 3H); 2.36 (m, 1H); 2.1-1.9 (m, 4H); 1.6-1.4 (m, 2H); 1.3-1.1 (m, 2H).

MS (ESI, m/z): 477.8 [M+H$^+$].

Example 4 trans-4-(6-methoxy-quinazolin-4-yloxymethyl)-cyclohexanecarboxylic acid (3-oxo-3,4-dihydro-2H-benzo[1,4]thiazin-6-yl)-amide To a solution of intermediate 3.iv (0.09 g, 0.28 mmol) and 4-chloro-6-methoxy-quinazoline (0.055 g, 1 eq.) in DMF (3 mL) was added a NaH dispersion (55% in mineral oil, 0.03 g, 2 eq). The mixture was stirred at rt for 2 h, partitioned between water and EA. The org. phase was washed with water and brine, dried over MgSO$_4$ and concentrated. The product was crystallised from ether and was obtained as a colourless solid (0.036 g, 27% yield).

$^1$H NMR (DMSO d6) δ: 10.53 (s, 1H); 9.89 (s, 1H); 8.64 (s, 1H); 7.83 (d, J=9.1 Hz, 1H); 7.56 (dd, J=2.9, 9.1 7.38 (m, 2H); 7.15 (m, 2H); 4.39 (d, J=5.8 Hz, 2H); 3.90 (s, 3H); 3.38 (s, 2H); 2.30 (m, 1H); 2.1-1.8 (m, 4H); 1.6-1.4 (m, 2H); 1.3-1.1 (m, 2H).

MS (ESI, m/z): 478.7 [M+H$^+$].

Example 5 trans-4-[2-(6-methoxy-[1,5]naphthyridin-4-yl)-ethyl]-cyclohexanecarboxylic acid (2,3-dihydro-benzo[1,4]dioxin-6-yl)-amide 5.i. trans-4-(tert-butyl-dimethyl-silanyloxymethyl)-cyclohexanecarboxylic acid methyl ester:

Intermediate 1.ii (5 g, 18.3 mmol) was dissolved in benzene/MeOH (1:1, 60 mL) and cooled to 2° C. At this temperature a solution of TMS diazomethane (2M in ether, 9.1 mL) was added. The mixture was stirred at 2° C. for 2 h, more TMS diazomethane (5 mL) was added and stirring continued for another 4 h. The volatiles were removed under reduced pressure and the residue was purified by chromatography over SiO$_2$ (Hex/EA 4:1) to give the desired ester (3.9 g, 74% yield) as a yellowish oil.

$^1$H NMR (DMSO d6) δ: 3.55 (s, 3H); 3.36 (d, J=6.3 Hz, 2H); 2.19 (m, 1H); 1.87 (m, 2H); 1.72 (m, 2H); 1.4-1.2 (m, 2H); 1.0-0.8 (m, 2H); 0.84 (s, 9H); 0.00 (s, 6H).

5.ii. trans-4-hydroxymethyl-cyclohexanecarboxylic acid methyl ester:

TBAF (1M solution in THF, 14.4 mL) was added to a solution of intermediate 5.i (3.9 g, 13.6 mmol) in THF (50 mL) at rt. The mixture was stirred at rt for 3 h, concentrated in vacuo and the residue was purified by chromatography over SiO$_2$ (Hex/EA 2:1, 1:1) to give the desired compound (1.62 g, 69% yield) as a yellowish oil.

¹H NMR (DMSO d6) δ: 4.42 (t, J=5.3 Hz, 1H); 3.62 (s, 3H); 3.23 (t, J=5.9 Hz, 2H); 2.26 (m, 1H); 1.93 (m, 2H); 1.79 (m, 2H); 1.4-1.2 (m, 2H); 1.0-0.8 (m, 2H).

5.iii. trans-4-formyl-cyclohexanecarboxylic acid methyl ester:

Oxalyl chloride (0.904 mL, 10.7 mmol) was added dropwise to a solution of DMSO (1.49 mL, 21 mmol) in DCM (35 mL) at −78° C. After 15 min, a solution of intermediate 5.ii (1.6 g, 9.3 mmol) in DCM (15 mL) was added dropwise and the mixture was stirred at −78° C. for another 2.5 h. TEA (13 mL) was added and the mixture gradually warmed to rt. A sat. aq. solution of $NH_4Cl$ was added and the two phases separated. The aq. phase was extracted once more with DCM and the combined org. phases were washed with brine, dried over $MgSO_4$ and concentrated. The residue was purified by chromatography over $SiO_2$ (Hex/EA 4:1, 2:1) to give the desired aldehyde (1.2 g, 76% yield) as a yellowish oil.

¹H NMR ($CDCl_3$) δ: 9.65 (s, 1H); 3.69 (s, 3H); 2.35-2.20 (m, 2H); 2.15-2.05 (m, 4H); 1.60-1.20 (m, 4H).

5.iv. trans-4-ethynyl-cyclohexanecarboxylic acid methyl ester:

$K_2CO_3$ (3.4 g, 24.7 mmol) was added to a solution of p-toluenesulfonyl azide (1.97 g, 9.9 mmol) and dimethyl (2-oxo-propyl)phosphonate (1.73 g, 9.9 mmol) in MeCN (110 mL) at rt. The mixture was stirred at rt for 2 h before addition of a solution of intermediate 5.iii (1.2 g, 7 mmol) in MeOH (15.5 mL). The mixture was stirred at rt overnight, concentrated in vacuo and partitioned between DCM and water. The organic phase was dried over $MgSO_4$ and concentrated. The residue was purified by chromatography over $SiO_2$ (Hex/EA 4:1) to give the title alkyne (0.45 g, 38% yield) as a colourless oil.

¹H NMR (DMSO d6) δ: 3.58 (s, 3H); 2.87 (d, J=2.4 Hz, 1H); 2.4-2.2 (m, 2H); 1.95-1.80 (m, 4H); 1.45-1.30 (m, 4H).

5.v. trans-4-(6-methoxy-[1,5]naphthyridin-4-ylethynyl)-cyclohexanecarboxylic acid methyl ester:

A solution of alkyne 5.iv (0.45 g, 2.7 mmol), 8-bromo-2-methoxy-[1,5]naphthyridine (647 mg, 1 eq.) and TEA (2.26 mL) in DMF (45 mL) was purged with $N_2$ during 15 min. and $Pd(PPh_3)_2Cl_2$ (0.095 g, 0.05 eq.) and CuI (0.056 g, 0.11 eq.) were added and the mixture was stirred at rt for 2 h and at 50° C. for 4 h. The mixture was partitioned between EA and water. The aq. phase was extracted with EA and the combined org. extracts were washed with water and brine, dried over $MgSO_4$ and concentrated. The residue was purified by chromatography over $SiO_2$ (Hex/EA 9:1, 2:1) to give the desired compound (0.35 g, 40% yield) as a yellowish solid.

¹H NMR (DMSO d6) δ: 8.87 (br, 1H); 8.25 (d, J=9.1 Hz, 1H); 7.60 (br, 1H); 7.16 (d, J=9.1 Hz, 1H); 4.15 (s, 3H); 3.71 (s, 3H); 2.69 (m, 1H); 2.39 (m, 1H); 2.30-2.25 (m, 2H); 2.20-2.05 (m, 2H); 1.75-1.50 (m, 4H).

5.vi. trans-4-[2-(6-methoxy-[1,5]naphthyridin-4-yl)-ethyl]-cyclohexanecarboxylic acid methyl ester:

A solution of intermediate 5.v (0.35 g, 1 mmol) in MeOH (10 mL) was hydrogenated over Pd/C (10%, 0.115 g) for 2 h. The catalyst was removed by filtration over Celite and the solvents were removed in vacuo to yield the title intermediate (0.31 g, 87% yield) as a yellowish oil.

¹H NMR ($CDCl_3$) δ: 8.68 (m, 2H); 7.61 (m, 7.28 (d, J=8.9 Hz, 1H); 4.15 (s, 3H); 3.70 (s, 3H); 3.35-3.25 (m, 2H); 2.29 (m, 1H); 2.05-1.9 (m, 4H); 1.75-1.65 (m, 2H); 1.60-1.35 (m, 2H); 1.20-1.00 (m, 2H).

5.vii. trans-4-[2-(6-ethoxy-[1,5]naphthyridin-4-yl)-ethyl]-cyclohexanecarboxylic acid:

A solution of intermediate 5.vi (0.31 g, 0.94 mmol) in $MeOH/THF/H_2O$ (2:2:1) was treated with LiOH hydrate (0.047 g, 1.2 eq.). The mixture was stirred at rt overnight. The volatiles were removed under reduced pressure and the residue was taken up in water. The pH was adjusted to 4 with 1M HCl and the precipitate filtered off and dried under HV to give 0.27 g (90% yield) of title acid as a colourless solid.

¹H NMR (DMSO d6) δ: 9.00 (d, J=5.4 Hz, 1H); 8.68 (d, J=9.2 Hz, 1H); 8.04 (d, J=5.4 Hz, 1H); 7.58 (d, J=9.2 Hz, 1H); 4.09 (s, 3H); 3.35-3.25 (m, 2H); 2.15 (m, 1H); 1.95-1.80 (m, 4H); 1.75-1.60 (m, 2H); 1.4-1.2 (m, 3H); 1.05-0.95 (m, 2H).

5.viii. trans-4-[2-(6-methoxy-[1,5]naphthyridin-4-yl)-ethyl]-cyclohexanecarboxylic acid (2,3-dihydro-benzo[1,4]dioxin-6-yl)-amide:

Starting from acid 5.vii (0.135 g, 0.43 mmol) and 2,3-dihydro-benzo[1,4]dioxin-6-ylamine (0.065 g, 1 eq.) and following the procedure of Example 1, step 1.iii, the title compound (0.04 g, 21% yield) was obtained after chromatography over $SiO_2$ (Hex/EA 1:1, EA) as a colourless solid.

¹H NMR (DMSO d6) δ: 9.62 (s, 1H); 8.67 (d, J=5.4 Hz, 1H); 8.24 (d, J=9.2 Hz, 1H); 7.56 (d, J=5.4 Hz, 1H); 7.30-7.20 (m, 2H); 6.97 (m, 1H); 6.76 (m, 1H); 4.20 (m, 4H); 4.02 (s, 3H); 3.20-3.12 (m, 2H); 2.23 (m, 1H); 2.00-1.80 (m, 4H); 1.70-1.60 (m, 2H); 1.5-1.2 (m, 3H); 1.10-0.95 (m, 2H).

MS (ESI, m/z): 447.8 [M+H⁺].

Example 6 trans-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide Starting from intermediate 5.vii (0.135 g, 0.43 mmol) and intermediate 3.i (0.077 g, 1 eq.) and following the procedure of Example 1, step 1.iii, the title compound (0.022 g, 11% yield) was obtained after chromatography over $SiO_2$ (Hex/EA 1:1, EA) as a brownish solid.

¹H NMR (DMSO d6) δ: 10.56 (s, 1H); 9.88 (s, 1H); 8.67 (d, J=5.4 Hz, 1H); 8.24 (d, J=9.2 Hz, 1H); 7.56 (d, J=5.4 Hz, 1H); 7.40 (s, 1H); 7.30-7.10 (m, 3H); 4.04 (s, 3H); 3.38 (s, 2H); 3.20-3.12 (m, 2H); 2.28 (m, 1H); 2.00-1.75 (m, 4H); 1.70-1.60 (m, 2H); 1.5-1.2 (m, 3H); 1.10-0.95 (m, 2H).

Example 7 cis-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide 7.i. 4-oxo-cyclohexanecarboxylic acid ethyl ester:

To a solution of oxalyl chloride (6 mL, 68.8 mmol) in DCM (100 mL) at −78° C. was added dropwise a solution of DMSO (6.4 mL, 90 mmol) in DCM (20 mL). The mixture was stirred at this temperature for 15 min before the dropwise addition of a solution of ethyl 4-hydroxycyclohexane carboxylate (4.8 mL, 30 mmol) in DCM (20 mL). The mixture was stirred at −78° C. for 3 h before addition of TEA (29.3 mL, 210 mmol) in DCM (20 mL). The mixture was then gradually warmed to rt, washed with a sat. aq. $NH_4Cl$ solution and brine, dried over $MgSO_4$ and concentrated. The residue was purified by chromatography over $SiO_2$ (Hex/EA 1:1) to give the title ketone (4.6 g, 90% yield) as a colourless oil.

¹H NMR (CDCl₃) δ: 4.19 (q, J=7.1 Hz, 2H); 2.80-2.70 (m, 1H); 2.55-2.45 (m, 2H); 2.40-2.30 (m, 2H); 2.25-2.10 (m, 2H); 2.05-2.00 (m, 2H); 1.29 (t, J=7.1 Hz, 3H).

7.ii. cis- and trans-4-hydroxy-4-trimethylsilanylethynyl-cyclohexanecarboxylic acid ethyl ester:

To a solution of TMS acetylene (1.9 mL, 13.5 mmol) in THF (30 mL) at −78° C. was added dropwise n-BuLi (2.5M solution in Hex, 5.4 mL). The mixture was stirred at this temperature for 15 min before the dropwise addition of a solution of intermediate 7.i (2.28 g, 13.2 mmol) in THF (5 mL). The mixture was stirred at −78° C. for 3 h and then slowly warmed to rt. The mixture was diluted with ether, washed with sat. aq. NH₄Cl solution, dried over MgSO₄ and concentrated under reduced pressure. The residue was purified by chromatography over SiO₂ (Hex/EA 3:1) to give first the cis adduct (1 g, 27% yield) and then the trans adduct (1 g, 27% yield) as colourless oils (1 g of mixed fractions was also recovered).

Data for the cis adduct:
¹H NMR (CDCl₃) δ: 4.19 (q, J=7.1 Hz, 2H); 2.34 (m, 1H); 2.00-1.70 (m, 9H); 1.29 (t, J=7.1 Hz, 3H); 0.15 (s, 9H).

Data for the trans adduct:
¹H NMR (CDCl₃) δ: 4.15 (q, J=7.1 Hz, 2H); 2.22 (m, 1H); 2.00-1.90 (m, 5H); 1.85-1.70 (m, 2H); 1.65-1.50 (m, 2H); 1.25 (t, J=7.1 Hz, 3H); 0.16 (s, 9H).

7.iii. cis-4-ethynyl-4-hydroxy-cyclohexanecarboxylic acid ethyl ester:

K₂CO₃ (0.515 g, 3.7 mmol) was added to a solution of the cis adduct of step 7.ii (1 g, 3.7 mmol) in MeOH. The mixture was stirred at rt overnight, filtered over Celite and the filtrate was concentrated in vacuo. The residue was purified by chromatography over SiO₂ (Hex/EA 2:1) to give the desired compound (0.56 g, 77% yield) as a colourless oil.

¹H NMR (CDCl₃) δ: 4.10 (q, J=7.1 Hz, 2H); 2.43 (s, 1H); 2.34 (m, 1H); 2.00-1.60 (m, 9H); 1.29 (t, J=7.1 Hz, 3H).

7.iv. cis-4-hydroxy-4-(6-methoxy-[1,5]naphthyridin-4-yl-ethynyl)-cyclohexanecarboxylic acid ethyl ester:

N₂ was bubbled for 10 min through a solution of intermediate 7.iii (0.563 g, 2.87 mmol) and trifluoro-methanesulfonic acid 6-methoxy-[1,5]naphthyridin-4-yl ester (0.884 g, 2.87 mmol) in DMF (10 mL) and TEA (2.4 mL). PdCl₂(PPh₃)₂ (0.1 g) and CuI (0.055 g) were added and the mixture stirred at rt for 2 h. The mixture was partitioned between water and EA. The org. layer was washed several times with water and brine, dried over MgSO₄ and concentrated. The residue was purified by chromatography over SiO₂ (Hex/EA 1:1, EA) to give the desired product (0.89 g, 88% yield) as a yellowish foam.

¹H NMR (DMSO d6) δ: 8.75 (d, J=4.5 Hz, 1H); 8.29 (d, J=9.1 Hz, 1H); 7.69 (d, J=4.5 Hz, 1H); 7.31 (d, J=9.1 Hz, 1H); 4.10-4.00 (m, 5H); 2.46 (m, 1H); 2.0-1.7 (m, 9H); 1.19 (t, J=7.1 Hz, 3H).

MS (ESI, m/z): 354.9 [M+H⁺].

7.v. cis-4-hydroxy-4-[2-(6-methoxy-[1,5]naphthyridin-4-yl)-ethyl]-cyclohexanecarboxylic acid ethyl ester:

A solution of intermediate 7.iv (0.89 g, 2.5 mmol) in THF/EtOH (1:1, 20 mL) was hydrogenated over Pd/C (10%, 134 mg) at atmospheric pressure for 2 h. The catalyst was filtered off over Celite and the filtrate was concentrated in vacuo. The residue was purified by chromatography over SiO₂ (Hex/EA 1:1, EA) to give the title compound as a yellowish solid (0.83 g, 91% yield).

¹H NMR (CDCl₃) δ: 8.59 (d, J=4.5 Hz, 1H); 8.13 (d, J=9.1 Hz, 1H); 7.33 (d, J=4.5 Hz, 1H); 7.04 (d, J=9.1 Hz, 1H); 4.05 (t, J=7.1 Hz, 2H); 4.00 (s, 3H); 3.41 (s, 1H); 3.25-3.15 (m, 2H); 2.20 (m, 1H); 1.90-1.70 (m, 6H); 1.50-1.30 (m, 2H); 1.16 (t, J=7.1 Hz, 3H).

MS (ESI, m/z): 360.4 [M+H⁺].

7.vi. cis-4-hydroxy-4-[2-(6-ethoxy-[1,5]naphthyridin-4-yl)-ethyl]-cyclohexanecarboxylic acid:

LiOH hydrate (0.146 g, 3.5 mmol) was added to a solution of intermediate 7.v (0.83 g, 2.3 mmol) in THF/MeOH/H₂O (2:2:1, 20 mL). The mixture was stirred at rt for 72 h, concentrated in vacuo and partitioned between water and EA, the aqueous layer was acidified to pH 3 using 1M HCl and the resulting precipitate was collected by filtration. After drying under HV, the title acid (0.6 g, 78% yield) was obtained as a colourless solid.

¹H NMR (DMSO d6) δ: 8.66 (d, J=4.5 Hz, 1H); 8.24 (d, J=9.1 Hz, 1H); 7.51 (d, J=4.5 Hz, 1H); 7.24 (d, J=9.1 Hz, 1H); 4.14 (s, 1H); 4.03 (s, 3H); 3.2-3.1 (m, 2H); 2.15 (m, 1H); 1.80-1.60 (m, 8H); 1.50-1.30 (m, 2H).

MS (ESI, m/z): 330.8 [M+H⁺].

7.vii. cis-4-hydroxy-4-[2-(6-ethoxy-[1,5]naphthyridin-4-yl)-ethyl]-cyclohexanecarboxylic acid (2,3-dihydro-benzo[1,4]dioxin-6-yl)-amide:

Starting from intermediate 7.vi (0.2 g, 0.6 mmol) and 2,3-dihydro-benzo[1,4]dioxin-6-ylamine (0.092 g, 1 eq.) and following the procedure of Example 1, step 1.iii, the title compound was obtained as a colourless foam (0.088 g, 32% yield) after chromatography over SiO₂ (DCM/MeOH 19:1).

¹H NMR (DMSO d6) δ: 9.62 (s, 1H); 8.66 (d, J=4.5 Hz, 1H); 8.24 (d, J=9.1 Hz, 1H); 7.53 (d, J=4.5 Hz, 1H); 7.26 (d, J=9.1 Hz, 1H); 7.26 (d, J=2.4 Hz, 1H); 6.98 (dd, J=2.4, 8.7 Hz, 1H); 6.75 (d, J=8.7 Hz, 1H); 4.20 (m, 4H); 4.14 (s, 1H); 4.03 (s, 3H); 3.20-3.10 (m, 2H); 2.15 (m, 1H); 1.90-1.70 (m, 5H); 1.6-1.5 (m, 2H); 1.50-1.30 (m, 2H).

MS (ESI, m/z): 464.3 [M+H⁺].

Example 8 cis-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide Starting from intermediate 7.vi (0.2 g, 0.6 mmol) and intermediate 3.i (0.109 g, 1 eq.) and following the procedure of Example 1, step 1.iii, the title compound was obtained as a colourless foam (0.065 g, 22% yield) after chromatography over SiO₂ (DCM/MeOH 19:1).

¹H NMR (DMSO d6) δ: 10.57 (s, 1H); 9.88 (s, 1H); 8.66 (d, J=4.5 Hz, 1H); 8.24 (d, J=9.1 Hz, 1H); 7.53 (d, J=4.5 Hz, 1H); 7.44 (d, J=1.1 Hz, 1H); 7.26 (d, J=9.1 Hz, 1H); 7.19 (m, 2H); 4.16 (s, 1H); 4.03 (s, 3H); 3.41 (s, 2H); 2.31 (m, 1H); 1.95-1.25 (m, 9H).

MS (ESI, m/z): 492.7 [M+H⁺].

Example 9 trans-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide Starting from intermediate 7.ii (trans isomer, 1 g) and following successively the procedures of Example 7, steps 7.iii to 7.vi and of Example 1, step 1.iii, the title compound (0.17 g, 73% yield) was isolated as a colourless oil.

¹H NMR (DMSO d6) δ: 9.62 (s, 1H); 8.66 (d, J=4.5 Hz, 1H); 8.24 (d, J=9.1 Hz, 1H); 7.53 (d, J=4.5 Hz, 1H); 7.26-7.22

(m, 2H); 6.98 (dd, J=2.4, 8.7 Hz, 1H); 6.75 (d, J=8.7 Hz, 1H); 4.40 (s, 1H); 4.20 (m, 4H); 4.06 (s, 3H); 3.2-3.1 (m, 2H); 2.30 (m, 1H); 1.95-1.30 (m, 9H).
MS (ESI, m/z): 464.2 [M+H$^+$].

Example 10 trans-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide Starting form intermediate 7.ii (trans isomer, 1 g) and following successively the procedures of Example 7, steps 7.iii to 7.vi and of Example 8, the title compound (0.136 g, 55% yield) was isolated as a colourless solid.
$^1$H NMR (DMSO d6) δ: 10.57 (s, 1H); 9.89 (s, 1H); 8.66 (d, J=4.5 Hz, 1H); 8.24 (d, J=9.1 Hz, 1H); 7.53 (d, J=4.5 Hz, 1H); 7.41 (d, J=1.1 Hz, 1H); 7.26 (d, J=9.1 Hz, 1H); 7.20 (d, J=8.5 Hz, 1H); 7.14 (dd, J=1.1, 8.5 Hz, 1H); 4.40 (s, 1H); 4.06 (s, 3H); 3.33 (s, 2H); 2.35 (m, 1H); 1.95-1.35 (m, 9H).
MS (ESI, m/z): 492.8 [M+H$^+$].

Example 11

(2RS)-1-[2-hydroxy-2-(6-methoxy-quinolin-4-yl)-ethyl]-piperidine-4-carboxylic acid (2,3-dihydro-benzo[1,4]dioxin-6-yl)-amide 11.i. Piperidine-1,4-dicarboxylic acid mono-tert-butyl ester:
To a solution of isonipecotic acid (12.9 g, 100 mmol) in dioxane (100 mL) and water (100 mL) was slowly added a solution of Boc$_2$O (24 g, 1.1 eq.) in dioxane (100 mL). After 15 min, 1M NaOH (100 mL) was added and the mixture stirred at rt overnight. The mixture was concentrated in vacuo and the residue partitioned between ether and 1M HCl (120 mL). The aq. phase was extracted with ether (2×200 mL) and the combined org. extracts were washed with brine, dried over MgSO$_4$ and concentrated. The expected compound was isolated as a colourless solid (22.4 g, 97% yield) and used as such in the next step.
$^1$H NMR (DMSO d6) δ: 12.5 (s, 1H); 3.83 (m, 2H); 2.82 (m, 2H); 2.40 (m, 1H); 1.78 (m, 2H); 1.39 (s, 9H); 1.34 (m, 2H).

11.ii. 4-(2,3-dihydro-benzo[1,4]dioxin-6-ylcarbamoyl)-piperidine-1-carboxylic acid tert-butyl ester:
Starting from intermediate 11.i (0.23 g, 1 mmol) and 2,3-dihydro-benzo[1,4]dioxin-6-ylamine (0.151 g, 1 eq.) and following the procedure from Example 1, step 1.iii, the title compound (0.36 g, 100% yield) was obtained as a colourless oil.
MS (ESI, m/z): 363.0 [M+H$^+$].

11.iii. Piperidine-4-carboxylic acid (2,3-dihydro-benzo[1,4]dioxin-6-yl)-amide:
A solution of intermediate 11.ii (0.36 g, 1 mmol) in DCM (8 mL) was treated with TFA (2 mL). The mixture was stirred at rt for 1 h, concentrated in vacuo, partitioned between DCM and NH$_4$OH. The org. layer was washed with water and brine, dried over MgSO$_4$ and concentrated. The title compound was isolated as a colourless solid (0.2 g, 76% yield).
MS (ESI, m/z): 262.8 [M+H$^+$].

11.iv. (2RS)-1-[2-hydroxy-2-(6-methoxy-quinolin-4-yl)-ethyl]-piperidine-4-carboxylic acid (2,3-dihydro-benzo[1,4]dioxin-6-yl)-amide:
A mixture of intermediate 11.iii (0.131 g, 0.5 mmol), rac-6-methoxy-4-oxiranyl-quinoline (prepared according to literature, 0.1 g, 1 eq), K$_2$CO$_3$ (0.097 g, 1.4 eq.) and LiClO$_4$ (0.055 g, 1.05 eq.) in DMF (4 mL) was stirred at 80° C. overnight. The mixture was partitioned between EA and water. The org. phase was washed with water (3 times) and brine, dried over MgSO$_4$ and concentrated. The residue was purified by chromatography over SiO$_2$ (DCM/MeOH 19:1 containing 1% NH$_4$OH) to give the title compound (0.14 g, 60% yield) as a yellowish foam.
$^1$H NMR (DMSO d6) δ: 9.67 (s, 1H); 8.72 (d, J=4.5 Hz, 1H); 7.94 (d, J=10 Hz, 1H); 7.58 (d, J=4.5 Hz, 1H); 7.50-7.25 (m, 2H); 7.24 (d, J=2.4 Hz, 1H); 6.97 (dd, J=2.4, 8.7 Hz, 1H); 6.75 (d, J=8.7 Hz, 1H); 5.46 (m, 2H); 4.20 (m, 4H); 3.93 (s, 3H); 3.20-3.00 (m, 2H); 2.70-2.50 (m, 2H); 2.30-2.00 (m, 3H); 1.80-1.60 (m, 4H).
MS (ESI, m/z): 464.1 [M+H$^+$].

Example 12

(2RS)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide 12.i. 4-(3-oxo-3,4-dihydro-2H-benzo[1,4]thiazin-6-ylcarbamoyl)-piperidine-1-carboxylic acid tert-butyl ester:
Starting from intermediate 11.i (0.23 g; 1 mmol) and intermediate 3.i (0.18 g, 1 eq.) and following the procedure of Example 1, step 1.iii, the title compound (0.4 g, 100% yield) was obtained as a colourless solid.
MS (ESI, m/z): 392.3 [M+H$^+$].

12.ii. Piperidine-4-carboxylic acid (3-oxo-3,4-dihydro-2H-benzo[1,4]thiazin-6-yl)-amide:
The title amine was isolated as a colourless solid (0.17 g, 58% yield), starting from intermediate 12.i (0.39 g, 1 mmol) and using the protocol of Example 11, step 11.iii.
MS (ESI, m/z): 292.2 [M+H$^+$].

12.iii. (2RS)-1-[2-hydroxy-2-(6-methoxy-quinolin-4-yl)-ethyl]-piperidine-4 carboxylic acid (3-oxo-3,4-dihydro-2H-benzo[1,4]thiazin-6-yl)-amide:
The title compound (0.14 g, 60% yield) was obtained as a yellowish foam, starting from amine 12.ii (0.17 g, 0.58 mmol) and using the protocol of Example 11, step 11.iv.
$^1$H NMR (DMSO d6) δ: 10.57 (s, 1H); 9.93 (s, 1H); 8.73 (d, J=4.5 Hz, 1H); 7.94 (d, J=10 Hz, 1H); 7.58 (d, J=4.5 Hz, 1H); 7.50-7.25 (m, 3H); 7.18 (m, 2H); 5.46 (m, 2H); 3.93 (s, 3H); 3.41 (s, 2H); 3.20-3.00 (m, 2H); 2.70-2.50 (m, 2H); 2.30-2.00 (m, 3H); 1.80-1.60 (m, 4H).
MS (ESI, m/z): 493.0 [M+H$^+$].

Example 13

1-[2-(6-methoxy-quinolin-4-yl)-ethyl]-piperidine-4-carboxylic acid [2-(2,5-difluoro-phenyl)-vinyl]-amide 13.i. 6-methoxy-4-vinyl-quinoline:
InCl$_3$ (1.1 g, 5 mmol) was dried under HV by heating with a heat gun. After cooling under N$_2$ atmosphere, THF (25 mL) was added and the mixture sonicated until a solution had formed. This solution was cooled to −78° C., and a 1.7M solution of vinyl magnesium chloride (15 mmol) was added dropwise. The mixture was stirred at −78° C. for 15 min, warmed to rt and the resulting solution was added to a refluxing mixture of 4-bromo-6-methoxy-quinoline (1.85 g, 10 mmol) and Pd(dppf)Cl$_2$.CH$_2$Cl$_2$ complex (0.408 g) in THF (25 mL). The mixture was refluxed for 2 h until tlc indicated complete conversion. The mixture was cooled to rt, quenched by addition of a few drops of MeOH and SiO$_2$ (20 g) was added. The volatiles were removed under reduced pressure and the residue was chromatographed over SiO$_2$ (Hex/EA 1:1) to give the desired compound (0.4 g, 21% yield) as a yellowish oil.

$^1$H NMR (CDCl$_3$) δ: 8.76 (d, J=4.5 Hz, 1H); 8.06 (d, J=9.2 Hz, 1H); 7.50-7.30 (m, 4H); 6.01 (dd, J=1.2, 17 Hz), 1H); 5.70 (dd, J=1.2, 11 Hz, 1H).

13.ii. 1-[2-(6-methoxy-quinolin-4-yl)-ethyl]-piperidine-4-carboxylic acid amide:

A solution of intermediate 13.i (0.15 g, 0.81 mmol) and piperidine-4-carboxylic acid amide (0.1 g, 1 eq.) in EtOH (5 mL) and AcOH (0.1 mL) was heated at reflux overnight. The residue was taken up in aq. ammonia and the product was extracted with DCM (3×20 mL). The organic phase was dried over MgSO$_4$ and concentrated. The product was obtained (0.12 g, 48% yield) after crystallisation with ether.

$^1$H NMR (DMSO d6) δ: 8.62 (d, J=4.5 Hz, 1H); 7.91 (d, J=10 Hz, 1H); 7.45-7.35 (m, 3H); 7.22 (br, 1H); 6.72 (br, 1H); 3.93 (s, 3H); 3.25-3.15 (m, 2H); 3.05-2.95 (m, 2H); 2.70-2.60 (m, 2H); 2.10-1.95 (m, 3H); 1.80-1.40 (m, 4H).

MS (ESI, m/z): 314.0 [M+H$^+$].

13.iii. 1-[2-(6-methoxy-quinolin-4-yl)-ethyl]-piperidine-4-carboxylic acid [2-(2,5-difluoro-phenyl)-vinyl]-amide:

A mixture of intermediate 13.ii (0.12 g, 0.41 mmol), 1,4-difluoro-2-(2-iodo-vinyl)-benzene (5 eq., prepared according to Takai, *J. Am. Chem. Soc.* (1986), 7408), N,N-dimethylglycine hydrochloride (0.0057 g, 0.1 eq), CuI (0.0078 g, 0.1 eq) and Cs$_2$CO$_3$ (0.366 g, 2 eq) in dioxane (2 mL) was degassed by bubbling N$_2$ through and then heated at 80° C. for 20 h. The mixture was partitioned between EA and water. The org. layer was washed with water and a sat. aq. NH$_4$Cl solution, dried over MgSO$_4$ and concentrated. The residue was purified by chromatography over SiO$_2$ (EA/MeOH 9:1) to give the title compound (0.018 g) as a tan solid.

$^1$H NMR (CDCl$_3$) δ: 8.60 (d, J=4.5 Hz, 1H); 7.94 (d, J=10 Hz, 1H); 7.65 (br d, 1H); 7.52 (dd, J=10.8, 14.5 Hz, 1H); 7.30 (dd, J=2.7, 9.2 Hz, 1H); 7.20 (d, J=3.3 Hz, 1H); 7.15 (d, J=4.4 Hz, 1H); 7.00 (m, 1H); 6.89 (m, 1H); 6.74 (m, 1H); 6.10 (d, J=14.5 Hz, 1H); 3.88 (s, 3H); 3.20-3.10 (m, 2H); 3.10-2.95 (m, 2H); 2.70-2.60 (m, 2H); 2.20-1.95 (m, 3H); 1.95-1.80 (m, 4H).

MS (ESI, m/z): 451.8 [M+H$^+$].

Example 14 trans-4-[(1R,2R)-1,2-dihydroxy-2-(3-methoxy-quinoxalin-5-yl)-ethyl]-cyclohexanecarboxylic acid (3-oxo-3,4-dihydro-2H-benzo[1,4]thiazin-6-yl)-amide 14.i. 5-[trans-4-(tert-butyl-dimethyl-silanyloxymethyl)-cyclohexylmethylsulfanyl]-1-phenyl-1H-tetrazole:

To a solution of [trans-4-(tert-butyl-dimethyl-silanyloxymethyl)-cyclohexyl]-methanol (prepared as described in *J. Med. Chem.* (2001), 44, 531, 9.0 g, 34.8 mmol) in THF (100 mL) were added PPh$_3$ (13.7 g, 1.5 eq.), 1-phenyl-1H-tetrazole-5-thiol (6.2 g, 1 eq.) and DIAD (10.3 mL, 1.5 eq.). The reaction mixture was stirred at rt overnight. After evaporation to dryness, the residue was chromatographed over SiO$_2$ (Hex-EA 8-1) to afford the title sulfide (11.4 g) contaminated with some PPh$_3$.

MS (ESI, m/z): 419.2 [M+H$^+$].

14.ii. 5-[4-(tert-butyl-dimethyl-silanyloxymethyl)-cyclohexylmethanesulfonyl]-1-phenyl-1H-tetrazole:

To a solution of intermediate 14.i (10.4 g) in EtOH (100 mL) was added a solution of ammonium molybdate heptahydrate (11 g) in 30% aq. hydrogen peroxide (40 mL). The mixture was stirred at rt for 4 h. Water (100 mL) was added and the solvent was removed in vacuo. The aq. layer was extracted twice with EA. The combined org. layers were washed with saturated Na$_2$SO$_3$ (2×150 mL), brine, dried over Na$_2$SO$_4$, filtered and concentrated to dryness. The residue was chromatographed over SiO$_2$ (Hex-EA 4-1) to afford the title sulfone as a colourless oil (10.2 g).

$^1$H NMR (CDCl$_3$) δ: 7.71-7.60 (m, 5H); 3.69 (d, J=6.3 Hz, 2H); 3.39 (d, J=6.0 Hz, 2H); 2.07-2.02 (m, 3H); 1.81 (m, 2H); 1.44 (m, 1H); 1.23 (m, 2H); 0.98 (m, 2H); 0.89 (s, 9H), 0.04 (s, 6H).

14.iii. (1R,2R)-1-[trans-4-(tert-butyl-dimethyl-silanyloxymethyl)-cyclohexyl]-2-(3-methoxy-quinoxalin-5-yl)-ethane-1,2-diol:

To a solution of intermediate 14.ii (4.0 g, 8.87 mmol) and 3-methoxy-quinoxaline-5-carbaldehyde (see preparation A; 2.0 g) in 1,2-DME (50 mL), cooled to −78° C., was added dropwise, a solution of KHMDS (0.5M in toluene, 30 mL). The mixture was stirred 30 min at the same temperature before warming to 0° C. The reaction proceeded for 1 h. Water (50 mL) and EA (100 mL) were added. The two layers were decanted and the aq. layer was extracted with EA (2×100 mL). The combined org. extracts were washed with brine, dried over Na$_2$SO$_4$, filtered and concentrated in vacuo. The residue was chromatographed over SiO$_2$ (Hept-EA 4-1) to afford the title alkene (2.9 g) as a colourless oil. The latter was taken up in 2-methyl-2-propanol (35 mL) and water (35 mL). Methanesulfonamide (0.7 g) and AD-mix β (10 g) were added. The reaction was stirred at rt for 48 h. Sodium bisulfite (11 g) was added. The two layers were decanted and the aq. layer was extracted with EA. The combined org. layers were washed with brine, dried over Na$_2$SO$_4$, filtered and concentrated to dryness. The residue was chromatographed over SiO$_2$ (EA-Hept 1-3 then 0-1) to afford the title diol (1.3 g, 2.91 mmol) as a white solid.

MS (ESI, m/z): 446.8 [M$^+$].

14.iv. {trans-4-[(4R,5R)-5-(3-methoxy-quinoxalin-5-yl)-2,2-dimethyl-[1,3]dioxolan-4-yl]-cyclohexyl}-methanol:

To a solution of intermediate 14.iii (1.3 g, 2.91 mmol) in THF (25 mL) were added PTSA (0.72 g) and 2,2-dimethoxypropane (1.8 mL). The reaction was stirred at rt for 3 h. Sat. aq. NaHCO$_3$ (50 mL) and EA (100 mL) were added. The two layers were decanted and the aq. layer was extracted once with EA (100 mL). The combined org. layers were concentrated to dryness and the residue was taken up in THF (10 mL) and TBAF (1M in THF; 5 mL) was added. The reaction proceeded overnight at rt. The solvent was removed in vacuo and the residue was chromatographed over SiO$_2$ (Hept-EA 1-1) to afford a solid that was further triturated in Hex to afford the title compound (0.73 g) as a white solid.

$^1$H NMR (CDCl$_3$) δ: 8.52 (s, 1H); 8.02 (dd, J=1.4, 8.2 Hz, 1H); 7.95 (d, J=1.4, 8.2 Hz, 1H); 7.65 (app t, J=8.2 Hz, 1H); 6.11 (d, J=8.7 Hz, 1H); 4.12 (s, 3H); 3.85 (dd, J=3.6, 8.7 Hz, 1H); 3.42 (d, J=6.2 Hz, 2H); 2.12 (m, 1H); 1.89 (m, 1H); 1.75-1.21 (m, 7H); 1.64 (s, 3H); 1.56 (s, 3H); 0.94-0.81 (m, 2H).

14.v. trans-4-[(4R,5R)-5-(3-methoxy-quinoxalin-5-yl)-2,2-dimethyl-[1,3]dioxolan-4-yl]-cyclohexanecarboxylic acid:

To a solution of oxalyl chloride (0.5 mL, 5.73 mmol) in DCM (6 mL), cooled to −78° C., was added dropwise a solution of DMSO (0.5 mL, 7.05 mmol) in DCM (6 mL). The mixture was stirred for 15 min and treated dropwise with a solution of intermediate 14.iv (0.73 g, 1.96 mmol) in DCM (6 mL). The mixture was further stirred 1 h at this temperature and a solution of TEA (2.2 mL, 15.7 mmol) in DCM (2.5 mL) added dropwise. The mixture was stirred 30 min before warming gradually to rt. The reaction was quenched by adding sat. aq. NaHCO$_3$. The two layers were decanted and the org. layer was dried over Na$_2$SO$_4$, filtered and concentrated to dryness. The residue was taken up in acetone (15 mL) and water (3 mL). Potassium permanganate (0.775 g) was added. The reaction proceeded for 1 h. Sodium bisulfite (1 g) was added. The mixture was stirred 15 min., diluted with acetone (20 mL) and water (20 mL). The mixture was filtered through Celite and the volatiles were removed in vacuo. The pH of the aq. layer was adjusted to 5 and extracted with EA (2×100 mL). The combined org. extracts were washed with brine, dried over Na$_2$SO$_4$, filtered and concentrated to dryness. The residue was triturated in Hex to afford the title acid (0.5 g, 66% yield) as a white solid.

$^1$H NMR (DMSO d6) δ: 11.9 (br s, 1H); 8.65 (s, 1H); 7.98 (d, J=7.7 Hz, 1H); 7.94 (d, J=7.7 Hz, 1H); 7.71 (t, J=7.7 Hz, 1H); 5.98 (d, J=8.6 Hz, 1H); 4.07 (s, 3H); 3.75 (br d, J=8.6 Hz, 1H); 2.05-1.99 (m, 2H); 1.89 (m, 1H); 1.74 (m, 1H); 1.64-1.36 (m, 2H); 1.56 (s, 3H); 1.45 (s, 3H); 1.24-0.93 (m, 4H).

14.vi. trans-4-[(4R,5R)-5-(3-methoxy-quinoxalin-5-yl)-2,2-dim ethyl-[1,3]dioxolan-4-yl]-cyclohexanecarboxylic acid (3-oxo-3,4-dihydro-2H-benzo[1,4]thiazin-6-yl)-amide:

To a suspension of intermediate 14.v (200 mg, 0.518 mmol) and 6-amino-4H-benzo[1,4]thiazin-3-one (93 mg, 0.518 mmol) in DMF (2 mL) and DCM (0.5 mL) was added DIPEA (0.266 mL, 1.553 mmol) and TPPA (50% in EA, 0.336 mL, 0.57 mmol). The resulting solution was stirred at rt overnight. The solvent was removed under reduced pressure and the residue chromatographed over SiO$_2$ (DCM/MeOH 19:1) to give the title compound (226 mg, 80% yield) as a colourless solid.

MS (ESI, m/z): 548.6 [M$^+$].

14.vii. trans-4-[(1R,2R)-1,2-dihydroxy-2-(3-methoxy-quinoxalin-5-yl)-ethyl]-cyclohexanecarboxylic acid (3-oxo-3,4-dihydro-2H-benzo[1,4]thiazin-6-yl)-amide:

Intermediate 14.vi was stirred in 1:1 TFA/H$_2$O (2 mL) 1 h at rt. The solvent was removed under reduced pressure and the residue taken up in water. The pH was adjusted to 8-9 and the precipitate filtered and dried to give the title compound (20 mg, 22% yield) as a colourless solid.

$^1$H NMR (DMSO d6) δ: 10.50 (s, 1H); 9.81 (s, 1H); 7.98 (d, J=7.7 Hz, 1H); 8.55 (s, 1H); 7.85-7.81 (m, 2H); 7.58 (t, J=10.8 Hz, 1H); 7.34 (br d, J=1.5 Hz, 1H); 7.15-7.07 (m, 2H); 5.66 (br d, J=1.5 Hz); 3.98 (s, 3H); 3.34 (s, 2H); 2.24-2.09 (m, 2H); 1.92-1.75 (m, 3H); 1.37-1.09 (m, 4H); 1.04-0.93 (m, 1H).

MS (ESI, m/z): 509.6 [M+H]$^+$.

Example 15 trans-4-[(1R,2R)-1,2-dihydroxy-2-(6-methoxy-[1,5]naphthyridin-4-yl)-ethyl]-cyclohexanecarboxylic acid (2,3-dihydro-benzo[1,4]dioxin-6-yl)-amide:

15.i. 8-{2-[trans-4-(tert-butyl-diethyl-silanyloxy ethyl)-cyclohexyl]-vinyl}-2-ethoxy-[1,5]naphthyridine:

To a solution of intermediate 14.ii (6.00 g, 13.31 mmol) and 6-methoxy-[1,5]naphthyridine-4-carbaldehyde (3.00 g, 15.98 mmol, preparation B) in 1,2-DME (75 mL) and toluene (20 mL) cooled to −78° C., was added dropwise, a solution of KHMDS (37.2 mL, 0.5M in toluene). The mixture was stirred 30 min at the same temperature before warming to 0° C. The reaction proceeded for 1 h. Water and EA were added. The two layers were separated and the aq. layer was extracted twice with EA. The combined org. extracts were washed with brine, dried over Na$_2$SO$_4$, filtered and concentrated. The residue was chromatographed over SiO$_2$ (Hex/EtOAc 3:1) to give the title compound (4.51 g, 82% yield) as a colourless oil.

$^1$H NMR (DMSO d6) δ: 8.65 (d, J=4.8 Hz, 1H); 8.19 (d, J=9.0 Hz, 1H); 7.74 (d, J=4.8 Hz, 1H); 7.36 (d, J=16.2 Hz, 1H); 7.22 (d, J=9.0 Hz, 1H); 6.84 (dd, J=16.2, 6.9 Hz, 1H); 4.01 (s, 3H); 3.39 (d, J=6.0 Hz, 2H); 2.22-215 (m, 1H); 1.88-1.74 (m, 3H); 1.5-0.88 (m, 6H); 0.83 (s, 9H); 0.00 (s, 6H).

MS (ESI, m/z): 413.1 [M$^+$].

15.ii. {trans-4-[(4R,5R)-5-(6-methoxy-[1,5]naphthyridin-4-yl)-2,2-dimethyl-[1,3]dioxolan-4-yl]-cyclohexyl}-methanol:

The title compound (2.98 g, 73% yield) was obtained as a colourless solid, starting from intermediate 15.i. and using the successive procedures of Example 14, steps 14.iii and 14.iv.

$^1$H NMR (DMSO d6) δ: 8.85 (d, J=4.6 Hz, 1H); 8.30 (d, J=9.1 Hz, 1H); 7.81 (d, J=4.6 Hz, 1H); 7.31 (d, J=9.1 Hz, 1H); 6.00 (d, J=8.6 Hz, 1H); 4.30 (t, J=5.3 Hz, 1H); 4.05 (s, 3H); 3.77 (dd, J=8.6, 3.5 Hz, 1H); 3.14 (t, J=5.8 Hz, 2H); 2.05-2.00 (m, 1H); 1.78-1.74 (m, 1H); 1.62-1.57 (m, 1H); 1.57 (s, 3H); 1.53-1.39 (m, 2H); 1.47 (s, 3H); 1.24-1.00 (m, 3H); 0.88-0.71 (m, 2H).

MS (ESI, m/z): 373.1 [M$^+$].

15.iii. trans-4-[(4R,5R)-5-(6-methoxy-[1,5]naphthyridin-4-yl)-2,2-dimethyl-[1,3]dioxolan-4-yl]-cyclohexanecarboxylic acid:

The title compound (2.86 g, 97% yield) was obtained as a colourless solid starting from intermediate 15.ii. and using the procedure of Example 14, step 14.v.

$^1$H NMR (DMSO d6) δ: 12.00 (br s, 1H); 8.84 (d, J=4.5 Hz, 1H); 8.30 (d, J=9.0 Hz, 1H); 7.81 (d, J=4.5 Hz, 1H); 7.32 (d, J=9.0 Hz, 1H); 5.99 (d, J=8.6 Hz, 1H); 4.05 (s, 3H); 3.76 (dd, J=8.6, 3.5 Hz, 1H); 2.10-1.91 (m, 3H); 1.78-1.75 (m, 1H); 1.57 (m, 3H); 1.51-1.09 (m, 6H); 1.47 (s, 3H).

MS (ESI, m/z): 387.0 [M$^+$].

15.iv. trans-4-[(4R,5R)-5-(6-methoxy-[1,5]naphthyridin-4-yl)-2,2-dimethyl-[1,3]dioxolan-4-yl]-cyclohexanecarboxylic acid (2,3-dihydro-benzo[1,4]dioxin-6-yl)-amide:

The title compound (0.55 g, 48% yield) was obtained as brownish oil starting from intermediate 15.iii. and using the procedure of Example 14, step 14.vi.

$^1$H NMR (DMSO d6) δ: 9.56 (s, 1H); 8.85 (d, J=4.6 Hz, 1H); 8.31 (d, J=9.0 Hz, 1H); 7.82 (d, J=4.6 Hz, 1H); 7.33 (d, J=9.0 Hz, 1H); 7.20 (d, J=2.4 Hz, 1H); 6.93 (dd, J=8.8, 2.4 Hz, 1H); 6.73 (d, J=8.8 Hz, 1H); 6.10 (d, J=8.6 Hz, 1H); 4.20-4.16 (m, 4H); 4.06 (s, 3H); 3.79 (dd, J=8.6, 3.5 Hz, 1H); 2.20-2.03 (m, 2H); 1.91-1.80 (m, 1H); 1.77-1.62 (m, 1H); 1.59 (s, 3H); 1.58-1.08 (m, 6H); 1.48 (s, 3H).

MS (ESI, m/z): 520.2 [M$^+$].

15.v. trans-4-[(1R,2R)-1,2-dihydroxy-2-(6-methoxy-[1,5]naphthyridin-4-yl)-ethyl]-cyclohexanecarboxylic acid (2,3-dihydro-benzo[1,4]dioxin-6-yl)-amide:

The title compound (0.31 g, 61% yield) was obtained as colourless solid starting from intermediate 15.iv and using the procedure described of Example 14, step 14.vii.

$^1$H NMR (DMSO d6) δ: 9.62 (s, 1H); 8.76 (d, J=4.5 Hz, 1H); 8.27 (d, J=9.0 Hz, 1H); 7.75 (d, J=4.5 Hz, 1H); 7.27-7.24 (m, 2H); 6.98 (dd, J=8.8, 2.4 Hz, 1H); 6.75 (d, J=8.8 Hz, 1H); 5.73 (dd, J=6.3, 1.4 Hz, 1H); 5.28 (d, J=6.3 Hz, 1H); 4.22-

4.18 (m, 4H); 4.01 (s, 3H); 3.51 (td, J=6.0, 2.1 Hz, 1H); 2.41-2.00 (m, 3H); 1.95-1.77 (m, 2H); 1.64-1.19 (m, 4H); 1.08-0.90 (m, 1H).

MS (ESI, m/z): 480.5 [M+H]$^+$.

Example 16 trans-4-[(1R,2R)-1,2-dihydroxy-2-(3-methoxy-quinoxalin-5-yl)-ethyl]-cyclohexanecarboxylic acid (2,3-dihydro-benzo[1,4]dioxin-6-yl)-amide 16.i. trans-4-[(4R,5R)-5-(3-methoxy-quinoxalin-5-yl)-2,2-dimethyl-[1,3]dioxolan-4-yl]-cyclohexanecarboxylic acid (2,3-dihydro-benzo[1,4]dioxin-6-yl)-amide:

The title compound (260 mg, 96% yield) was obtained as a colourless foam, starting from intermediate 14.v (200 mg, 0.518 mmol) and 2,3-dihydro-benzo[1,4]dioxin-6-ylamine (78 mg, 0.518 mmol) and using the procedure of Example 14, step 14.vi.

$^1$H NMR (DMSO d6) δ: 9.55 (s, 1H); 8.66 (s, 1H); 8.02-7.94 (m, 2H); 7.72 (t, J=7.7 Hz, 1H); 7.20 (d, J=2.4 Hz, 1H); 6.92 (dd, J=8.8, 2.4 Hz, 1H); 6.73 (d, J=8.8 Hz, 1H); 6.00 (d, J=8.7 Hz, 1H); 4.20-4.16 (m, 4H); 4.09 (s, 3H); 3.79 (dd, J=8.7, 3.5 Hz, 1H); 2.15-2.09 (m, 2H); 1.95-1.90 (m, 1H); 1.78-1.62 (m, 1H); 1.57 (s, 3H); 1.58-1.06 (m, 6H); 1.42 (s, 3H).

MS (ESI, m/z): 520.0 [M$^+$].

16.ii. trans-4-[1,2-dihydroxy-2-(3-methoxy-quinoxalin-5-yl)-ethyl]-cyclohexanecarboxylic acid (2,3-dihydro-benzo[1,4]dioxin-6-yl)-amide:

The title compound (90 mg, 37% yield) was obtained as a colourless solid, starting from intermediate 16.i and using the procedure of Example 14, step 14.vii.

$^1$H NMR (DMSO d6) δ: 9.60 (s, 1H); 8.62 (s, 1H); 7.91-7.87 (m, 2H); 7.64 (t, J=7.7 Hz, 1H); 7.23 (d, J=2.4 Hz, 1H); 6.96 (dd, J=8.8, 2.4 Hz, 1H); 6.74 (d, J=8.8 Hz, 1H); 5.76-5.71, m 1H); 5.16 (d, J=6.2 Hz, 1H); 4.21-4.17 (m, 4H); 4.04 (s, 3H); 3.45-3.38 (m, 1H); 2.30-2.12 (m, 2H); 1.99-1.76 (m, 3H); 1.54-0.96 (m, 5H).

MS (ESI, m/z): 480.5 [M+H]$^+$.

Example 17 trans-4-[(1R,2R)-1,2-dihydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide 17.i. trans-4-[(4R,5R)-5-(6-methoxy-[1,5]naphthyridin-4-yl)-2,2-dimethyl-[1,3]dioxolan-4-yl]-cyclohexanecarboxylic acid (3-oxo-3,4-dihydro-2H-benzo[1,4]thiazin-6-yl)-amide:

The title compound (160 mg, 56% yield) was obtained as a colourless foam, starting from intermediate 15.iii (200 mg, 0.518 mmol) and 6-amino-4H-benzo[1,4]thiazin-3-one (93 mg, 0.518 mmol) and using the procedure of Example 14, step 14.vi.

$^1$H NMR (DMSO d6) δ: 10.55 (s, 1H); 9.82 (s, 1H); 8.86 (d, J=4.6 Hz, 1H); 8.31 (d, J=9.1 Hz, 1H); 7.83 (d, J=4.6 Hz, 1H); 7.38-7.30 (m, 2H); 7.22-7.12 (m, 2H); 6.01 (d, J=8.6 Hz, 1H); 4.07 (s, 3H); 3.80 (dd, J=8.6, 3.3 Hz, 1H); 3.40 (s, 2H); 2.29-2.07 (m, 2H); 1.94-82 (m, 1H); 1.75-1.64 (m, 1H); 1.59 (s, 3H); 1.54-1.05 (m, 6H); 1.49 (s, 3H).

MS (ESI, m/z): 548.6 [M$^+$].

17.ii. trans-4-[(1R,2R)-1,2-dihydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide:

The title compound (80 mg, 31% yield) was obtained as a beige solid starting from intermediate 17.i and using the procedure of Example 14, step 14.vii.

$^1$H NMR (DMSO d6) δ: 10.56 (s, 1H); 9.89 (s, 1H); 8.76 (d, J=4.6 Hz, 1H); 8.27 (d, J=9.2 Hz, 1H); 7.76 (d, J=4.5 Hz, 1H); 7.42 (s, 1H); 7.26 (d, J=9.2 Hz, 1H); 7.24-7.16 (m, 2H); 5.73 (br. s, 1H); 5.32 (br. s, 1H); 4.23 (br. s, 1H); 4.01 (s, 3H); 3.52 (br. d, J=8.7 Hz, 1H); 3.41 (s, 2H); 2.37-2.00 (m, 3H); 1.96-1.81 (m, 2H); 1.68-0.94 (m, 5H).

MS (ESI, m/z): 509.6 [M+H]$^+$.

Example 18 trans-4-[(1S)-1-hydroxy-2-(6-methoxy-[1,5]naphthyridin-4-yl)-ethyl]-cyclohexanecarboxylic acid (2,3-dihydro-benzo[1,4]dioxin-6-yl)-amide 18.i. trans-4-[(4R,5R)-5-(6-methoxy-[1,5]naphthyridin-4-yl)-2-oxo-[1,3]dioxolan-4-yl]-cyclohexanecarboxylic acid (2,3-dihydro-benzo[1,4]dioxin-6-yl)-amide:

To an ice-chilled solution of intermediate 15.vii (300 mg, 0.623 mmol) in DCM (5 mL) were added pyridine (0.3 mL, 6 eq.) and triphosgene (93 mg, 0.313 mmol). The reaction mixture was stirred at this temperature for 10 min. The reaction was then quenched by adding an aq. sat. NaHCO$_3$ solution. The two layers were separated and the aq. layer was extracted with DCM. The combined org. layers were concentrated to dryness. The residue was chromatographed over SiO$_2$ (DCM-MeOH 40-1 to 20:1) to give the title compound (280 mg, 88% yield) as a colourless solid.

$^1$H NMR (CDCl$_3$) δ: 8.85 (d, J=4.5 Hz, 1H); 8.31 (d, J=9.1 Hz, 1H); 7.61 (d, J=4.5 Hz, 1H); 7.23 (d, J=9.1 Hz, 1H); 7.18 (d, J=2.4 Hz, 1H); 6.93 (dd, J=8.7, 2.4 Hz, 1H); 6.81 (d, J=8.7 Hz, 1H); 6.07 (d, J=5.1 Hz, 1H); 4.65 (t, J=5.1 Hz, 1H); 4.29-4.24 (m, 4H); 4.09 (m, 3H); 2.25-2.05 (m, 5H); 1.88-1.59 (m, 3H); 1.44-1.28 (m, 2H).

MS (ESI, m/z): 505.8 [M+H]$^+$.

18.ii. trans-4-[(1S)-1-hydroxy-2-(6-methoxy-[1,5]naphthyridin-4-yl)-ethyl]-cyclohexanecarboxylic acid (2,3-dihydro-benzo[1,4]dioxin-6-yl)-amide:

A solution of intermediate 18.i (120 mg, 0.237 mmol) in EA (10 mL) was hydrogenated over Pd(OH)$_2$ (80 mg) at 1 atm for 4 h. The catalyst was filtered off and the filtrate concentrated to dryness. The residue was purified by column chromatography over SiO$_2$ (DCM-MeOH 19-1) to afford the title compound (7 mg, 6% yield) as a colourless solid.

$^1$H NMR (CDCl$_3$) δ: 9.61 (s, 1H); 8.65 (d, J=4.6 Hz, 1H); 8.24 (d, J=9.0 Hz, 1H); 7.57 (d, J=9.6 Hz, 1H); 7.25-7.19 (m, 2H); 6.98 (dd, J=8.7, 2.4 Hz, 1H); 6.75 (d, J=8.47 Hz, 1H); 4.48 (d, J=5.2 Hz, 1H); 4.23-4.17 (m, 4H); 4.08 (s, 3H); 3.80-3.64 (m, 1H); 3.59 (dd, J=8.0, 2.6 Hz, 1H); 2.81 (dd, J=13.6, 9.0 Hz, 1H); 2.30-1.80 (m, 5H); 1.51-1.09 (m, 4H).

MS (ESI, m/z): 464.0 [M+H]$^+$.

Example 19 trans-4-hydroxy-4-[2-(6-methoxy-quinolin-4-yl)-ethyl]-cyclohexanecarboxylic acid (2,3-dihydro-benzo[1,4]dioxin-6-yl)-amide 19.i. trans-4-ethynyl-4-hydroxy-cyclohexanecarboxylic acid ethyl ester:

Starting from intermediate 7.ii (10.71 g, 39.90 mmol) and following the procedure of Example 7, step 7.iii, the title compound was obtained as a pale yellow solid (7.49 g, 96% yield) after chromatography over SiO₂ (Hex/EA 2:1).

¹H NMR (CDCl₃) δ: 4.13 (q, J=7.1 Hz, 2H); 2.27 (tt, J=3.7, 11.5 Hz, 1H); 2.34 (m, 1H); 2.09-1.53 (m, 9H); 1.24 (t, J=7.1 Hz, 3H).

19.ii. trans-4-hydroxy-4-(6-methoxy-quinolin-4-ylethynyl)-cyclohexanecarboxylic acid ethyl ester:

Starting from intermediate 19.i (1.57 g, 8.00 mmol) and 4-bromo-6-methoxy-quinoline (1.90 g, 1 eq) and following the procedure of Example 7, step 7.iv, the title compound was obtained as a pale yellow solid (2.06 g, 73% yield) after chromatography over SiO₂ (Hex/EA 1:1).

¹H NMR (DMSO d6) δ: 8.72 (d, J=4.5 Hz, 1H); 7.98 (dd, J=1.4, 8.2 Hz, 1H); 7.55 (d, J=4.5 Hz, 1H); 7.49-7.42 (m, 2H); 5.96 (s, 1H); 4.05 (q, J=7.1 Hz, 2H); 3.92 (s, 3H); 2.43-2.35 (m, 1H); 2.14-2.10 (m, 2H); 2.02-1.96 (m, 2H); 1.84-1.60 (m, 4H); 1.18 (t, J=7.1 Hz, 3H).

MS (ESI, m/z): 353.7 [M⁺].

19.iii. trans-4-hydroxy-4-[2-(6-ethoxy-quinolin-4-yl)-ethyl]-cyclohexanecarboxylic acid ethyl ester:

Starting from intermediate 19.ii (2.05 g, 5.80 mmol) and following the procedure of Example 7, step 7.v, the title compound was obtained as a yellow oil (1.72 g, 83% yield) after chromatography over SiO₂ (EA).

¹H NMR (CDCl₃) δ: 8.68 (d, J=4.5 Hz, 1H); 8.09 (d, J=9.1 Hz, 1H); 7.41 (dd, J=2.8, 9.1 Hz, 1H); 7.36 (d, J=2.8 Hz, 1H); 7.25 (d, J=4.5 Hz, 1H); 4.17 (q, J=7.1 Hz, 2H); 3.98 (s, 3H); 3.22-3.16 (m, 2H); 2.38-2.28 (m, 1H); 1.96-1.85 (m, 8H); 1.58-1.47 (m, 2H); 1.31 (t, J=7.1 Hz, 3H).

MS (ESI, m/z): 358.0 [M⁺].

19.iv. trans-4-hydroxy-4-[2-(6-ethoxy-quinolin-4-yl)-ethyl]-cyclohexanecarboxylic acid:

Starting from intermediate 19.iii (1.72 g, 4.81 mmol) and using the procedure of Example 7, step 7.vi, the title compound was obtained as a colourless solid (0.80 g, 50% yield).

¹H NMR (DMSO d6) δ: 12.07 (s, 1H); 8.61 (d, J=4.5 Hz, 1H); 7.92 (d, J=9.1 Hz, 1H); 7.43 (d, J=2.9 Hz, 1H); 7.39 (dd, J=2.9, 9.1 Hz, 1H); 7.33 (d, J=4.5 Hz, 1H); 4.51 (br. s, 1H); 3.92 (s, 3H); 3.08-3.03 (m, 2H); 2.35-2.28 (m, 1H); 1.87-1.42 (m, 10H).

MS (ESI, m/z): 330.1 [M+H⁺].

19.v. trans-4-hydroxy-4-[2-(6-methoxy-quinolin-4-yl)-ethyl]-cyclohexanecarboxylic acid (2,3-dihydro-benzo[1,4]dioxin-6-yl)-amide:

Starting from intermediate 19.iv (71 mg, 0.217 mmol) and 2,3-dihydro-benzo[1,4]dioxin-6-ylamine (51 mg, 1.55 eq) and following the procedure of Example 14, step 14.vi, the title compound was obtained as a pale beige solid (40 mg, 40% yield) after chromatography over SiO₂ (DCM/MeOH/aq. NH₄OH 1000:100:8).

¹H NMR (DMSO d6) δ: 9.69 (br. s, 1H); 8.62 (d, J=4.4 Hz, 1H); 7.92 (d, J=9.1 Hz, 1H); 7.42-7.38 (m, 2H); 7.32 (d, J=4.4 Hz, 1H); 7.27 (d, J=2.9 Hz, 1H); 7.00 (dd, J=2.9, 9.1 Hz, 1H); 6.75 (d, J=8.7 Hz, 1H); 4.34 (s, 1H), 4.25-4.18 (m, 4H); 3.94 (s, 3H); 3.16-3.07 (m, 2H); 2.33-2.21 (m, 1H); 1.92-1.55 (m, 8H); 1.43-1.30 (m, 2H).

MS (ESI, m/z): 463.0 [M+H⁺].

Example 20 trans-4-hydroxy-4-[2-(6-methoxy-quinolin-4-yl)-ethyl]-cyclohexanecarboxylic acid (3-oxo-3,4-dihydro-2H-benzo[1,4]thiazin-6-yl)-amide Starting from intermediate 19.iv (52 mg, 0.157 mmol) and 6-amino-4H-benzo[1,4]thiazin-3-one (34 mg, 1.20 eq) and following the procedure of Example 14, step 14.vi, the title compound was obtained as a pale beige solid (30 mg, 39% yield) after chromatography over SiO₂ (DCM/MeOH/aq. NH₄OH 1000:100:8).

¹H NMR (DMSO d6) δ: 10.58 (s, 1H); 9.98 (s, 1H); 8.61 (d, J=4.4 Hz, 1H); 7.94 (d, J=9.1 Hz, 1H); 7.45 (s, 1H); 7.42-7.38 (m, 2H); 7.34 (d, J=4.4 Hz, 1H); 7.23-1-7.17 (m, 2H); 4.35 (s, 1H); 3.94 (s, 3H); 3.40 (s, 2H); 3.16-3.06 (m, 2H); 2.39-2.26 (m, 1H); 1.94-1.57 (m, 8H); 1-44-1.30 (m, 2H).

MS (ESI, m/z): 491.9 [M+H]⁺.

Example 21 trans-4-hydroxy-4-[2-(6-methoxy-quinolin-4-yl)-ethyl]-cyclohexanecarboxylic acid (3-oxo-3,4-dihydro-2H-benzo[1,4]oxazin-6-yl)-amide To a solution of intermediate 19.iv (99 mg, 0.302 mmol) and 6-amino-4H-benzo[1,4]oxazin-3-one (97 mg, 2.1 eq) in DMF (5 mL) were added DIPEA (0.15 mL, 3 eq) and HATU (220 mg, 2 eq). The resulting solution was stirred at rt overnight. The mixture was poured into EA and brine and the phases were separated. The aq. layer was extracted three times with EA and the org. layer was washed several times with brine, dried over MgSO₄ and concentrated under reduced pressure. A mixture EA/Et₂O 1/1 was added. The resulting precipitate was filtered off, washed with EA and dried under HV to afford the title compound as a beige solid (45 mg, 32% yield).

¹H NMR (DMSO d6) δ: 10.72 (s, 1H); 9.77 (s, 1H); 8.61 (d, J=4.4 Hz, 1H); 7.93 (d, J=9.2 Hz, 1H); 7.42-7.38 (m, 3H); 7.33 (d, J=4.4 Hz, 1H); 7.07 (dd, J=2.5, 8.8 Hz, 1H); 6.86 (d, J=8.8 Hz, 1H); 4.51 (s, 2H); 4.37 (s, 1H); 3.94 (s, 3H); 3.14-3.09 (m, 2H); 2.31-2.23 (m, 1H); 1.95-1.25 (m, 10H).

MS (ESI, m/z): 475.8 [M+H]⁺.

Example 22 trans-4-hydroxy-4-[2-(3-methoxy-quinolin-5-yl)-ethyl]-cyclohexanecarboxylic acid (2,3-dihydro-benzo[1,4]dioxin-6-yl)-amide 22.i. trans-4-hydroxy-4-(3-methoxy-quinolin-5-ylethynyl)-cyclohexanecarboxylic acid ethyl ester:

Starting from intermediate 19.i (1.21 g, 6.15 mmol) and 5-bromo-3-methoxy-quinoline (see preparation C, 1.46 g, 1 eq) and using the procedure of Example 7, step 7.iv, the title compound was obtained as a pale yellow foam (1.82 g, 84% yield) after chromatography over SiO₂ (Hex/EA 1:1).

MS (ESI, m/z): 354.1 [M+H]⁺.

22.ii. trans-4-hydroxy-4-[2-(3-methoxy-quinolin-5-yl)-ethyl]-cyclohexanecarboxylic acid ethyl ester:

Starting from intermediate 22.i (1.825 g, 5.15 mmol) and using the procedure of Example 7, step 7.v, the title compound was obtained as a yellow foam (1.25 g, 68% yield) after chromatography over SiO₂ (EA).

MS (ESI, m/z): 358.0 [M+H]⁺.

22.iii. trans-4-hydroxy-4-[2-(3-methoxy-quinolin-5-yl)-ethyl]-cyclohexanecarboxylic acid:

Starting from intermediate 22.ii (1.25 g, 3.50 mmol) and using the procedure of Example 7, step 7.vi, the title compound was obtained as a beige solid (0.76 g, 66% yield).

$^1$H NMR (DMSO d6) δ: 11.97 (s, 1H); 8.65 (d, J=2.6 Hz, 1H); 7.80 (d, J=8.1 Hz, 1H); 7.74 (d, J=2.6 Hz, 1H); 7.48 (dd, J=7.0, 8.1 Hz, 1H); 7.40 (dd, J=1.1, 7.0 Hz, 1H); 4.28 (s, 1H); 3.98 (s, 3H); 3.11-3.05 (m, 2H); 2.21-2.14 (m, 1H); 1.83-1.65 (m, 8H); 1.43-1.34 (m, 2H).

MS (ESI, m/z): 330.0 [M+H$^+$].

22.iv. trans-4-hydroxy-4-[2-(3-methoxy-quinolin-5-yl)-ethyl]-cyclohexanecarboxylic acid (2,3-dihydro-benzo[1,4]dioxin-6-yl)-amide:

Starting from intermediate 22.iii (99 mg, 0.302 mmol) and 2,3-dihydro-benzo[1,4]dioxin-6-ylamine (99 mg, 2.14 eq) and following the procedure of Example 21, the title compound was obtained as a beige solid (139 mg, 100% yield).

$^1$H NMR (DMSO d6) δ: 9.72 (s, 1H); 8.65 (d, J=2.6 Hz, 1H); 7.80 (d, J=8.1 Hz, 1H); 7.76 (d, J=2.6 Hz, 1H); 7.49 (t, J=7.5 Hz, 1H); 7.41 (d, J=7.2 Hz, 1H); 7.27 (d, J=2.6 Hz, 1H); 7.01 (dd, J=2.6, 8.8 Hz, 1H); 6.75 (d, J=8.8 Hz, 1H); 4.33 (s, 1H), 4.22-4.18 (m, 4H); 3.98 (s, 3H); 3.13-3.08 (m, 2H); 2.26-2.20 (m, 1H); 1.91-1.57 (m, 8H); 1.41-1.33 (m, 2H).

MS (ESI, m/z): 462.9 [M+H$^+$].

Example 23 trans-4-hydroxy-4-[2-(3-methoxy-quinolin-5-yl)-ethyl]-cyclohexanecarboxylic acid (3-oxo-3,4-dihydro-2H-benzo[1,4]thiazin-6-yl)-amide Starting from intermediate 22.iii (62 mg, 0.187 mmol) and 6-amino-4H-benzo[1,4]thiazin-3-one (40 mg, 1.20 eq) and following the procedure of Example 14, step 14.vi, the title compound was obtained as a beige solid (40 mg, 44% yield) after chromatography over SiO$_2$ (DCM/MeOH/aq.NH$_4$OH 1000:100:8).

MS (ESI, m/z): 491.8 [M+H$^+$].

Example 24 trans-4-hydroxy-4-[2-(3-methoxy-quinolin-5-yl)-ethyl]-cyclohexanecarboxylic acid (3-oxo-3,4-dihydro-2H-benzo[1,4]oxazin-6-yl)-amide Starting from intermediate 22.iii (92 mg, 0.278 mmol) and 6-amino-4H-benzo[1,4]oxazin-3-one (97 mg, 2.1 eq) and following the procedure of Example 21, the title compound was obtained as a beige solid (102 mg, 77% yield).

MS (ESI, m/z): 476.0 [M+H$^+$].

Example 25 trans-4-hydroxy-4-[2-(6-methoxy-quinolin-4-yl)-ethyl]-cyclohexanecarboxylic acid [2-(2,5-difluoro-phenyl)-vinyl]-amide 25.i. trans-4-hydroxy-4-[2-(6-methoxy-quinolin-4-yl)-ethyl]-cyclohexanecarboxylic acid amide:

Intermediate 19.iv (0.2 g, 0.6 mmol) was suspended in DCE (4 mL) and DMF (1 mL). DIPEA (0.3 mL), ammonium chloride (0.039 g) and TPPA (catalytic amount) were added and the resulting solution stirred at rt for 5 h. The mixture was concentrated in vacuo and partitioned between EA and aq. sat. NaHCO$_3$ solution. The aq. layer was extracted twice with EA and the combined org. layers were dried over MgSO$_4$ and concentrated in vacuo. The residue was crystallised from ether/MeOH, filtered and dried to give the desired amide (0.085 g, 42% yield) as a colourless solid.

MS (ESI, m/z): 329.0 [M+H]$^+$.

25.ii. trans-4-hydroxy-4-[2-(6-methoxy-quinolin-4-yl)-ethyl]-cyclohexanecarboxylic acid [2-(2,5-difluoro-phenyl)-vinyl]-amide:

The title compound was prepared from intermediate 25.i (0.085 g, 0.26 mmol) using the procedure from Example 13, step 13.iii. and was isolated after chromatography over SiO$_2$ (EA/Hex 1:1, EA) and crystallisation from ether/MeOH as a colourless solid (0.036 g).

$^1$H NMR (DMSO d6) δ: 10.25 (d, J=10.5 Hz, 1H); 8.61 (d, J=4.4 Hz, 1H); 7.94 (d, J=7.3 Hz, 1H); 7.58 (dd, J=10.3, 14.7 Hz, 1H); 7.45-7.35 (m, 3H); 7.32 (d, J=4.4 Hz, 1H); 7.20 (m, 1H); 6.97 (m, 1H); 6.20 (d, J=14.7 Hz, 1H); 4.33 (s, 1H); 3.94 (s, 3H); 3.15-3.05 (m, 2H); 2.27 (m, 1H); 1.95-1.50 (m, 8H); 1.45-1.30 (m, 2H).

MS (ESI, m/z): 466.8 [M+H]$^+$.

Example 26 trans-4-hydroxy-4-[2-(3-methoxy-quinolin-5-yl)-ethyl]-cyclohexanecarboxylic acid [2-(2,5-difluoro-phenyl)-vinyl]-amide Starting from intermediate 22.iii (0.2 g) and following the procedure of Example 25, steps 25.i and 25.ii, the title compound (0.061 g) was isolated as a colourless solid.

$^1$H NMR (DMSO d6) δ: 10.25 (d, J=10.2 Hz, 1H); 8.66 (d, J=2.8 Hz, 1H); 7.80 (d, J=8.0 Hz, 1H); 7.75 (d, J=2.8 Hz, 1H); 7.65-7.35 (m, 4H); 7.20 (m, 1H); 6.97 (m, 1H); 6.20 (d, J=14.7 Hz, 1H); 4.32 (s, 1H); 3.98 (s, 3H); 3.15-3.05 (m, 2H); 2.27 (m, 1H); 1.95-1.50 (m, 8H); 1.45-1.30 (m, 2H).

MS (ESI, m/z): 466.8 [M+H]$^+$.

Example 27

1-[2-(6-methoxy-[1,5]naphthyridin-4-yl)-ethyl]-piperidine-4-carboxylic acid [2-(2,5-difluoro-phenyl)-vinyl]-amide 27.i. 2-ethoxy-8-vinyl-[1,5]naphthyridine:

A suspension of 8-bromo-2-methoxy-[1,5]naphthyridine (1.2 g, 5 mmol), tetrakis(triphenylphosphine)palladium (0.29 g), K$_2$CO$_3$ (0.691 g) and 2,4,6-trivinyl-cyclotriboroxane pyridine complex (1.2 g, prepared according to J. Org. Chem. (2002), 67, 4969) in DME (40 mL) and water (12 mL) was heated at 85° C. under N$_2$ overnight. The mixture was cooled to rt, diluted with water and extracted with ether. The combined org. extracts were dried over MgSO$_4$ and concentrated in vacuo. The product (1 g of red oil) was used as such without further purification.

$^1$H NMR (CDCl$_3$) δ: 8.75 (d, J=4.8 Hz, 1H); 8.28 (d, J=9.1 Hz, 1H); 7.86 (dd, J=11.1, 18.0 Hz, 1H); 7.72 (d, J=4.8 Hz, 1H); 7.18 (d, J=9.1 Hz, 1H); 6.28 (dd, J=11.1, 1.2 Hz, 1H); 4.13 (s, 3H).

27.ii. 1-[2-(6-methoxy-[1,5]naphthyridin-4-yl)-ethyl]-piperidine-4-carboxylic acid amide:

Starting from intermediate 27.i (0.5 g, 2.7 mmol) and following the procedure of Example 13, step 13.ii the amide (0.36 g, 43% yield) was isolated as a beige solid.

$^1$H NMR (DMSO d6) δ: 8.67 (d, J=4.4 Hz, 1H); 8.24 (d, J=9.0 Hz, 1H); 7.58 (d, J=4.4 Hz, 1H); 7.24 (d, J=9.0 Hz, 1H);

7.19 (br, 1H); 6.70 (br, 1H); 4.05 (s, 3H); 3.4-3.2 (m, 2H); 3.05-2.95 (m, 2H); 2.75-2.65 (m, 2H); 2.10-1.95 (m, 3H); 1.70-1.40 (m, 4H).

27.iii. 1-[2-(6-methoxy-[1,5]naphthyridin-4-yl)-ethyl]-piperidine-4-carboxylic acid [2-(2,5-difluoro-phenyl)-vinyl]-amide:

Starting from intermediate 27.ii (0.15 g, 0.48 mmol) and following the procedure of Example 13, step 13.iii the title compound was isolated as a colourless solid (0.07 g, 32% yield) after chromatography over SiO$_2$ (EA/MeOH 9:1, 4:1).

MS (ESI, m/z): 452.8 [M+H]$^+$.

Example 28 trans-4-[4-(2,3-dihydro-benzo[1,4]dioxin-6-ylcarbamoyl)-cyclohexylmethoxy]-quinoline-6-carboxylic acid methyl ester Starting from intermediate 1.iv (0.2 g, 0.68 mmol) and 4-hydroxy-quinoline-6-carboxylic acid methyl ester (0.139 g, 1 eq) the title compound (0.084 g, 25% yield) was obtained as a white solid using the procedure of Example 1, step 1.v. The compound was purified by chromatography over SiO$_2$ using a EA-MeOH mixture with a polarity gradient.

MS (ESI, m/z): 476.8 [M+H$^+$].

Example 29 trans-4-(6-cyano-quinolin-4-yloxymethyl)-cyclohexanecarboxylic acid (2,3-dihydro-benzo[1,4]dioxin-6-yl)-amide Starting from intermediate 1.iv (0.2 g, 0.68 mmol) and 4-hydroxy-quinoline-6-carbonitrile (0.116 g, 1 eq), the title compound (0.105 g, 34% yield) was obtained as a white solid using the procedure of Example 1, step 1.v. The compound was recrystallised from EA.

$^1$H NMR (DMSO d6) δ: 9.73 (s, 1H); 8.88 (d, J=5.3 Hz, 1H); 8.67 (m, 1H); 8.11-8.03 (m, 2H); 7.26 (d, J=2.4 Hz, 1H); 7.19 (d, J=5.4 Hz, 1H); 6.99 (dd, J=2.4, 8.7 Hz, 1H); 6.75 (d, J=8.7 Hz, 1H); 4.22-4.14 (m, 6H); 2.30 (m, 1H); 2.04-1.88 (m, 5H); 1.53 (m, 2H); 1.23 (m, 2H).

MS (ESI, m/z): 443.9 [M+H$^+$].

Example 30 trans-4-(2-cyano-quinolin-8-yloxymethyl)-cyclohexanecarboxylic acid (2,3-dihydro-benzo[1,4]dioxin-6-yl)-amide Starting from intermediate 1.iv (0.2 g, 0.68 mmol) and 8-hydroxy-quinoline-2-carbonitrile (0.116 g, 1 eq), the title compound (0.031 g, 10% yield) was obtained as a white solid using the procedure of Example 1, step 1.v. The compound was purified by chromatography using EA as an eluent.

$^1$H NMR (d6 DMSO) δ: 9.67 (s, 1H); 8.59 (d, J=8.6 Hz, 1H); 8.04 (d, J=8.6 Hz, 1H); 7.71 (app t, J=8.2 Hz, 1H); 7.62 (dd, J=1.2, 8.3 Hz, 1H); 7.36 (dd, J=1.2, 7.8 Hz, 1H); 7.26 (d, J=2.4 Hz, 1H); 6.98 (dd, J=2.4, 8.7 Hz, 1H); 6.75 (d, J=8.7 Hz, 1H); 4.22-4.17 (m, 4H); 4.06 (d, J=6.0 Hz, 2H); 2.29 (m, 1H); 2.04-1.88 (m, 5H); 1.52 (m 2H); 1.20 (m, 2H).

MS (ESI, m/z): 443.9 [M+H$^+$].

Example 31 trans-4-(quinolin-4-yloxymethyl)-cyclohexanecarboxylic acid (2,3-dihydro-benzo[1,4]dioxin-6-yl)-amide Starting from intermediate 1.iv (0.2 g, 0.68 mmol) and quinolin-4-ol (0.1 g, 1 eq), the title compound (0.090 g, 31% yield) was obtained as a white solid using the procedure of Example 1, step 1.v. The compound was purified by chromatography with EA as an eluent.

MS (ESI, m/z): 419.1 [M+H$^+$].

Example 32 trans-4-[(E)-2-(6-methoxy-[1,5]naphthyridin-4-yl)-vinyl]-cyclohexanecarboxylic acid (2,3-dihydro-benzo[1,4]dioxin-6-yl)-amide 32.i. {trans-4-[(E)-2-(6-ethoxy-[1,5]naphthyridin-4-yl)-vinyl]-cyclohexyl}-methanol:

To a solution of intermediate 15.ii (2.50 g, 6.06 mmol) in THF (30 mL) was added a 1M solution of TBAF (9.1 mL) in THF at rt. The resulting solution was stirred at rt for 6 h. Then water was added and the mixture was extracted with EA. The org. layer was washed with water and brine, dried over MgSO4, filtered and concentrated to afford the title intermediate as a pale yellow solid (1.81 g, 100% yield).

32.ii. trans-4-[(E)-2-(6-ethoxy-[1,5]naphthyridin-4-yl)-vinyl]-cyclohexanecarboxylic acid:

To a suspension of intermediate 32.i (1.41 g, 4.73 mmol) in 1:1 water/MeCN (12 mL) cooled to 0° C. was added diacetoxyiodobenzene (3.42 g, 2.2 eq) and TEMPO (148 mg, 0.2 eq). The mixture was stirred at 0° C. for 30 min and at rt for 6 h. The solvent was evaporated and the residue was suspended in DCM/MeOH and concentrated. This procedure was repeated one more time, then the residue was taken in DCM/ether and filtered to afford the title intermediate as a colourless powder (0.812 g, 55% yield).

MS (ESI, m/z): 313.1 [M+H$^+$].

32.iii. trans-4-[(E)-2-(6-methoxy-[1,5]naphthyridin-4-yl)-vinyl]-cyclohexanecarboxylic acid (2,3-dihydro-benzo[1,4]dioxin-6-yl)-amide:

Starting from intermediate 32.ii (400 mg, 1.28 mmol) and 2,3-dihydro-benzo[1,4]dioxin-6-ylamine (194 mg, 1.28 mmol) and following the procedure of Example 14, step 14.vi., the title compound was obtained as a colourless solid (0.27 g, 47% yield) after trituration in ether/MeOH.

MS (ESI, m/z): 445.8 [M$^+$].

Example 33 trans-4-[(E)-2-(6-methoxy-[1,5]naphthyridin-4-yl)-vinyl]-cyclohexanecarboxylic acid (3-oxo-3,4-dihydro-2H-benzo[1,4]thiazin-6-yl)-amide Starting from intermediate 26 ii. (250 mg, 0.80 mmol) and 6-amino-4H-benzo[1,4]thiazin-3-one (144 mg, 0.80 mmol) and following the procedure of Example 14, step 14.vi., the title compound was obtained as a colourless solid (0.19 g, 49% yield) after trituration in ether/MeOH.

MS (ESI, m/z): 474.7 [M$^+$].

Example 34 trans-4-[(rac)-2-hydroxy-2-(6-methoxy-[1,5]naph-thyridin-4-yl)-ethyl]-cyclohexanecarboxylic acid (2,3-dihydro-benzo[1,4]dioxin-6-yl)-amide 34.i. trans-4-(2-oxo-ethyl)-cyclohexanecarboxylic acid methyl ester:

To a suspension of (methoxy)triphenylphosphonium chloride (15.36 g, 43.5 mmol) in anhydrous THF (100 mL), cooled to 0° C., was added 2.5 N BuLi (17.4 mL). The resulting red solution was stirred at −5° C. for 45 min and a solution of trans-4-(2-oxo-ethyl)-cyclohexanecarboxylic acid methyl ester (3.70 g, 21.7 mmol, *J. Organomet. Chem.* (2004), 689(3), 639-646) in THF (35 mL) was added. The resulting orange mixture was further stirred at −5° C. for 3 h. MeOH (20 mL) was added. The solvent was removed in vacuo and the orange residue was purified over $SiO_2$ (Hex-EA 15/1) to afford a colorless oil (4.0 g, enol ether). The latter was taken up in DCM/H2O:5/1 (200 mL). Trichloroacetic acid was added and the mixture was further stirred for 3 h at rt. $NaHCO_3$ was added to adjust at pH 8 and the layers were separated. The org layer was dried over $MgSO_4$, filtered and concentrated to dryness. The yellow oil was chromatographed on $SiO_2$ (Hex/EE:9/1 to 2/1) to afford the title compound as a colorless oil (2.43 g, 61% yield).

34.ii. trans-4-[2-hydroxy-2-(6-methoxy-[1,5]naphthyridin-4-yl)-ethyl]-cyclohexanecarboxylic acid methyl ester:

To a solution of 8-bromo-2-methoxy-[1,5]naphthyridine (959 mg, 4.01 mmol, WO 2006/032466) in THF (20 mL), cooled to −78° C., was added BuLi 2.5M (1.7 mL, 1.05 eq). The resulting dark brown solution was stirred at −78° C. for 1 h, and then a solution of intermediate 34.i (739 mg, 4.01 mmol) in THF (10 mL) was added. The mixture was stirred at −78° C. for 1 h and then at −20° C. for 3 h. Aq. sat. $NH_4Cl$ and EA were added to the cooled solution (ice-acetone bath). The phases were separated and the aqueous phase was extracted 3 times with EA. The combined organic extracts were washed with $NH_4Cl$ and brine, dried over $MgSO_4$, filtered and concentrated under reduced pressure. The residue was chromatographed on $SiO_2$ (DCM/MeOH:40/1) to afford the title intermediate as a yellow foam (363 mg, 26% yield).

MS (ESI, m/z): 345.0 [M+H$^+$].

34.iii. trans-4-[2-hydroxy-2-(6-ethoxy-[1,5]naphthyridin-4-yl)-ethyl]-cyclohexanecarboxylic acid:

To a solution of intermediate 28 ii. (362 mg, 1.05 mmol) in MeOH/THF/water:2/2/1 (8 mL) was added LiOHxH$_2$O (53 mg, 1.2 eq) at rt. The resulting yellow solution was stirred at rt overnight and was concentrated under reduced pressure. The aqueous phase was washed with EA and the aq. layer was acidified with 1M HCl to adjust at pH 2. The resulting turbid mixture was extracted with 9:1 DCM/MeOH. The combined org. extracts were concentrated, triturated in ether and filtered to afford the title intermediate as a colourless solid (172 mg, 50% yield).

MS (ESI, m/z): 330.9 [M+H$^+$].

34.iv. trans-4-[(rac)-2-hydroxy-2-(6-ethoxy-[1,5]naphthyridin-4-yl)-ethyl]-cyclohexanecarboxylic acid (2,3-dihydro-benzo[1,4]dioxin-6-yl)-amide:

To a solution of intermediate 34.iii. (51 mg, 0.155 mmol) and 1,4-benzodioxan-6-amine (28 mg, 1.2 eq) in DMF (2 mL) were added DIPEA (0.077 mL, 3 eq), HOBt (21 mg, 1 eq) and EDCI (36 mg, 1.2 eq) at rt. After stirring for 5 h at rt the mixture was poured into EA and brine and the phases were separated. The aq. layer was 3 times extracted with EA and the org. layer was washed several times with a NaCl solution, dried over $MgSO_4$ and concentrated under reduced pressure. Purification by preparative HPLC (Waters, NarrowD) and lyophilisation afforded the title compound as a colourless solid (37 mg, 51% yield).

$^1$H NMR (DMSO d6) δ: 9.61 (s, 1H), 8.77 (d, J=4.5 Hz, 1H), 8.26 (d, J=9.0 Hz, 1H), 7.77 (d, J=4.5 Hz, 1H), 7.24 (m, 2H), 6.98 (dd, J=8.8, 1.8 Hz, 1H), 6.75 (d, J=8.5 Hz, 1H), 5.70 (d, J=9.0 Hz, 1H), 5.37 (br. s, 1H), 4.20 (d, J=4.8 Hz, 4H), 4.02 (s, 3H), 2.22 (m, 2H), 1.75 (m, 5H), 1.44 (m, 3H), 1.03 (m, 2H).

MS (ESI, m/z): 464.3 [M+H$^+$].

Example 35 trans-4-[(rac)-2-hydroxy-2-(6-methoxy-[1,5]naph-thyridin-4-yl)-ethyl]-cyclohexanecarboxylic acid (3-oxo-3,4-dihydro-2H-benzo[1,4]thiazin-6-yl)-amide To a solution of intermediate 34.iii (52 mg, 0.157 mmol) and 6-amino-4H-benzo [1,4]thiazin-3-one (48 mg, 1.7 eq) in DMF (2 mL) were added DIPEA (0.078 mL, 3 eq), HOBt (32 mg, 1.5 eq) and EDCI (54 mg, 1.8 eq) at rt. After stirring for 14 h at rt the mixture was poured into EA and brine and the phases were separated. The aq. layer was extracted 3 times with EA and the org. layer was washed several times with NaCl, dried over $MgSO_4$ and concentrated under reduced pressure. Purification by preparative HPLC (Waters, NarrowD) and lyophilisation afforded the title compound as a colourless solid (27 mg, 35% yield).

$^1$H NMR (DMSO d6) δ: 10.54 (s, 1H), 9.86 (s, 1H), 8.78 (d, J=4.3 Hz, 1H), 8.27 (d, J=9.0 Hz, 1H), 7.77 (d, J=4.5 Hz, 1H), 7.42 (d, J=1.5 Hz, 1H), 7.26 (d, J=9.0 Hz, 1H), 7.19 (m, 2H), 5.70 (m, 1H), 5.36 (d, J=4.8 Hz, 1H), 4.02 (s, 3H), 3.41 (s, 2H), 2.26 (m, 2H), 1.78 (m, 5H), 1.45 (m, 3H), 1.04 (m, 2H).

MS (ESI, m/z): 493.2 [M+H$^+$].

Example 36

1-[2-hydroxy-2-(6-methoxy-quinolin-4-yl)-ethyl]-piperidine-4-carboxylic acid benzothiazol-6-ylamide 36.i. 4-(benzothiazol-6-ylcarbamoyl)-piperidine-1-carboxylic acid tert-butyl ester:

A mixture of benzothiazol-6-ylamine (0.15 g, 1 mmol) and piperidine-1,4-dicarboxylic acid mono-tert-butyl ester (0.23 g, 1 mmol) in DMF (3 ml) was treated with DIPEA (5 eq.) and propylphosphonic anhydride (1 eq, 50% solution in EA). The mixture was stirred at rt for 72 h, diluted with water and extracted with EA. The org. layers were washed with water and brine, dried over $MgSO_4$ and concentrated. The residue was purified by chromatography on $SiO_2$ (hex/EA 1:1, EA) to give the coupling product as a colourless oil (0.22 g, 61% yield).

$^1$H NMR (DMSO d6) δ: 10.19 (s, 1H), 9.25 (s, 1H), 8.55 (d, J=1.9 Hz, 1H), 7.99 (d, J=8.9 Hz, 1H), 7.59 (dd, J=1.9, 8.9 Hz, 1H), 4.02 (m, 2H), 2.80 (m, 2H), 2.60 (m, 1H), 1.85 (m, 2H); 1.55 (m, 2H), 1.41 (s, 9H).

36.ii. Piperidine-4-carboxylic acid benzothiazol-6-ylamide:

A solution of intermediate 36.i (0.21 g, 0.6 mmol) in DCM (2 ml) was treated with TFA (1 ml). The mixture was stirred at rt for 4 h, concentrated in vacuo and partitioned between DCM and $NH_4OH$. The org. phase was dried over $MgSO_4$ and concentrated to give the title amine as a yellow solid (0.09 g, 57% yield)

MS (ESI, m/z): 262.2 [M+H$^+$]. .

36.iii. 1-[2-hydroxy-2-(6-methoxy-quinolin-4-yl)-ethyl]-piperidine-4-carboxylic acid benzothiazol-6-ylamide:

A mixture of rac-6-methoxy-4-oxiranyl-quinoline (0.069 g, 0.344 mmol), intermediate 36.ii (0.09 g, 0.344 mmol), $K_2CO_3$ (0.066 g, 0.48 mmol) and $LiClO_4$ (0.038 g, 0.362 mmol) in DMF (2 mL) was heated at 80° C. overnight. The mixture was partitioned between EA and water. The organic phase was washed with water and brine, dried over $MgSO_4$ and concentrated. The residue was purified by chromatography on $SiO_2$ (EA/MeOH 9:1+1% $NH_4OH$) to give the title compound as a yellowish foam (0.081 g, 51% yield).

$^1$H NMR (DMSO d6) δ: 10.19 (s, 1H), 9.25 (s, 1H), 8.73 (d, J=4.5 Hz, 1H), 8.57 (d, J=1.9 Hz, 1H), 8.00 (m, 2H), 7.60 (m, 2H); 7.37 (m, 2H), 5.45 (m, 2H), 3.93 (s, 3H), 3.15 (m, 2H), 2.60 (m, 1H), 2.36 (m, 1H), 2.15 (m, 2H), 1.85 (m, 4H).

MS (ESI, m/z): 463.2 [M+H$^+$].

Example 37

4-hydroxy-4-[2-(6-methoxy-[1,5]naphthyridin-4-yl)-ethyl]-cyclohexanecarboxylic acid (3-fluoro-4-methyl-phenyl)-amide A solution of intermediate 7.vi (0.1 g, 0.303 mmol) and 3-fluoro-4-methylaniline (0.04 g, 0.303 mmol) in DMF (1.5 mL) was treated with DIPEA (3 eq.) and propylphosphonic anhydride solution (50% in EA, 1.1 eq.). The mixture was stirred at rt for 1.5 h, partitioned between EA and water. The org. phase was washed several times with water and brine, dried over $MgSO_4$ and concentrated. Chromatography on $SiO_2$ (EA) gave the title compound as a colourless solid (0.035 g, 26% yield).

$^1$H NMR (DMSO d6) δ: 9.87 (m, 1H), 8.65 (m, 1H), 8.22 (m, 1H), 7.53 (m, 2H), 7.19 (m, 3H), 4.06 (m, 4H), 3.23 (m, 3H), 2.19 (m, 3H), 1.80 (m, 5H), 1.59 (m, 2H), 1.39 (m, 2H).

MS (ESI, m/z): 438.3 [M+H$^+$].

Example 38

4-hydroxy-4-[2-(6-methoxy-[1,5]naphthyridin-4-yl)-ethyl]-cyclohexanecarboxylic acid (4-ethyl-phenyl)-amide A solution of intermediate 7.vi. (0.1 g, 0.303 mmol) and 4-ethylaniline (0.037 g, 0.303 mmol) in DMF (1.5 mL) was treated with DIPEA (3 eq.) and propylphosphonic anhydride solution (50% in EA, 1.1 eq). The mixture was stirred at rt for 1.5 h and partitioned between EA and water. The org. phase was washed several times with water and brine, dried over $MgSO_4$ and concentrated. Chromatography on $SiO_2$ (EA) gave the title compound as a colourless solid (0.038 g, 29% yield).

$^1$H NMR (DMSO d6) δ: 9.66 (s, 1H), 8.65 (d, J=4.4 Hz, 1H), 8.22 (d, J=9.1 Hz, 1H), 7.50 (m, 3H), 7.15 (d, J=4.4 Hz, 1H), 7.09 (d, J=8.5 Hz, 2H), 4.11 (s, 1H), 4.03 (s, 3H), 3.19 (m, 2H), 2.25 (dd, J=2.1, 0.6 Hz, 2H), 1.81 (m, 6H), 1.58 (m, 2H), 1.40 (m, 2H), 1.13 (t, J=7.6 Hz, 3H).

MS (ESI, m/z): 434.4 [M+H$^+$].

Example 39

4-hydroxy-4-[2-(6-methoxy-[1,5]naphthyridin-4-yl)-ethyl]-cyclohexanecarboxylic acid (2,3-dihydro-benzo[1,4]dioxin-6-yl)-methyl-amide 39.i. (2,3-dihydro-benzo[1,4]dioxin-6-yl)-carbamic acid benzyl ester:

A mixture of 2,3-dihydro-benzo[1,4]dioxin-6-ylamine (1.51 g, 10 mmol) and $NaHCO_3$ (1.68 g, 20 mmol) in acetone/water (1:1, 40 mL) was cooled to 0° C. and benzyl chloroformate (1.05 eq) was added dropwise. The mixture was stirred at 0° C. for 1 h and at rt for 1 h. Acetone was evaporated in vacuo and the mixture partitioned between ether and water. The org. phase was washed with brine, dried over $MgSO_4$ and concentrated to give the benzyl-protected aniline as a colourless solid (2.8 g, 98% yield).

$^1$H NMR (DMSO d6) δ: 9.51 (s, 1H), 7.36 (m, 5H), 7.02 (d, J=2.1 Hz, 1H), 6.85 (dd, J=8.8, 2.3 Hz, 1H), 6.72 (m, 1H), 5.09 (s, 2H), 4.16 (m, 4H).

39.ii. (2,3-dihydro-benzo[1,4]dioxin-6-yl)-methyl-carbamic acid benzyl ester:

A suspension of NaH dispersion (0.32 g, 7.3 mmol) in dry THF (30 mL) was cooled to 0° C. Intermediate 39.i (2.0 g, 7 mmol) was added portionwise and the mixture was stirred at 0° C. for 15 min. A solution of methyl iodide (1.32 g, 9.3 mmol) in THF (5 mL) was then added dropwise so that the temperature did not exceed 10° C. The mixture was stirred at rt for 3 h, quenched by addition of a sat. solution of $NH_4Cl$ and extracted with ether. The org. phase was washed with brine, dried over $MgSO_4$ and concentrated. The residue was purified by chromatography on $SiO_2$ (Hex/EA 4:1 to give the desired intermediate as a yellowish oil (1.8 g, 85% yield).

$^1$H NMR (CDCl$_3$) δ: 7.29 (m, 5H), 6.82 (m, 1H), 6.76 (s, 2H), 5.15 (s, 2H), 4.25 (s, 4H), 3.25 (s, 3H).

39.iii. (2,3-dihydro-benzo[1,4]dioxin-6-yl)-methyl-amine:

A solution of intermediate 39.ii (1.8 g, 6 mmol) in MeOH (60 ml) was hydrogenated over Pd/C (10%, 0.1 eq) and 1 bar of $H_2$. After completion of reaction (judged by tlc), the catalyst was filtered off and the filtrate concentrated to give the desired aniline as a brownish oil (0.97 g, 97% yield).

$^1$H NMR (CDCl$_3$) δ: 6.71 (dd, J=7.6, 0.9 Hz, 1H), 6.16 (m, 2H), 4.21 (m, 5H), 2.77 (s, 4H).

MS (ESI, m/z): 166.2 [M+H$^+$].

39.iv. 4-hydroxy-4-[2-(6-ethoxy-[1,5]naphthyridin-4-yl)-ethyl]-cyclohexanecarboxylic acid (2,3-dihydro-benzo[1,4]dioxin-6-yl)-methyl-amide:

A solution of intermediate 7.vi (0.1 g, 0.303 mmol) and intermediate 39.iii. (0.05 g, 0.303 mmol) in DMF (1.5 mL) was treated with DIPEA (3 eq.) and a propylphosphonic anhydride solution (50% in EA, 1.1 eq.). The mixture was stirred at rt for 1.5 h, partitioned between EA and water. The org. phase was washed several times with water and brine, dried over $MgSO_4$ and concentrated. Chromatography on $SiO_2$ (EA) gave the title compound as a colourless solid (0.024 g, 29% yield).

$^1$H NMR (DMSO d6) δ: 8.61 (d, J=4.4 Hz, 1H), 8.19 (d, J=9.1 Hz, 1H), 7.45 (d, J=4.4 Hz, 1H), 7.20 (d, J=9.1 Hz, 1H), 6.80 (m, 3H), 4.24 (s, 4H), 4.02 (s, 1H), 3.96 (s, 3H), 3.09 (m, 5H), 2.11 (m, 1H), 1.82 (m, 2H), 1.61 (m, 4H), 1.36 (m, 2H), 1.06 (m, 2H).

MS (ESI, m/z): 478.0 [M+H$^+$].

Pharmacological Properties of the Invention Compounds

In Vitro Assays

Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards Villanova, Pa., USA, 1997". Minimal inhibitory concentrations (MICs; mg/L) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against several Gram positive and Gram negative bacteria.

Typical antibacterial test results are given in the table hereafter (MIC in mg/L).

| Example No. | S. aureus A798 | S. Pneumoniae 49619 | M. catarrhalis A894 |
|---|---|---|---|
| 1 | 0.06 | 0.06 | 0.5 |
| 12 | 1 | 2 | 0.25 |
| 26 | <0.03 | 0.125 | <0.03 |
| 39 | 1 | 8 | 8 |

The invention claimed is:

1. A compound of formula I

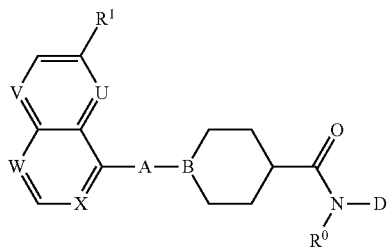

wherein

R$^0$ represents hydrogen or methyl;

R$^1$ represents hydrogen, halogen, (C$_1$-C$_4$)alkyl, (C$_1$-C$_4$)alkoxy, cyano or COOR$^2$, R$^2$ being (C1-C4)alkyl;

one or two of U, V, W and X represent(s) N and each of the remaining represent CH, or, in the case of X, may also represent CR$^x$, R$^x$ being a halogen atom;

either B represents N and A represents CH$_2$CH$_2$ or CH(OR$^3$)CH$_2$, or B represents CH or C(OR$^4$) and A represents OCH$_2$, CH$_2$CH(OR$^5$), CH(OR$^6$)CH$_2$, CH(OR$^7$)CH(OR$^8$), CH=CH or CH$_2$CH$_2$;

each of R$^3$, R$^4$, R$^5$, R$^6$, R$^7$ and R$^8$ represents independently hydrogen, SO$_3$H, PO$_3$H$_2$, CH$_2$OPO$_3$H$_2$ or COR$^9$, R$^9$ being either CH$_2$CH$_2$COOH or such that R$^9$—COOH is a naturally occurring amino acid or dimethylaminoglycine;

D represents styryl, heteroarylvinyl, binuclear heteroaryl or a phenyl group which is substituted independently once or twice in the meta and/or para position(s) by a halogen, an alkyl group of one to three carbon atoms, an alkoxy group of one to three carbon atoms, a trifluoromethyl group or a trifluoromethoxy group;

or a salt thereof.

2. A compound of formula I$_P$

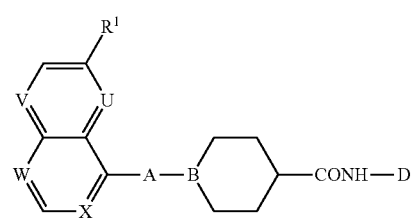

wherein

R$^1$ represents hydrogen, halogen, (C$_1$-C$_4$)alkyl, (C$_1$-C$_4$)alkoxy, cyano or COOR$^2$, R$^2$ being (C$_1$-C$_4$)alkyl;

one or two of U, V, W and X represent(s) N and each of the remaining represent CH, or, in the case of X, may also represent CR$^x$, R$^x$ being a halogen atom;

either B represents N and A represents CH$_2$CH$_2$ or CH(OR$^3$)CH$_2$, or B represents CH or C(OR$^4$) and A represents OCH$_2$, CH$_2$CH(OR$^5$), CH(OR$^6$)CH$_2$, CH(OR$^7$)CH(OR$^8$), CH=CH or CH$_2$CH$_2$;

each of R$^3$, R$^4$, R$^5$, R$^6$, R$^7$ and R$^8$ represents independently hydrogen, SO$_3$H, PO$_3$H$_2$, CH$_2$OPO$_3$H$_2$ or COR$^9$, R$^9$ being either CH$_2$CH$_2$COOH or such that R$^9$—COOH is a naturally occurring amino acid or dimethylaminoglycine;

D represents styryl, heteroarylvinyl or binuclear heteroaryl;

or a salt thereof.

3. A compound of formula I as defined in claim 1, wherein R$^0$, R$^1$, U, V, W, X and D are as defined in formula I of claim 1; and either B represents N and A represents CH$_2$CH$_2$ or CH(OH)CH$_2$, or B represents CH or C(OH) and A represents OCH$_2$, CH$_2$CH(OH), CH(OH)CH$_2$, CH(OH)CH(OH), CH=CH or CH$_2$CH$_2$;

or a salt of said compound.

4. A compound of formula I according to claim 1, wherein R$^1$ is hydrogen, fluorine, (C$_1$-C$_3$)alkoxy, cyano or COOR$^2$, R$^2$ being methyl or ethyl;

or a salt of said compound.

5. A compound of formula I according to claim 1, wherein W is N and U, V and X are each CH, or U and W are each N and V and X are each CH, or W and X are each N and U and V are each CH, or V is N and U, W and X are each CH, or U and V are each N and W and X are each CH, or U is N and V, W and X are CH;

or a salt of said compound.

6. A compound of formula I according to claim 1, wherein D represents a styryl group including a phenyl group that is substituted one or two times by fluorine atoms, or D represents a binuclear heteroaryl group of formula

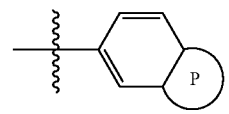

wherein
P is one of:

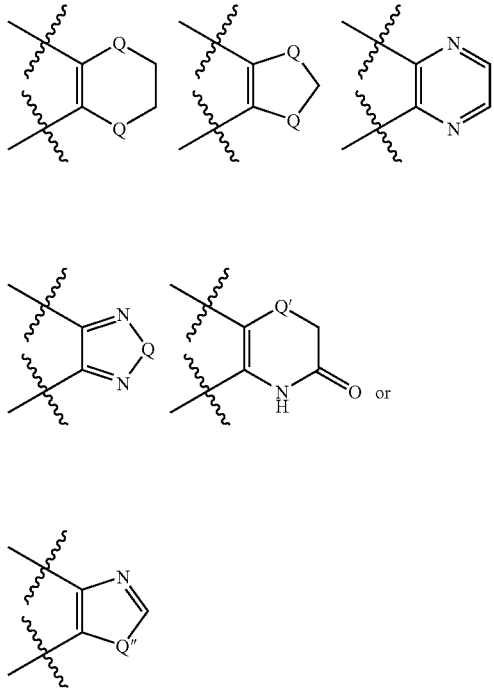

wherein
Q is O or S,
Q' is O or S, and
Q" is O or S, or also
D represents a phenyl group which is substituted independently once or twice in the meta and/or para position(s) by a halogen, an alkyl group of one to three carbon atoms, an alkoxy group of one to three carbon atoms, a trifluoromethyl group or a trifluoromethoxy group;
or a salt of said compound.

7. A compound of formula I according to claim 1, wherein $R^0$ represents hydrogen;
or a salt of said compound.

8. A compound of formula I according to claim 1, wherein $R^0$ represents methyl;
or a salt of said compound.

9. A compound of formula I according to claim 1, wherein the compound is:
trans-4-(6-methoxy-quinolin-4-yloxymethyl)-cyclohexanecarboxylic acid (2,3-dihydro-benzo[1,4]dioxin-6-yl)-amide;
trans-4-(6-methoxy-quinazolin-4-yloxymethyl)-cyclohexanecarboxylic acid (2,3-dihydro-benzo[1,4]dioxin-6-yl)-amide;
trans-4-(6-methoxy-quinolin-4-yloxymethyl)-cyclohexanecarboxylic acid (3-oxo-3,4-dihydro-2H-benzo[1,4]thiazin-6-yl)-amide;
trans-4-(6-methoxy-quinazolin-4-yloxymethyl)-cyclohexanecarboxylic acid (3-oxo-3,4-dihydro-2H-benzo[1,4]thiazin-6-yl)-amide;
trans-4-[2-(6-methoxy-[1,5]naphthyridin-4-yl)-ethyl]-cyclohexanecarboxylic acid (2,3-dihydro-benzo[1,4]dioxin-6-yl)-amide;
trans-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
cis-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;
cis-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
trans-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;
trans-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
(2R)-1-[2-hydroxy-2-(6-methoxy-quinolin-4-yl)-ethyl]-piperidine-4-carboxylic acid (2,3-dihydro-benzo[1,4]dioxin-6-yl)-amide;
(2S)-1-[2-hydroxy-2-(6-methoxy-quinolin-4-yl)-ethyl]-piperidine-4-carboxylic acid (2,3-dihydro-benzo[1,4]dioxin-6-yl)-amide;
(2R)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;
(2S)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;
1-[2-(6-methoxy-quinolin-4-yl)-ethyl]-piperidine-4-carboxylic acid [2-(2,5-difluoro-phenyl)-vinyl]-amide;
trans-4-[(1R,2R)-1,2-dihydroxy-2-(3-methoxy-quinoxalin-5-yl)-ethyl]-cyclohexanecarboxylic acid (3-oxo-3,4-dihydro-2H-benzo[1,4]thiazin-6-yl)-amide;
trans-4-[(1R,2R)-1,2-dihydroxy-2-(6-methoxy-[1,5]naphthyridin-4-yl)-ethyl]-cyclohexanecarboxylic acid (2,3-dihydro-benzo[1,4]dioxin-6-yl)-amide;
trans-4-[(1R,2R)-1,2-dihydroxy-2-(3-methoxy-quinoxalin-5-yl)-ethyl]-cyclohexanecarboxylic acid (2,3-dihydro-benzo[1,4]dioxin-6-yl)-amide;
trans-4-[(1R,2R)-1,2-dihydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide;
trans-4-[(1S)-1-hydroxy-2-(6-methoxy-[1,5]naphthyridin-4-yl)-ethyl]-cyclohexanecarboxylic acid (2,3-dihydro-benzo[1,4]dioxin-6-yl)-amide;
trans-4-hydroxy-4-[2-(6-methoxy-quinolin-4-yl)-ethyl]-cyclohexanecarboxylic acid (2,3-dihydro-benzo[1,4]dioxin-6-yl)-amide;
trans-4-hydroxy-4-[2-(6-methoxy-quinolin-4-yl)-ethyl]-cyclohexanecarboxylic acid (3-oxo-3,4-dihydro-2H-benzo[1,4]thiazin-6-yl)-amide;
trans-4-hydroxy-4-[2-(6-methoxy-quinolin-4-yl)-ethyl]-cyclohexanecarboxylic acid (3-oxo-3,4-dihydro-2H-benzo[1,4]oxazin-6-yl)-amide;
trans-4-hydroxy-4-[2-(3-methoxy-quinolin-5-yl)-ethyl]-cyclohexanecarboxylic acid (2,3-dihydro-benzo[1,4]dioxin-6-yl)-amide;
trans-4-hydroxy-4-[2-(3-methoxy-quinolin-5-yl)-ethyl]-cyclohexanecarboxylic acid (3-oxo-3,4-dihydro-2H-benzo[1,4]thiazin-6-yl)-amide;
trans-4-hydroxy-4-[2-(3-methoxy-quinolin-5-yl)-ethyl]-cyclohexanecarboxylic acid (3-oxo-3,4-dihydro-2H-benzo[1,4]oxazin-6-yl)-amide;

trans-4-hydroxy-4-[2-(6-methoxy-quinolin-4-yl)-ethyl]-cyclohexanecarboxylic acid [2-(2,5-difluoro-phenyl)-vinyl]-amide;

trans-4-hydroxy-4-[2-(3-methoxy-quinolin-5-yl)-ethyl]-cyclohexanecarboxylic acid [2-(2,5-difluoro-phenyl)-vinyl]-amide;

1-[2-(6-methoxy-[1,5]naphthyridin-4-yl)-ethyl]-piperidine-4-carboxylic acid [2-(2,5-difluoro-phenyl)-vinyl]-amide;

trans-4-[4-(2,3-dihydro-benzo[1,4]dioxin-6-ylcarbamoyl)-cyclohexylmethoxy]-quinoline-6-carboxylic acid methyl ester;

trans-4-(6-cyano-quinolin-4-yloxymethyl)-cyclohexanecarboxylic acid (2,3-dihydro-benzo[1,4]dioxin-6-yl)-amide;

trans-4-(2-cyano-quinolin-8-yloxymethyl)-cyclohexanecarboxylic acid (2,3-dihydro-benzo[1,4]dioxin-6-yl)-amide;

trans-4-(quinolin-4-yloxymethyl)-cyclohexanecarboxylic acid (2,3-dihydro-benzo[1,4]dioxin-6-yl)-amide;

trans-4-[(E)-2-(6-methoxy-[1,5]naphthyridin-4-yl)-vinyl]-cyclohexanecarboxylic acid (2,3-dihydro-benzo[1,4]dioxin-6-yl)-amide;

trans-4-[(E)-2-(6-methoxy-[1,5]naphthyridin-4-yl)-vinyl]-cyclohexanecarboxylic acid (3-oxo-3,4-dihydro-2H-benzo[1,4]thiazin-6-yl)-amide;

trans-4-[2-hydroxy-2-(6-methoxy-[1,5]naphthyridin-4-yl)-ethyl]-cyclohexanecarboxylic acid (2,3-dihydro-benzo[1,4]dioxin-6-yl)-amide;

trans-4-[2-hydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

1-[2-hydroxy-2-(6-methoxy-quinolin-4-yl)-ethyl]-piperidine-4-carboxylic acid benzothiazol-6-ylamide;

4-hydroxy-4-[2-(6-methoxy-[1,5]naphthyridin-4-yl)-ethyl]-cyclohexanecarboxylic acid (3-fluoro-4-methyl-phenyl)-amide;

4-hydroxy-4-[2-(6-methoxy-[1,5]naphthyridin-4-yl)-ethyl]-cyclohexanecarboxylic acid (4-ethyl-phenyl)-amide; or 4-hydroxy-4-[2-(6-methoxy-[1,5]naphthyridin-4-yl)-ethyl]-cyclohexanecarboxylic acid (2,3-dihydro-benzo[1,4]dioxin-6-yl)-methyl-amide;

or a salt of said compound.

10. A compound of formula I$_P$ according to claim 2, wherein the compound is:

trans-4-(6-methoxy-quinolin-4-yloxymethyl)-cyclohexanecarboxylic acid (2,3-dihydro-benzo[1,4]dioxin-6-yl)-amide;

trans-4-(6-methoxy-quinazolin-4-yloxymethyl)-cyclohexanecarboxylic acid (2,3-dihydro-benzo[1,4]dioxin-6-yl)-amide;

trans-4-(6-methoxy-quinolin-4-yloxymethyl)-cyclohexanecarboxylic acid (3-oxo-3,4-dihydro-2H-benzo[1,4]thiazin-6-yl)-amide;

trans-4-(6-methoxy-quinazolin-4-yloxymethyl)-cyclohexanecarboxylic acid (3-oxo-3,4-dihydro-2H-benzo[1,4]thiazin-6-yl)-amide;

trans-4-[2-(6-methoxy-[1,5]naphthyridin-4-yl)-ethyl]-cyclohexanecarboxylic acid (2,3-dihydro-benzo[1,4]dioxin-6-yl)-amide;

trans-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

cis-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;

cis-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

trans-4-hydroxy-4-[2-(6-methoxy-[1,5]naphthyridin-4-yl)-ethyl]-cyclohexanecarboxylic acid (2,3-dihydro-benzo[1,4]dioxin-6-yl)-amide;

trans-4-hydroxy-4-[2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

(2R)-1-[2-hydroxy-2-(6-methoxy-quinolin-4-yl)-ethyl]-piperidine-4-carboxylic acid (2,3-dihydro-benzo[1,4]dioxin-6-yl)-amide;

(2S)-1-[2-hydroxy-2-(6-methoxy-quinolin-4-yl)-ethyl]-piperidine-4-carboxylic acid (2,3-dihydro-benzo[1,4]dioxin-6-yl)-amide;

(2R)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;

(2S)-1-[2-hydroxy-2-(6-methoxy-quinolin-4-yl)-ethyl]-piperidine-4-carboxylic acid (3-oxo-3,4-dihydro-2H-benzo[1,4]thiazin-6-yl)-amide;

1-[2-(6-methoxy-quinolin-4-yl)-ethyl]-piperidine-4-carboxylic acid [2-(2,5-difluoro-phenyl)-vinyl]-amide;

trans-4-[(1R,2R)-1,2-dihydroxy-2-(3-methoxy-quinoxalin-5-yl)-ethyl]-cyclohexanecarboxylic acid (3-oxo-3,4-dihydro-2H-benzo[1,4]thiazin-6-yl)-amide;

trans-4-[(1R,2R)-1,2-dihydroxy-2-(6-methoxy-[1,5]naphthyridin-4-yl)-ethyl]-cyclohexanecarboxylic acid (2,3-dihydro-benzo[1,4]dioxin-6-yl)-amide;

trans-4-[(1R,2R)-1,2-dihydroxy-2-(3-methoxy-quinoxalin-5-yl)-ethyl]-cyclohexanecarboxylic acid (2,3-dihydro-benzo[1,4]dioxin-6-yl)-amide;

trans-4-[(1R,2R)-1,2-dihydroxy-2-(6-methoxy-[1,5]naphthyridin-4-yl)-ethyl]-cyclohexanecarboxylic acid (3-oxo-3,4-dihydro-2H-benzo[1,4]thiazin-6-yl)-amide;

trans-4-[(1S)-1-hydroxy-2-(6-methoxy-[1,5]naphthyridin-4-yl)-ethyl]-cyclohexanecarboxylic acid (2,3-dihydro-benzo[1,4]dioxin-6-yl)-amide;

trans-4-hydroxy-4-[2-(6-methoxy-quinolin-4-yl)-ethyl]-cyclohexanecarboxylic acid (2,3-dihydro-benzo[1,4]dioxin-6-yl)-amide;

trans-4-hydroxy-4-[2-(6-methoxy-quinolin-4-yl)-ethyl]-cyclohexanecarboxylic acid (3-oxo-3,4-dihydro-2H-benzo[1,4]thiazin-6-yl)-amide;

trans-4-hydroxy-4-[2-(6-methoxy-quinolin-4-yl)-ethyl]-cyclohexanecarboxylic acid (3-oxo-3,4-dihydro-2H-benzo[1,4]oxazin-6-yl)-amide;

trans-4-hydroxy-4-[2-(3-methoxy-quinolin-5-yl)-ethyl]-cyclohexanecarboxylic acid (2,3-dihydro-benzo[1,4]dioxin-6-yl)-amide;

trans-4-hydroxy-4-[2-(3-methoxy-quinolin-5-yl)-ethyl]-cyclohexanecarboxylic acid (3-oxo-3,4-dihydro-2H-benzo[1,4]thiazin-6-yl)-amide;

trans-4-hydroxy-4-[2-(3-methoxy-quinolin-5-yl)-ethyl]-cyclohexanecarboxylic acid (3-oxo-3,4-dihydro-2H-benzo[1,4]oxazin-6-yl)-amide;

trans-4-hydroxy-4-[2-(6-methoxy-quinolin-4-yl)-ethyl]-cyclohexanecarboxylic acid [2-(2,5-difluoro-phenyl)-vinyl]-amide;

trans-4-hydroxy-4-[2-(3-methoxy-quinolin-5-yl)-ethyl]-cyclohexanecarboxylic acid [2-(2,5-difluoro-phenyl)-vinyl]-amide;

1-[2-(6-methoxy-[1,5]naphthyridin-4-yl)-ethyl]-piperidine-4-carboxylic acid [2-(2,5-difluoro-phenyl)-vinyl]-amide;

trans-4-[4-(2,3-dihydro-benzo[1,4]dioxin-6-ylcarbamoyl)-cyclohexylmethoxy]-quinoline-6-carboxylic acid methyl ester;

trans-4-(6-cyano-quinolin-4-yloxymethyl)-cyclohexanecarboxylic acid (2,3-dihydro-benzo[1,4]dioxin-6-yl)-amide;

trans-4-(2-cyano-quinolin-8-yloxymethyl)-cyclohexanecarboxylic acid (2,3-dihydro-benzo[1,4]dioxin-6-yl)-amide; or trans-4-(quinolin-4-yloxymethyl)-cyclohexanecarboxylic acid (2,3-dihydro-benzo[1,4]dioxin-6-yl)-amide;

or a salt of said compound.

11. A pharmaceutical composition, comprising the compound of claim 1, or a pharmaceutically acceptable salt thereof, and at least one therapeutically inert excipient.

* * * * *